(12) United States Patent
Thomas et al.

(10) Patent No.: US 6,809,097 B1
(45) Date of Patent: Oct. 26, 2004

(54) QUINOLINE DERIVATIVES INHIBITING THE EFFECT OF GROWTH FACTORS SUCH AS VEGF

(75) Inventors: Andrew Peter Thomas, Macclesfield (GB); Laurent Francois Andre Hennequin, Cedex (FR); Patrick Ple, Cedex (FR)

(73) Assignees: Zeneca Limited, London (GB); Zeneca Pharma S.A., Cergy Cedex (FR)

( * ) Notice: Subject to any disclaimer, the term of this patent is extended or adjusted under 35 U.S.C. 154(b) by 0 days.

(21) Appl. No.: 09/254,440

(22) PCT Filed: Sep. 23, 1997

(86) PCT No.: PCT/GB97/02587

§ 371 (c)(1),
(2), (4) Date: Mar. 9, 1999

(87) PCT Pub. No.: WO98/13350

PCT Pub. Date: Apr. 2, 1998

(30) Foreign Application Priority Data

Sep. 25, 1996 (EP) ............................... 96402034

(51) Int. Cl.[7] ................... C07D 215/22; C07D 215/44; C07D 215/42; C07D 401/12; A61K 31/47

(52) U.S. Cl. .................... 514/235.2; 546/152; 546/153; 546/160; 546/167; 546/171; 546/178; 546/180; 544/128; 514/311; 514/312; 514/313; 514/314

(58) Field of Search ................ 546/152, 153, 546/160, 167, 171, 176, 178, 180; 544/128; 514/235.2, 311, 312, 313, 314

(56) References Cited

U.S. PATENT DOCUMENTS

| | | | | |
|---|---|---|---|---|
| 3,075,981 A | * | 1/1963 | Surrey ...................... | 260/256.4 |
| 3,272,824 A | * | 9/1966 | Ebitino et al. .............. | 260/288 |
| 3,376,195 A | | 4/1968 | Allais et al. ................. | 167/65 |
| 3,755,332 A | * | 8/1973 | Wasley et al. .............. | 260/288 |
| 3,936,461 A | | 2/1976 | Schwender et al. ......... | 260/289 |
| 4,421,920 A | * | 12/1983 | Baudouin et al. ........... | 546/163 |
| 5,145,843 A | * | 9/1992 | Arnold et al. ................ | 514/63 |
| 5,409,930 A | | 4/1995 | Spada et al. ................. | 514/248 |
| 5,480,883 A | | 1/1996 | Spada et al. ................. | 514/249 |
| 5,506,235 A | * | 4/1996 | Moyer et al. ................ | 514/293 |
| 5,646,153 A | | 7/1997 | Spada et al. ................. | 514/259 |
| 5,650,415 A | | 7/1997 | Tang et al. .................. | 514/312 |
| 5,656,643 A | | 8/1997 | Spada et al. ................. | 514/312 |
| 5,712,395 A | | 1/1998 | App et al. ................... | 544/344 |
| 5,792,771 A | | 8/1998 | App et al. ................... | 514/312 |
| RE36,256 E | | 7/1999 | Spada et al. ................. | 514/249 |
| 6,002,008 A | | 12/1999 | Wissner et al. .............. | 546/160 |

FOREIGN PATENT DOCUMENTS

| | | | |
|---|---|---|---|
| EP | 326 330 | | 8/1989 |
| FR | 2077455 | * | 9/1969 |
| FR | 2 077 455 | | 10/1971 |
| JP | 4320294 | * | 8/1968 |
| WO | WO 86/06718 | * | 11/1986 |
| WO | WO 87/04321 | | 7/1987 |
| WO | WO 92/20642 | | 11/1992 |
| WO | 92 21660 | | 12/1992 |

(List continued on next page.)

OTHER PUBLICATIONS

CAS printout for Bekhli et al. Chem. Abst. 73:25265.*
Rewcastle et al. J., Med. Chem. 38(18), pp. 3482–3487, 1995.*

(List continued on next page.)

Primary Examiner—Mukund J. Shah
Assistant Examiner—Hong Liu
(74) Attorney, Agent, or Firm—Morgan Lewis & Bockius LLP

(57) ABSTRACT

Compounds of the formula (I):

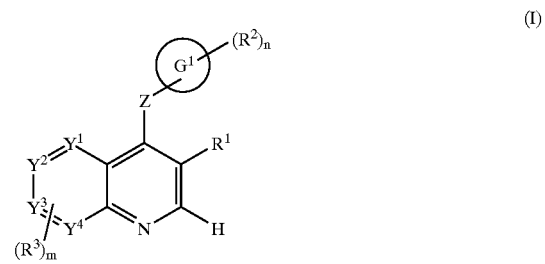

wherein: $R^2$ represents hydroxy, halogeno, $C_{1-3}$alkyl, $C_{1-3}$alkoxy, $C_{1-3}$alkanoyloxy, trifluoromethyl, cyano, amino or nitro; n is an integer from 0 to 5; Z represents —O—, —NH—, —S— or —CH$_2$—; $G^1$ represents phenyl or a 5–10 membered heteroaromatic cyclic or bicyclic group; $Y^1$, $Y^2$, $Y^3$ and $Y^4$ each independently represents carbon or nitrogen; $R^1$ represents fluoro or hydrogen; m is an integer from 1 to 3; $R^3$ represents hydrogen, hydroxy, halogeno, cyano, nitro, trifluoromethyl, $C_{1-3}$alkyl, —NR$^4$R$^5$ (wherein $R^4$ and $R^5$, can each be hydrogen or $C_{1-3}$alkyl), or a group $R^6$—$X^1$— wherein $X^1$ represents —CH$_2$— or a heteroatom linker group and $R^6$ is an alkyl, alkenyl or alkynyl chain optionally substituted by for example hydroxy, amino, nitro, alkyl, cycloalkyl, alkoxyalkyl, or an optionally substituted group selected from pyridone, phenyl and a heterocyclic ring, which alkyl, alkenyl or alkynyl chain may have a heteroatom linker group, or $R^6$ is an optionally substituted group selected from pyridone, phenyl and a heterocyclic ring and salts thereof, in the manufacture of a medicament for use in the production of an antiangiogenic and/or vascular permeability reducing effect in warm-blooded animals such as humans, processes for the preparation of such derivatives, pharmaceutical compositions containing a compound of formula I or a pharmaceutically acceptable salt thereof as active ingredient and compounds of formula I. The compounds of formula I and the pharmaceutically acceptable salts thereof inhibit the effects of VEGF, a property of value in the treatment of a number of disease states including cancer and rheumatoid arthritis.

24 Claims, No Drawings

FOREIGN PATENT DOCUMENTS

| | | |
|---|---|---|
| WO | 93 03030 | 2/1993 |
| WO | 93 13097 | 7/1993 |
| WO | WO 95/19169 | 7/1995 |
| WO | WO 95/21613 | 8/1995 |
| WO | 96 09294 | 3/1996 |
| WO | WO 96/30370 | 10/1996 |
| WO | WO 96/40648 | 12/1996 |
| WO | WO 96/40673 | 12/1996 |
| WO | WO 97/02266 | 1/1997 |
| WO | 97 03069 | 1/1997 |
| WO | 97 17329 | 5/1997 |
| WO | WO 97/22596 | 6/1997 |
| WO | WO 97/28161 | 8/1997 |
| WO | WO 97/30035 | 8/1997 |
| WO | WO 97/32856 | 9/1997 |
| WO | WO 97/34876 | 9/1997 |
| WO | WO 97/37999 | 10/1997 |
| WO | WO 97/42187 | 11/1997 |
| WO | WO 98/02434 | 1/1998 |
| WO | WO 98/13354 | 4/1998 |
| WO | WO 98/14431 | 4/1998 |
| WO | WO 98/23613 | 6/1998 |
| WO | WO 98/35958 | 8/1998 |
| WO | WO 98/43960 | 10/1998 |
| WO | WO 99/09024 | 2/1999 |
| WO | WO 99/10349 | 3/1999 |

OTHER PUBLICATIONS

Galanakis et al. J., Med. Chem. 38(18), pp. 3536–3546, 1995.*

Barlin et al. Aust. J. Chem. 47, pp. 1143–1154, 1994.*

Barlin et al. Aust. J. Chem. 46, pp. 1685–1693, 1993.*

Moyer et al. Bioorg. Med. Chem. Lett., 2(12), pp. 1589–1594, 1992.*

Ife et al. J. Med. Chem., 35(18), pp. 3413–3422, 1992.*

Lin et al., Heterocycles, 29(12), pp. 2353–2359, 1989.*

Yamamoto et al. J. Org. Chem. 39(24), pp. 3516–3519, 1974.*

Hester, Jr. J. Org. Chem. 39(15), pp. 2137–2142, 1974.*

Wright et al. J. Med. Chem. 14(11), pp. 1060–1066, 1971.*

Dolle, et al., "5,7–Dimethoxy–3–(4–pyridinyl)quinoline Is a Potent and Selective Inhibitor of Human Vascular b–Type Platelet–Derived Growth Factor Receptor Tyrosine Kinase," J.Med.Chem. 1994, vol. 37, pp. 2627–2629.

Maguire, et al., "A New Series of PDGF Receptor Tyrosine Kinase Inhibitors: 3–Substituted Quinoline Derivatives," J.Med.Chem. 1994, vol. 37, pp. 2129–2137.

Traxler, et al., "Recent advances in protein tyrosine Kinase inhibitors," Drugs of the Future 1995, vol. 20(12, pp. 1261–1274).

Rewcastle G W et al: "Tyrosine Kinase Inhibitors. 5. Synthesis and Structure–Activity Relationships for 4–(Phenylmethyl) Amino–and 4–(Phenylamino) Quinazolines as Potent Adenosine 5–Triphosphate Binding site Inhibitors of the Tyrosine Kinase Domain of the Epidermal Growth Factor Receptor" Journal of Medical Chemistry, vol. 38, No. 18, 1995,pp. 3482–3487.

Firsching A et al: "Antiproliferative and Angiostatic Activity of Suramin Analogues" Cancer Research, vol. 55, No. 21, Nov. 1, 1995, pp. 4957–4961.

Gravatt et al.; "DNA–Directed alkylating Agents " J.Med. Chem., vol. 34, 1991, pp. 1552–1560.

Chemical Abstracts, vol. 70, No. 15, Apr. 14, 1969, Columbus, Ohio, US; abstract No. 68193r, Hamana et al.: "4–Substituted quinoline derivatives", p. 366.

Chemical Abstracts, vol. 120, No. 17, Apr. 25, 1994, Columbus, Ohio, US; abstract No. 217227k, Barlin et al.: "Potential antimalarials . . . " p. 1030.

* cited by examiner

QUINOLINE DERIVATIVES INHIBITING THE EFFECT OF GROWTH FACTORS SUCH AS VEGF

This application is the national phase of international application PCT/G97/02587 filed Sep. 23, 1997 which designated the U.S.

The present invention relates to quinoline derivatives, processes for their preparation, pharmaceutical compositions containing them as active ingredient, methods for the treatment of disease states associated with angiogenesis and/or increased vascular permeability and to their use in the manufacture of medicaments for use in the production of antiangiogenic and/or vascular permeability reducing effects in warm-blooded animals such as humans.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57–66; Folkman, 1995, Nature Medicine 1: 27–31). Alteration of vascular permeability is thought to play a role in both normal and pathological physiological processes (Cullinan-Bove et al, 1993, Endocrinology 133: 829–837; Senger et al, 1993, Cancer and Metastasis Reviews, 12: 303–324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848–859; Kolch et al, 1995, Breast Cancer Research and Treatment, 36:139–155) and vascular permeability (Connolly et al, 1989, J. Biol. Chem. 264: 20017–20024). Antagonism of VEGF action by sequestration of VEGF with antibody can result in inhibition of tumour growth (Kim et al, 1993, Nature 362: 841–844).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1, the kinase insert domain-containing receptor, KDR (also referred to as Flk-1), and another fms-like tyrosine kinase receptor, Flt4. Two of these related RTKs, Flt and KDR, have been shown to bind VEGF with high affinity (De Vries et al, 1992, Science 255: 989–991; Terman et al, 1992, Biochem. Biophys. Res. Comm. 1992, 187: 1579–1586). Binding of VEGF to these receptors expressed in heterologous cells has been associated with changes in the tyrosine phosphorylation status of cellular proteins and calcium fluxes.

European Patent Publication No. 0326330 discloses certain quinoline, quinazoline and cinnoline plant fungicides. Certain of these plant fungicides are also stated to possess insecticidal and miticidal activity. There is however no disclosure or any suggestion that any of the compounds disclosed may be used for any purpose in animals such as humans. In particular, the European Patent Publication contains no teaching whatsoever concerning angiogenesis and/or increased vascular permeability mediated by growth factors such as VEGF.

The present invention is based on the surprising discovery that certain quinolines inhibit the effects of VEGF, a property of value in the treatment of disease states associated with angiogenesis and/or increased vascular permeability such as cancer, diabetes, psoriasis, rheumatoid arthritis, Kaposi's sarcoma, haemangioma, acute and chronic nephropathies, atheroma, arterial restenosis, autoimmune diseases, acute inflammation and ocular diseases with retinal vessel proliferation. Compounds of the present invention possess good activity against VEGF receptor tyrosine kinase whilst possessing some activity against epidermal growth factor (EGF) receptor tyrosine kinase. Furthermore, compounds of the present invention, possess substantially higher potency against VEGF receptor tyrosine kinase than against EGF receptor tyrosine kinase or FGF R1 receptor tyrosine kinase. Thus compounds of the invention which have been tested possess activity against VEGF receptor tyrosine kinase such that they may be used in an amount sufficient to inhibit VEGF receptor tyrosine kinase whilst demonstrating no significant activity against EGF receptor tyrosine kinase or FGF R1 receptor tyrosine kinase.

According to one aspect of the present invention there is provided the use of compounds of the formula I:

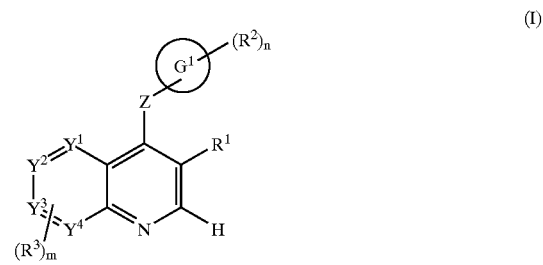

(I)

[wherein:

$R^2$ represents hydroxy, halogeno, $C_{1-3}$alkyl, $C_{1-3}$alkoxy, $C_{1-3}$alkanoyloxy, trifluoromethyl, cyano, amino or nitro;

n is an integer from 0 to 5;

Z represents —O—, —NH—, —S— or —CH$_2$—;

$G_1$ represents phenyl or a 5–10 membered heteroaromatic cyclic or bicyclic group containing 1 to 3 heteroatoms selected from O, S and N;

$Y^1$, $Y^2$, $Y^3$ and $Y^4$ each independently represents carbon or nitrogen with the proviso that $Y^1$, $Y^2$, $Y^3$ and $Y^4$ are not all nitrogen;

$R^1$ represents fluoro or hydrogen;

m is an integer from 1 to 3;

$R^3$ represents hydrogen, hydroxy, halogeno, cyano, nitro, trifluoromethyl, $C_{1-3}$alkyl, —NR$^4$R$^5$ (wherein $R^4$ and $R^5$, which may be the same or different, each represents hydrogen or $C_{1-3}$alkyl), or a group R$^6$—X$^1$— wherein $X^1$ represents —O—, —CH$_2$—, —OCO—, carbonyl, —S—, —SO—, —SO$_2$—, —NR$^7$CO—, —CONR$^8$—, —SO$_2$NR$^9$—, —NR$^{10}$SO$_2$— or —NR$^{11}$— (wherein $R^7$, $R^8$, $R^9$, $R^{10}$ and $R^{11}$ each independently represents hydrogen, $C_{1-3}$alkyl or $C_{1-3}$alkoxy$C_{2-3}$alkyl) and $R^6$ is selected from one of the following sixteen groups:

1) $C_{1-5}$alkyl which may be unsubstituted or which may be substituted with one or more groups selected from hydroxy, fluoro and amino;

2) $C_{1-5}$alkyl$X^2COR^2$ (wherein $X^2$ represents —O— or —NR$^{13}$— (wherein $R^{13}$ represents hydrogen, $C_{1-3}$alkyl or $C_{1-3}$alkoxy$C_{2-3}$alkyl) and $R^{12}$ represents —NR$^{14}R^{15}$— or —OR$^{16}$— (wherein $R^{14}$, $R^{15}$ and $R^{16}$ which may be the same or different each represents hydrogen, $C_{1-3}$alkyl or $C_{1-3}$alkoxy$C_{2-3}$alkyl));

3) $C_{1-5}$alkyl$X^3R^{17}$ (wherein $X^3$ represents —O—, —S—, —SO—, —SO$_2$—, —OCO—, —NR$^{18}$CO—, —CONR$^{19}$—, —SO$_2$NR$^{20}$—, —NR$^{21}$SO$_2$— or —NR$^{22}$— (wherein $R^{18}$, $R^{19}$, $R^{20}$, $R^{21}$ and $R^{22}$ each independently represents hydrogen, $C_{1-3}$alkyl or $C_{1-3}$alkoxy$C_{2-3}$alkyl) and $R^{17}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-3}$alkoxy and which cyclic group may bear one or two substituents selected from oxo, hydroxy, halogeno, $C_{1-4}$alkyl, $C_{1-4}$hydroxyalkyl and $C_{1-4}$alkoxy);

4) $C_{1-5}$alkyl$X^4C_{1-5}$alkyl$X^5R^{23}$ (wherein $X^4$ and $X^5$ which may be the same or different are each —O—, —S—, —SO—, —SO$_2$—, —NR$^{24}$CO—, —CONR$^{25}$—, —SO$_2$NR$^{26}$—, —NR$^{27}$SO$_2$— or —NR$^{28}$— (where $R^{24}$, $R^{25}$, $R^{26}$, $R^{27}$ and $R^{28}$ each independently represents hydrogen, $C_{1-3}$alkyl or $C_{1-3}$alkoxy$C_{2-3}$alkyl) and $R^{23}$ represents hydrogen or $C_{1-3}$alkyl);

5) $C_{1-5}$alkyl$R^{29}$ (wherein $R^{29}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);

6) $(CH_2)_qX^6R^{30}$ (wherein q is an integer from 0 to 5, $X^6$ represents a direct bond, —O—, —S—, —SO—, —SO$_2$—, —NR$^{31}$CO—, —CONR$^{32}$—, —SO$_2$NR$^{33}$—, —NR$^{34}$SO$_2$— or —NR$^{35}$— (wherein $R^{31}$, $R^{32}$, $R^{34}$ and $R^{35}$ each independently represents hydrogen, $C_{1-3}$alkyl or $C_{1-3}$alkoxy$C_{2-3}$alkyl) and $R^{30}$ is a phenyl group, a pyridone group or a 5 or 6 membered aromatic heterocyclic group with 1 to 3 heteroatoms selected from O, N and S, which phenyl, pyridone or aromatic heterocyclic group may carry up to 5 substituents selected from hydroxy, halogeno, amino, $C_{1-4}$alkyl, $C_{1-4}$alkoxy, $C_{1-4}$hydroxyalkyl, $C_{1-4}$hydroxyalkoxy, $C_{1-4}$aminoalkyl, $C_{1-4}$alkylamino, carboxy, cyano, —CONR$^{36}R^{37}$ and —NR$^{38}COR^{39}$ (wherein $R^{36}$, $R^{37}$, $R^{38}$ and $R^{39}$, which may be the same or different, each represents hydrogen, $C_{1-4}$alkyl or $C_{1-3}$alkoxy$C_{2-3}$alkyl));

7) $C_{2-6}$alkenyl$R^{29}$ (wherein $R^{29}$ is as defined hereinbefore);

8) $C_{2-6}$alkynyl$R^{29}$ (wherein $R^{29}$ is as defined hereinbefore);

9) $X^7R^{40}$ (wherein $X^7$ is —SO$_2$—, —O— or —CONR$^{41}R^{42}$— (wherein $R^{41}$ and $R^{42}$, which same or different, each represents hydrogen, $C_{1-3}$alkyl or $C_{1-3}$alkoxy$C_{2-3}$alkyl) and $R^{40}$ represents $C_{1-5}$alkyl which may be unsubstituted or which may be substituted with one or more groups selected from hydroxy, fluoro and amino) with the provisos that when $X^7$ is —SO$_2$—, $X^1$ is —O—, when $X^7$ is —O—, $X^1$ is carbonyl, when $X^7$ is —CONR$^{41}R^{42}$—, $X^1$ is —O— or NR$^{11}$ (wherein $R^{41}$, $R^{42}$ and $R^{11}$ are as defined hereinbefore);

10) $C_{2-6}$alkenyl$R^{30}$ (wherein $R^{30}$ is as defined hereinbefore);

11) $C_{2-6}$alkynyl$R^{30}$ (wherein $R^{30}$ is as defined hereinbefore);

12) $C_{2-6}$alkenyl$X^8R^{30}$ (wherein $X^8$ represents —O—, —S—, —SO—, —SO$_2$—, —NR$^{43}$CO—, —CONR$^{44}$—, —SO$_2$NR$^{45}$—, —NR$^{46}$SO$_2$— or —NR$^{47}$— (wherein $R^{43}$, $R^{44}$, $R^{45}$, $R^{46}$ and $R^{47}$ each independently represents hydrogen, $C_{1-3}$alkyl or $C_{1-3}$alkoxy$C_{2-3}$alkyl) and $R^{30}$ is as defined hereinbefore);

13) $C_{2-6}$alkynyl$X^9R^{30}$ (wherein $X^9$ represents —O—, —S—, —SO—, —SO$_2$—, —NR$^{48}$CO—, —CONR$^{49}$—, —SO$_2$NR$^{50}$—, —NR$^{51}$SO$_2$— or —NR$^{52}$— (wherein $R^{48}$, $R^{49}$, $R^{50}$, $R^{51}$ and $R^{52}$ each independently represents hydrogen, $C_{1-3}$alkyl or $C_{1-3}$alkoxy$C_{2-3}$alkyl) and $R^{30}$ is as defined hereinbefore);

14) $C_{1-3}$alkyl$X^{10}C_{1-3}$alkyl$R^{30}$ (wherein $X^{10}$ represents —O—, —S—, —SO—, —SO$_2$—, —NR$^{53}$CO—, —CONR$^{54}$—, —SO$_2$NR$^{55}$—, —NR$^{56}$SO$_2$— or —NR$^{57}$— (wherein $R^{53}$, $R^{54}$, $R^{55}$, $R^{56}$ and $R^{57}$ each independently represents hydrogen, $C_{1-3}$alkyl or $C_{1-3}$alkoxy$C_{2-3}$alkyl) and $R^{30}$ is as defined hereinbefore);

15) $R^{29}$ (wherein $R^{29}$ is as defined hereinbefore); and

16) $C_{1-3}$alkyl$X^{10}C_{1-3}$alkyl$R^{29}$ (wherein $X^{10}$ and $R^{29}$ are as defined hereinbefore);] and salts thereof, in the manufacture of a medicament for use in the production of an antiangiogenic and/or vascular permeability reducing effect in warm-blooded animals such as humans.

In one embodiment of the present invention $R^2$ represents hydroxy, halogeno, $C_{1-3}$alkyl, $C_{1-3}$alkoxy, trifluoromethyl, cyano, amino or nitro, preferably hydroxy, halogeno or $C_{1-2}$alkyl, especially hydroxy or halogeno.

In another embodiment of the present invention one $R^2$ is conveniently hydroxy, but advantageously one $R^2$ substituent is meta-hydroxy and the other one or more are each selected from halogeno, methyl and methoxy.

In another embodiment of the invention the phenyl group bearing $(R^2)_n$ is preferably of the formula II:

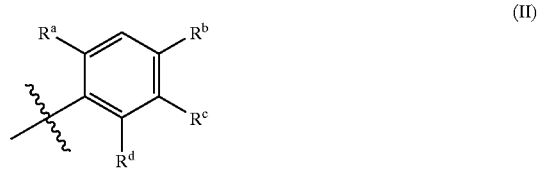

(II)

wherein:
$R^a$ represents hydrogen, methyl, fluoro or chloro, preferably hydrogen, fluoro or chloro, especially fluoro;
$R^b$ represents hydrogen, methyl, methoxy, cyano, bromo, fluoro or chloro;
$R^c$ represents hydrogen or hydroxy, especially hydroxy;
$R^d$ represents hydrogen, fluoro or chloro, especially hydrogen or fluoro.

Preferably in another embodiment of the invention two $R^2$ substituents are halogeno, and the other one or more are each selected from halogeno, hydroxy and methyl.

In a particular aspect of the present invention, the phenyl group bearing $(R^2)_n$ is the 2-fluoro-5-hydroxy-4-methylphenyl group, the 4-chloro-2-fluoro-5-hydroxyphenyl group, the 4-bromo-2-fluoro-5-hydroxyphenyl group, the 3-hydroxy-4-methylphenyl group, the 3-hydroxyphenyl group or the 4-chloro-2-fluorophenyl group.

More especially the phenyl group bearing $(R^2)_n$ is the 2-fluoro-5-hydroxy-4-methylphenyl group, the 4-chloro-2-fluoro-5-hydroxyphenyl group or the 4-chloro-2-fluorophenyl group.

Preferably n is an integer from 1 to 3, more preferably n is 2 or 3.

Preferably Z represents —O— or —NH—, but especially —NH—.

Advantageously $G^1$ represents phenyl or a 5–10 membered heteroaromatic cyclic or bicyclic group containing 1 to 3 nitrogen atoms.

Preferably $G^1$ represents phenyl or a 5–10 membered heteroaromatic cyclic or bicyclic group containing 1 to 2 nitrogen atoms.

More preferably $G^1$ represents phenyl.

Advantageously two of $Y^1, Y^2, Y^3$ and $Y^4$ each represent carbon and two each represent nitrogen, or only one of $Y^1, Y^2, Y^3$ and $Y^4$ represents nitrogen and the other three each represent carbon, or each of $Y^1, Y^2, Y^3$ and $Y^4$ represents carbon.

Preferably only one of $Y^1, Y^2, Y^3$ and $Y^4$ represents nitrogen and the other three each represent carbon, or each of $Y^1, Y^2, Y^3$ and $Y^4$ represents carbon.

More preferably each of $Y^1, Y^2, Y^3$ and $Y^4$ represents carbon.

Preferably $R^1$ represents hydrogen.

Preferably m is an integer from 1 to 2.

Advantageously $X^1$ represents —O—, —S—, —$NR^7CO$—, —$NR^{10}SO_2$— or —$NR^{11}$— (wherein $R^7, R^{10}$ and $R^{11}$ each independently represents hydrogen, $C_{1-2}$alkyl or $C_{1-2}$alkoxyethyl).

Preferably $X^1$ represents —O—, —S—, —$NR^7CO$—, —$NR^{10}SO_2$— (wherein $R^7$ and $R^{10}$ each independently represents hydrogen or $C_{1-2}$alkyl) or NH.

More preferably $X^1$ represents —O—, —S—, —$NR^7CO$— (wherein $R^7$ represents hydrogen or $C_{1-2}$alkyl) or NH.

Particularly $X^1$ represents —O— or —$NR^7CO$— (wherein $R^7$ represents hydrogen or $C_{1-2}$alkyl), more particularly —O— or —NHCO—, especially —O—.

Advantageously $X^2$ represents —O— or $NR^{13}$ (wherein $R^{13}$ represents hydrogen, $C_{1-3}$alkyl or $C_{1-2}$alkoxyethyl).

Advantageously $X^3$ represents —O—, —S—, —SO—, —$SO_2$—, —$NR^{18}CO$—, —$NR^{21}SO_2$— or —$NR^{22}$— (wherein $R^{18}, R^{21}$ and $R^{22}$ each independently represents hydrogen, $C_{1-2}$alkyl or $C_{1-2}$alkoxyethyl).

Preferably $X^3$ represents —O—, —S—, —SO—, —$SO_2$— or —$NR^{22}$— (wherein $R^{22}$ represents hydrogen, $C_{1-2}$alkyl or $C_{1-2}$alkoxyethyl).

More preferably $X^3$ represents —O— or —$NR^2$— (wherein $R^{22}$ represents hydrogen or $C_{1-2}$alkyl).

Advantageously $X^4$ and $X^5$ which may be the same or different each represents —O—, —S—, —SO—, —$SO_2$— or —$NR^{28}$— (wherein $R^{28}$ represents hydrogen $C_{1-3}$alkyl or $C_{1-2}$alkoxyethyl).

Preferably $X^4$ and $X^5$ which may be the same or different each represents —O—, —S— or —$NR^{28}$— (wherein $R^{28}$ represents hydrogen, $C_{1-2}$alkyl or $C_{1-2}$alkoxyethyl).

More preferably $X^4$ and $X^5$ which may be the sane or different each represents —O— or —NH—.

Advantageously $X^6$ represents a direct bond, —O—, —S—, $NR^{34}SO_2$ or —$NR^{35}$— (wherein $R^{35}$ represents hydrogen, $C_{1-2}$alkyl or $C_{1-2}$alkoxyethyl).

Preferably $X^6$ represents a direct bond, —O— or —$NR^{35}$— (wherein $R^{35}$ represents hydrogen or $C_{1-2}$alkyl).

More preferably $X^6$ represents a direct bond.

Preferably $X^7$ represents $SO_2$ or —$CONR^{41}R^{42}$— with the provisos that when $X^7$ is —$SO_2$—, $X^1$ is —O—, when $X^7$ is —$CONR^{41}R^{42}$—, $X^1$ is —O— or $NR^{11}$ (wherein $R^{41}, R^{42}$ and $R^{11}$ are as defined hereinbefore).

Advantageously $X^8$ represents —O—, —S— or —$NR^{47}$— (wherein $R^{47}$ represents hydrogen, $C_{1-2}$alkyl or $C_{1-2}$alkoxyethyl).

Preferably $X^8$ represents —O— or —$NR^{47}$— (wherein $R^{47}$ represents hydrogen or $C_{1-2}$alkyl).

Advantageously $X^9$ represents —O—, —S— or —$NR^{52}$— (wherein $R^{52}$ represents hydrogen, $C_{1-2}$alkyl or $C_{1-2}$alkoxyethyl).

Preferably $X^9$ represents —O— or —$NR^{52}$— (wherein $R^{52}$ represents hydrogen or $C_{1-2}$alkyl).

Advantageously $X^{10}$ represents —O—, —S— or —$NR^{57}$— (wherein $R^{57}$ represents hydrogen, $C_{1-2}$alkyl or $C_{1-2}$alkoxyethyl).

Preferably $X^{10}$ represents —O— or —$NR^{57}$— (wherein $R^{57}$ represents hydrogen or $C_{1-2}$alkyl).

$R^{29}$ is preferably pyrrolidinyl, piperazinyl, piperidinyl, morpholino or thiomorpholino which group may carry one or two substituents selected from oxo, hydroxy, halogeno, $C_{1-2}$alkyl, $C_{1-2}$hydroxyalkyl and $C_{1-2}$alkoxy.

Where $R^{30}$ is a 5 or 6-membered aromatic heterocyclic group, it preferably has 1 or 2 heteroatoms, selected from O, N and S, of which more preferably one is N, and may be substituted as hereinbefore defined.

$R^{30}$ is particularly a phenyl, pyridone, pyridyl, imidazolyl, thiazolyl, thienyl, triazolyl or pyridazinyl group which group may be substituted as hereinbefore defined, more particularly a phenyl, pyridone, pyridyl, imidazolyl, thiazolyl or triazolyl group, especially a phenyl, pyridyl, thiazolyl, imidazolyl or triazolyl group which group may be substituted as hereinbefore defined.

In one embodiment of the invention $R^{30}$ represents a pyridone, phenyl or 5 or 6-membered aromatic heterocyclic group with 1 to 3 heteroatoms selected from O, N and S, which group may preferably carry up to 2 substituents, more preferably up to one substituent, selected from the group of substituents as hereinbefore defined.

In the definition of $R^{30}$, conveniently substituents are selected from halogeno, $C_{1-4}$alkyl, $C_{1-4}$alkoxy and cyano, more conveniently substituents are selected from chloro, fluoro, methyl and ethyl.

Conveniently $R^3$ represents halogeno, cyano, nitro, trifluoromethyl or a group $R^6$—$X^1$— (wherein $R^6$ and $X^1$ are as defined hereinbefore).

Advantageously $R^3$ represents chloro, cyano, nitro, trifluoromethyl or a group $R^6$—$X^1$— (wherein $R^6$ and $X^1$ are as defined hereinbefore).

Conveniently $R^6$ is selected from one of the following sixteen groups:

1) $C_{1-5}$alkyl which may be unsubstituted or substituted with one or more fluorine atoms, or $C_{2-5}$alkyl which may be unsubstituted or substituted with one or more groups selected from hydroxy and amino;
2) $C_{2-3}$alkyl$X^2COR^{12}$ (wherein $X^2$ is as defined hereinbefore and $R^{12}$ represents —$NR^{14}R^{15}$— or $OR^{16}$— (wherein $R^{14}, R^{15}$ and $R^{16}$ which may be the same or different each represents hydrogen, $C_{1-2}$alkyl or $C_{1-2}$alkoxyethyl));

3) $C_{2-4}$alkyl$X^3R^{17}$ (wherein $X^3$ is as defined hereinbefore and $R^{17}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-3}$alkoxy and which cyclic group may bear one or two substituents selected from oxo, hydroxy, halogeno, $C_{1-3}$alkyl, $C_{1-3}$hydroxyalkyl and $C_{1-3}$alkoxy);

4) $C_{2-3}$alkyl$X^4C_{2-3}$alkyl$X^5R^{23}$ (wherein $X^4$ and $X^5$ are as defined hereinbefore and $R^{23}$ represents hydrogen or $C_{1-3}$alkyl);

5) $C_{1-5}$alkyl$R^{58}$ (wherein $R^{58}$ is a 5 or 6 membered saturated heterocyclic group with one or two heteroatoms, selected independently from O, S and N, which heterocyclic group is linked to $C_{1-5}$alkyl through a carbon atom and which heterocyclic group may bear one or two substituents selected from oxo, hydroxy, halogeno, $C_{1-3}$alkyl, $C_{1-3}$hydroxyalkyl and $C_{1-3}$alkoxy) or $C_{2-5}$alkyl$R^{59}$ (wherein $R^{59}$ is a 5 or 6 membered saturated heterocyclic group with one or two heteroatoms of which one is N and the other is selected independently from O, S and N, which heterocyclic group is linked to $C_{2-5}$alkyl through a nitrogen atom and which heterocyclic group may bear one or two substituents selected from oxo, hydroxy, halogeno, $C_{1-3}$alkyl, $C_{1-3}$hydroxyalkyl and $C_{1-3}$alkoxy);

6) $(CH_2)_qX^6R^{30}$ (wherein $X^6$ is as defined hereinbefore; q is an integer from 0 to 4 if $X^6$ is a direct bond and q is 0, 2 or 3 if $X^6$ is other than a direct bond; and $R^{30}$ is a phenyl group, a pyridone group or a 5 or 6 membered aromatic heterocyclic group with 1 to 3 heteroatoms selected from O, N and S, of which preferably one is N, which phenyl group, pyridone group or aromatic heterocyclic group may be substituted as hereinbefore defined, advantageously substituted with up to 2 substituents as hereinbefore defined, more preferably substituted with one substituent selected from the group of substituents as hereinbefore defined);

7) $C_{4-5}$alkenyl$R^{60}$ (wherein $R^{60}$ represents $R^{58}$ or $R^{59}$ as defined hereinbefore);

8) $C_{4-5}$alkynyl$R^{60}$ (wherein $R^{60}$ represents $R^{58}$ or $R^{59}$ as defined hereinbefore);

9) $X^7R^{40}$ (wherein $X^7$ is as defined hereinbefore and $R^{40}$ represents $C_{1-3}$alkyl which may be unsubstituted or which may be substituted with one or more groups selected from hydroxy, fluoro and amino);

10) $C_{3-5}$alkenyl$R^{30}$ (wherein $R^{30}$ is as defined hereinbefore);

11) $C_{3-5}$alkynyl$R^{30}$ (wherein $R^{30}$ is as defined hereinbefore);

12) $C_{4-5}$alkynyl$X^8R^{31}$ (wherein $X^8$ and $R^{30}$ are as defined hereinbefore);

13) $C_{4-5}$alkynyl$X^9R^{30}$ (wherein $X^9$ and $R^{30}$ are as defined hereinbefore);

14) $C_{1-3}$alkyl$X^{10}C_{1-3}$alkyl$R^{30}$ (wherein $X^{10}$ and $R^{30}$ are as defined hereinbefore);

15) $R^{29}$ (wherein $R^{29}$ is as defined hereinbefore); and

16) $C_{1-3}$alkyl$X^{11}C_{1-3}$alkyl$R^{29}$ (wherein $X^{11}$ and $R^{29}$ are as defined hereinbefore).

Advantageously $R^6$ is selected from one of the following eleven groups:

1) $C_{1-4}$alkyl which may be unsubstituted or substituted with one or more fluorine atoms, or $C_{2-4}$alkyl which may be unsubstituted or substituted with one or two groups selected from hydroxy and amino;

2) $C_{2-3}$alkyl$X^2COR^{12}$ (wherein $X^2$ is as defined hereinbefore and $R^{12}$ represents —$NR^{14}R^{15}$— or —$OR^{16}$— (wherein $R^{14}$, $R^{15}$ and $R^{16}$ which may be the same or different each represents hydrogen, $C_{1-2}$alkyl or $C_{1-2}$alkoxyethyl));

3) $C_{2-3}$alkyl$X^3R^{17}$ (wherein $X^3$ is as defined hereinbefore and $R^{17}$ is a group selected from $C_{1-3}$alkyl, cyclopentyl, cyclohexyl, pyrrolidinyl and piperidinyl which group is linked to $X^3$ through a carbon atom and which $C_{1-3}$alkyl group may bear one or two substituents selected from oxo, hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{2-3}$alkyl$X^4C_{2-3}$alkyl$X^5R^{23}$ (wherein $X^4$ and $X^5$ are as defined hereinbefore) and $R^{23}$ represents hydrogen or $C_{1-2}$alkyl);

5) $C_{1-4}$alkyl$R^{58}$ (wherein $R^{58}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-4}$alkyl through a carbon atom and which group may carry one or two substituents selected from oxo, hydroxy halogeno, $C_{1-2}$alkyl, $C_{1-2}$hydroxyalkyl and $C,2$alkoxy) or $C_{2-4}$alkyl$R^{59}$ (wherein $R^{59}$ is a group selected from morpholino, thiomorpholino, pyrrolidin-1-yl, piperazin-1-yl and piperidino which group may carry one or two substituents selected from oxo, hydroxy, halogeno, $C_{1-2}$alkyl, $C_{1-2}$hydroxyalkyl and $C_{1-2}$alkoxy); and 6) $(CH_2)_qX^6R^{30}$ (wherein $X^6$ is as defined hereinbefore; q is an integer from 1 to 3 if $X^6$ is a direct bond and q is 2 or 3 if $X^6$ is other than a direct bond; and $R^{30}$ is a phenyl group, a pyridone group or a 5 or 6 membered aromatic heterocyclic group with 1 to 2 heteroatoms selected from O, N and S, of which preferably one is N, which phenyl group, pyridone group or aromatic heterocyclic group may be substituted as hereinbefore defined, preferably substituted with one substituent selected from hydroxy, halogeno, $C_{1-2}$alkyl, $C_{1-2}$alkoxy, $C_{1-2}$hydroxyalkyl, $C_{1-2}$hydroxyalkoxy, carboxy, cyano, —$CONR^{36}R^{37}$ and —$NR^{38}COR^{39}$ (wherein $R^{36}$, $R^{37}$, $R^{38}$ and $R^{39}$, which may be the same or different, each represents hydrogen or $C_{1-2}$alkyl));

7) $C_{4-5}$alkenyl$R^{60}$ (wherein $R^{60}$ is as defined hereinbefore);

8) $C_{4-5}$alkynyl$R^{60}$ (wherein $R^{60}$ is as defined hereinbefore);

9) $C_{1-3}$alkyl$X^{10}C_{1-3}$alkyl$R^{30}$ (wherein $X^{10}$ and $R^{30}$ are as defined hereinbefore);

10) $R^{29}$ (wherein $R^{29}$ is as defined hereinbefore); and

11) $C_{1-3}$alkyl$X^{11}C_{1-3}$alkyl$R^{29}$ (wherein $X^{11}$ and $R^{29}$ are as defined hereinbefore).

Preferably $R^6$ is selected from one of the following nine groups:

1) $C_{1-3}$alkyl which may be unsubstituted or substituted with one or more fluorine atoms, or $C_{2-3}$alkyl which may be unsubstituted or substituted with one or two groups selected from hydroxy and amino;

2) 2-(3,3-dimethylureido)ethyl, 3-(3,3-dimethylureido) propyl, 2-(3-methylureido)ethyl, 3-(3-methylureido) propyl, 2-ureidoethyl, 3-ureidopropyl, 2-(N,N- dimethylcarbamoyloxy)ethyl, 3-(N,N-dimethylcarbamoyloxy)propyl, 2-N-methylcarbamoyloxy)ethyl, 3-(N-methylcarbamoyloxy)propyl, 2-(carbamoyloxy)ethyl, 3-(carbamoyloxy)propyl;

3) $C_{2-3}$alkyl$X^3R^{17}$ (wherein $X^3$ is as defined hereinbefore and $R^{17}$ is a group selected from $C_{1-2}$alkyl, cyclopentyl, cyclohexyl, pyrrolidinyl and piperidinyl which group is linked to $X^3$ through a carbon atom and which $C_{1-2}$alkyl group may bear one or two substituents selected from oxo, hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{2-3}$alkyl$X^4C_{2-3}$alkyl$X^5R^{23}$ (wherein $X^4$ and $X^5$ are as defined hereinbefore) and $R^{23}$ represents hydrogen or $C_{1-2}$alkyl);

5) $C_{1-2}$alkyl$R^{58}$ (wherein $R^{58}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-2}$alkyl through a carbon atom and which group may carry one substituent selected from oxo, hydroxy, halogeno, $C_{1-2}$alkyl, $C_{1-2}$hydroxyalkyl and $C_{1-2}$alkoxy) or $C_{2-3}$alkyl$R^{59}$ (wherein $R^{59}$ is a group selected from morpholino, thiomorpholino, piperidino, piperazin-1-yl and pyrrolidin-1-yl which group may carry one or two substituents selected from oxo. hydroxy, halogeno, $C_{1-2}$alkyl, $C_{1-2}$hydroxyalkyl and $C_{1-2}$alkoxy);

6) $(CH_2)_qX^6R^{30}$ (wherein $X^6$ is as defined hereinbefore; q is an integer from 1 to 3 if $X^6$ is a direct bond and q is 2 or 3 if $X^6$ is other than a direct bond; and $R^{30}$ is a group selected from phenyl, a pyridone group, pyridyl, imidazolyl, thiazolyl, thienyl, triazolyl and pyridazinyl, preferably selected from phenyl, a pryidone group, pyridyl, imidazolyl, thiazolyl and triazolyl which group may be substituted with one substituent selected from hydroxy, halogeno, $C_{1-2}$alkyl, $C_{1-2}$alkoxy, $C_{1-2}$hydroxyalkyl, $C_{1-2}$hydroxyalkoxy, carboxy, cyano, —CONR$^{36}$R$^{37}$ and —NR$^{38}$COR$^{39}$ (wherein $R^{36}$, $R^{37}$, $R^{38}$ and $R^{39}$ are as defined hereinbefore);

7) $C_{1-3}$alkyl$X^{10}C_{1-3}$alkyl$R^{30}$ (wherein $X^{10}$ and $R^{30}$ are as defined hereinbefore);

8) $R^{29}$ (wherein $R^{29}$ is as defined hereinbefore); and

9) $C_{1-3}$alkyl$X^{11}C_{1-3}$alkyl$R^{29}$ (wherein $X^{11}$ and $R^{29}$ are as defined hereinbefore)

More preferably $R^6$ represents 2-methylthiazol-4-ylmethyl, 2-acetamidothiazol-4-ylmethyl, 1-methylimidazol-2-ylmethyl, 4-pyridylmethyl, 2-(4-pyridyl)ethyl, 3-(4-pyridyl)propyl, 2-((N-(1-methylimidazol-4-ylsulphonyl)-N-methyl)amino)ethyl, 2-((N-(3-morpholinopropylsulphonyl)-N-methyl)amino)ethyl, 2-(N-methyl-N-4-pyridyl)amino)ethyl, 2-(4-oxidomorpholino)ethyl, 3-(4-oxidomorpholino)propyl, 2-(4-oxo-1,4-dihydro-1-pyridyl)ethyl, 3-(4-oxo-1,4-dihydro-1-pyridyl)propyl, methyl, ethyl, trifluoromethyl, 2,2,2-trifluoroethyl, 2-hydroxyethyl, 3-hydroxypropyl, 2-(N,N-dimethylsulphamoyl)ethyl, 2-(N-methylsulphamoyl)ethyl, (1,3dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-(1,2,4-triazol-1-yl)ethyl, 2-(1,2,4-triazol-4-yl)ethyl, 3-(1,2,4-triazol-1-yl)propyl, 3-(1,2,4-triazol-4-yl)propyl, 2-(4-pyridyloxy)ethyl, 3-(4-pyridyloxy)propyl, 2-(4-pyridylamino)ethyl, 3-(4-pyridylamino)propyl, 2-(2-methylimidazol-1-yl)ethyl, 3-(2-methylimidazol-1-yl)propyl, 2-(5-methyl-1,2,4-triazol-1-yl)ethyl, 3-(5-methyl-1,2,4-triazol-1-yl)propyl, morpholino, N-methylpiperazinyl, piperazinyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, 2-methoxyethyl, 3-methoxypropyl, 2-(imidazol-1-yl)ethyl, 2-(1,2,3-triazol-1-yl)ethyl, 2-(1,2,3-triazol-2-yl)ethyl, 3imidazol-1-yl)propyl, 3-(1,2,3-triazol-1-yl)propyl, 3-(1,2,3-triazol-2-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 2-(methylsulphinyl)ethyl, benzyl, 2-sulphamoylethyl or 2-(methylsulphonyl)ethyl. Especially $R^6$ represents methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 3-(3-pyridyl)propyl, benzyl, 2-(4-pyridyloxy)ethyl, 2-(4-pyridylamino)ethyl, or 2-(4-oxo-1,4-dihydro-1-pyridyl)ethyl.

More especially $R^6$ represents methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-methylsulphonyl)ethyl, 2-(N,N-dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, benzyl, 2-(4-pyridyloxy)ethyl, 2-(4-pyridylamino)ethyl, or 2-(4-oxo-1,4-dihydro-1-pyridyl)ethyl.

Preferably $R^3$ is attached to $Y^2$ or $Y^3$.

More preferably $Y^2$ is carbon and bears a value of $R^3$ which is not $R^6$—$X^1$ and $Y^3$ is carbon and bears a value of $R^3$ which is $R^6$—$X^1$.

According to one aspect of the present invention there is provided the use of compounds of the formula Ia:

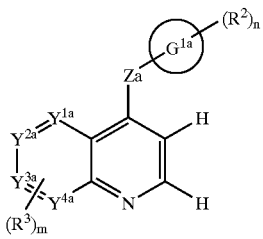

(Ia)

[wherein:

$R^2$, $R^3$, m and n are as defined hereinbefore;

Za represents —O— or —NH—;

$G^{1a}$ represents phenyl or 1H-indazol-6-yl; and $Y^{1a}$ and $Y^{4a}$ each independently represents C—H or nitrogen and $Y^{2a}$ and $Y^{3a}$ each represent carbon or nitrogen with the proviso that no more than two of $Y^{1a}$, $Y^{2a}$, $Y^{3a}$ and $Y^{4a}$ can be nitrogen at the same time;] and salts thereof, in the manufacture of a medicament for use in the production of an antiangiogenic and/or vascular permeability reducing effect in warm-blooded animals such as humans.

According to one aspect of the present invention there is provided compounds of the formula Ib:

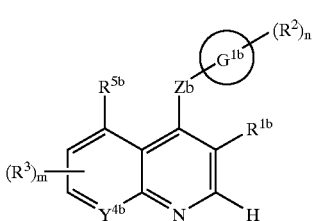

(Ib)

[wherein:

$R^2$, $R^3$, m and n are as defined hereinbefore;

Zb represents —O— or —NH—;

$G^{1b}$ represents phenyl or 1H-indazol-6-yl;

$Y^{4b}$ represents C—H or nitrogen;

$R^{1b}$ represents fluoro or hydrogen; and $R^{5b}$ represents hydrogen, hydroxy, methoxy, amino, nitro or halogeno;] and salts thereof, for use as medicaments.

According to one aspect of the present invention there is provided the use of pounds of the formula Ic:

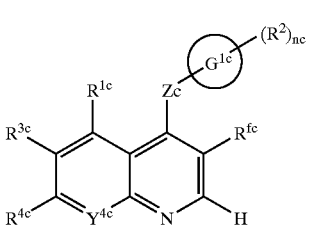

(Ic)

[wherein:

$G^{1c}$ represents phenyl, and additionally $G^{1c}$ may be 1H-indazol-6-yl;

$Y^{4c}$ represents C—H, and additionally $Y^{4c}$ may be nitrogen;

$R^{fc}$ represents hydrogen and additionally $R^{fc}$ may be fluoro;

$R^{2c}$ represents hydroxy, halogeno, $C_{1-3}$alkyl, $C_{1-3}$alkoxy, $C_{1-3}$alkanoyloxy, trifluoromethyl, cyano, amino or nitro;

nc is an integer from 1 to 5, and additionally nc may be 0;

Zc represents —O—, —NH—, —S— or —CH$_2$—;

$R^{1c}$ represents hydrogen, hydroxy, methoxy, amino, nitro or halogeno;

$R^{3c}$ represents hydrogen, hydroxy, halogeno, cyano, nitro, trifluoromethyl, $C_{1-3}$alkyl, $C_{1-3}$alkoxy, $C_{1-3}$alkylthio, or —NR$^{6c}$R$^{7c}$, (wherein $R^{6c}$ and $R^{7c}$, which may be the same or different, each represents hydrogen or $C_{1-3}$alkyl), and additionally $R^{3c}$ may have any of the values of $R^{5c}$—$X^{1c}$— (wherein $R^{5c}$ and $X^{1c}$ are as defined hereinafter);

$R^{4c}$ represents hydroxy, hydroxy, halogeno, cyano, nitro, trifluoromethyl, $C_{1-3}$alkyl, —NR$^{8c}$R$^{9c}$ (wherein $R^{8c}$ and $R^{9c}$, which may be the same or different, each represents hydrogen or $C_{1-3}$alkyl), or a group $R^{5c}$—$X^{1c}$— wherein $X^{1c}$ represents —O—, —CH$_2$—, —S—, —SO—, —SO$_2$—, —NR$^{10c}$CO—, —CONR$^{11c}$—, —SO$_2$NR$^{12c}$—, —NR$^{13c}$SO$_2$— or —NR$^{14c}$— (wherein $R^{10c}$, $R^{11c}$, $R^{12c}$, $R^{13c}$ and $R^{14c}$ each independently represents hydrogen, $C_{1-3}$alkyl or $C_{1-3}$alkoxyC$_{2-3}$alkyl), and additionally $X^{1c}$ represents —OCO—, and $R^{5c}$ is selected from one of the following eight groups:

1) $C_{1-5}$alkyl which may be unsubstituted or which may be substituted with one or more groups selected from hydroxy, fluoro and amino;

2) $C_{1-5}$alkylX$^{2c}$COR$^{15c}$ (wherein $X^{2c}$ represents —O— or NR$^{16c}$— (wherein $R^{16c}$ represents hydrogen, $C_{1-3}$alkyl or $C_{1-3}$alkoxyC$_{2-3}$alkyl) and $R^{15c}$ represents —NR$^{17c}$R$^{18c}$— or —OR$^{19c}$— (wherein $R^{17c}$, $R^{18c}$ and $R^{19c}$ which may be the same or different each represents hydrogen, $C_{1-3}$alkyl or $C_{1-3}$alkoxyC$_{2-3}$alkyl));

3) $C_{1-5}$alkylX$^{3c}$R$^{20c}$ (wherein $X^{3c}$ represents —O—, —S—, —SO—, —SO$_2$—, —OCO—, —NR$^{21c}$CO, —CONR$^{22c}$—, —SO$_2$NR$^{23c}$—, —NR$^{24c}$SO$_2$— or —NR$^{25c}$— (wherein $R^{21c}$, $R^{22c}$, $R^{23c}$, $R^{24c}$ and $R^{25c}$ each independently represents hydrogen, $C_{1-3}$alkyl or $C_{1-3}$alkoxyC$_{2-3}$alkyl) and $R^{20c}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);

4) $C_{1-5}$alkylX$^{4c}$C$_{1-5}$alkylX$^{5c}$R$^{26c}$ (wherein $X^{4c}$ and $X^{5c}$ which may be the same or different are each —O—, —S—, —SO—, —SO$_2$—, —NR$^{27c}$CO—, —CONR$^{28c}$—, —SO$_2$NR$^{29c}$—, —NR$^{30c}$SO$_2$— or —NR$^{31c}$— (wherein $R^{27c}$, $R^{28c}$, $R^{29c}$, $R^{30c}$ and $R^{31c}$ each independently represents hydrogen, $C_{1-3}$alkyl or $C_{1-3}$alkoxyC$_{2-3}$alkyl) and $R^{26c}$ represents hydrogen or $C_{1-3}$alkyl);

5) $C_{1-5}$alkylR$^{32c}$ (wherein $R^{32c}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);

6) (CH$_2$)$_{qc}$X$^{6c}$R$^{33c}$ (wherein qc is an integer from 0 to 5, $X^{6c}$ represents a direct bond, —O—, —S—, —SO—, —SO$_2$—, —NR$^{34c}$CO—, —CONR$^{35c}$—, —SO$_2$NR$^{36c}$—, —NR$^{37c}$SO$_2$— or —NR$^{38c}$— (wherein R$^{34c}$, R$^{35c}$, R$^{36c}$, R$^{37c}$ and R$^{38c}$ each independently represents hydrogen, C$_{1-3}$alkyl or C$_{1-3}$alkoxyC$_{2-3}$alkyl) and R$^{33c}$ is a phenyl group, a pyridone group or a 5 or 6 membered aromatic heterocyclic group with 1 to 3 heteroatoms selected from O, N and S, which phenyl, pyridone or aromatic heterocyclic group may carry up to 5 substituents selected from hydroxy, halogeno, C$_{1-4}$alkyl, C$_{1-4}$alkoxy, C$_{1-4}$hydroxyalkyl, C$_{1-4}$hydroxyalkoxy, carboxy, cyano, —CONR$^{39c}$R$^{40c}$ and —NR$^{41c}$COR$^{42c}$ (wherein R$^{39c}$, R$^{40c}$, R$^{41c}$ and R$^{42c}$, which may be the same or different, each represents hydrogen or C$_{1-4}$alkyl));

7) C$_{2-6}$alkenylR$^{32c}$ (wherein R$^{32c}$ is as defined hereinbefore); and 8) C$_{2-6}$alkenylR$^{32c}$ (wherein R$^{32c}$ is as defined hereinbefore);] and salts thereof, as medicaments.

Preferably the invention relates to the use of compounds of formula Ic for the treatment of disease states associated with angiogenesis and/or increased vascular permeablility. In one embodiment of the present invention R$^{2c}$ represents hydroxy, halogeno, C$_{1-3}$alkyl, C$_{1-3}$alkoxy, trifluoromethyl, cyano, amino or nitro, preferably hydroxy, halogeno or C$_{1-2}$alkyl, especially hydroxy or halogeno.

In another embodiment of the present invention one R$^{2c}$ is conveniently hydroxy, but advantageously one R$^{2c}$ substituent is meta-hydroxy and the other one or more are each selected from halogeno, methyl and methoxy.

In another embodiment of the invention the phenyl group bearing $(R^{2c})_{nc}$ is preferably of the formula IIc:

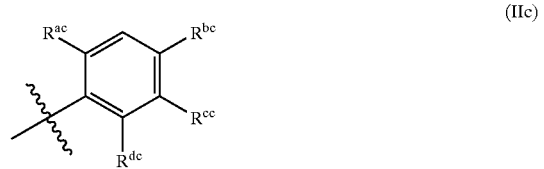

(IIc)

wherein:
R$^{ac}$ represents hydrogen, methyl, fluoro or chloro, preferably hydrogen, fluoro or chloro, especially fluoro;
R$^{bc}$ represents hydrogen, methyl, methoxy, bromo, fluoro or chloro, and additionally R$^{bc}$ may be cyano;
R$^{cc}$ represents hydrogen or hydroxy, especially hydroxy;
R$^{dc}$ represents hydrogen, fluoro or chloro, especially hydrogen or fluoro.

Preferably in another embodiment of the invention two R$^{2c}$ substituents are halogeno, and the other one or more are each selected from halogeno, hydroxy and methyl. In a particular aspect of the present invention, the phenyl group bearing $(R^{2c})_{nc}$ is the 2-fluoro-5-hydroxy-4-methylphenyl group, the 4-chloro-2-fluoro-5-hydroxyphenyl group or the 4-chloro-2-fluorophenyl group, and additional values of the phenyl group bearing $(R^{2c})_{nc}$ are the 3-hydroxy-4-methylphenyl group, the 3-hydroxyphenyl group and the 4-bromo-2-fluoro-5-hydroxyphenyl group.

Preferably nc is an integer from 1 to 3, more preferably nc is 2 or 3.

Preferably Zc represents —O— or —NH—, but especially —NH—.

Preferably R$^{1c}$ represents hydrogen, amino, nitro or halogeno, but especially hydrogen.

Advantageously R$^{3c}$ represents hydrogen, hydroxy, cyano, nitro, trifluoromethyl, C$_{1-3}$alkyl, C$_{1-3}$alkoxy or amino, and additional advantageous values of R$^{3c}$ are methoxycarbonyl, 3-morpholinopropoxy and 3-morpholinopropylcarbamoyl.

Preferably R$^{3c}$ represents hydrogen, hydroxy, cyano, nitro, trifluoromethyl, methyl, ethyl, methoxy or ethoxy, and additional preferred values of R$^{3c}$ are methoxycarbonyl, 3-morpholinopropoxy and 3-morpholinopropylcarbamoyl; more preferably R$^{3c}$ represents hydrogen, cyano, nitro, trifluoromethyl, hydroxy, methyl or methoxy, and an additional more preferred value of R$^{3c}$ is methoxycarbonyl; especially R$^{3c}$ represents cyano or methoxy.

Preferably R$^{fc}$ is hydrogen.
Preferably G$^{1c}$ is phenyl.
Preferably Y$^{4c}$ is C—H.

Conveniently R$^{4c}$ represents halogeno, cyano, nitro, trifluoromethyl or a group R$^{5c}$—X$^{1c}$— (wherein R$^{5c}$ and X$^{1c}$ are as defined hereinbefore).

Advantageously R$^{4c}$ represents cyano, nitro, trifluoromethyl or a group R$^{5c}$—X$^{1c}$— (wherein R$^{5c}$ and X$^{1c}$ are as defined hereinbefore).

Preferably R$^{4c}$ represents a group R$^{5c}$—X$^{1c}$— (wherein R$^{5c}$ and X$^{1c}$ are as defined hereinbefore).

Advantageously X$^{1c}$ represents —O—, —S—, —NR$^{10c}$CO—, —NR$^{13c}$SO$_2$— or —NR$^{14c}$— (wherein R$^{10c}$, R$^{13c}$ and R$^{14c}$ each independently represents hydrogen, C$_{1-2}$alkyl or C$_{1-2}$alkoxyethyl).

Preferably X$^{14c}$ represents —O—, —S—, —NR$^{10c}$CO— or —NR$^{13c}$SO$_2$— (wherein R$^{10c}$ and R$^{13c}$ each independently represents hydrogen or C$_{1-2}$alkyl).

More preferably X$^{1c}$ represents —O—, or —NHCO—, especially —O—.

Advantageously X$^{3c}$ represents —O—, —S—, —SO—, —SO$_2$—, —NR$^{21c}$CO—, —NR$^{24c}$SO$_2$— or —NR$^{25c}$— (wherein R$^{21c}$, R$^{24c}$ and R$^{25c}$ each independently represents hydrogen, C$_{1-2}$alkyl or C$_{1-2}$alkoxyethyl).

Preferably X$^{3c}$ represents —O—, —S—, —SO—, —SO$_2$— or —NR$^{25c}$ (wherein R$^{25c}$ represents hydrogen, C$_{1-2}$alkyl or C$_{1-2}$alkoxyethyl).

More preferably X$^{3c}$ represents —O— or —NR$^{25c}$— (wherein R$^{25c}$ represents hydrogen or C$_{1-2}$alkyl).

Advantageously X$^{4c}$ and X$^{5c}$ which may be the same or different each represents —O—, —S—, —SO—, —SO$_2$— or —NR$^{31c}$— (wherein R$^{31c}$ represents hydrogen, C$_{1-2}$alkyl or C$_{1-2}$alkoxyethyl).

Preferably X$^{4c}$ and X$^{5c}$ which may be the same or different each represent —O—, —S— or —NR$^{31c}$— (wherein R$^{31c}$ represents hydrogen, C$_{1-2}$alkyl or C$_{1-2}$alkoxyethyl).

Advantageously X$^{6c}$ represents a direct bond, —O—, —S— or —NR$^{38c}$— (wherein R$^{38c}$ represents hydrogen, C$_{1-2}$alkyl or C$_{1-2}$alkoxyethyl), and an additional advantageous value of X$^{6c}$ is —NR$^{37c}$SO$_2$, Preferably X$^{6c}$ represents a direct bond, —O— or —NR$^{38c}$— (wherein R$^{38c}$ represents hydrogen or C$_{1-2}$alkyl).

Conveniently R$^{5c}$ is selected from one of the following eight groups:

1) C$_{1-5}$alkyl which may be unsubstituted or substituted with one or more fluorine atoms, or C$_{2-5}$alkyl which may be unsubstituted or substituted with one or more groups selected from hydroxy and amino;

2) C$_{2-3}$alkylX$^{2c}$COR$^{15c}$ (wherein X$^{2c}$ is as defined hereinbefore and R$^{15c}$ represents —NR$^{17c}$R$^{18c}$— or —OR$_{19c}$— (wherein R$^{17c}$, R$^{18c}$ and R$^{19c}$ which may be the same or different each represents hydrogen, C$_{1-2}$alkyl or C$_{1-2}$alkoxyethyl));

3) C$_{2-4}$alkylX$^{3c}$R$^{20c}$ (wherein X$^{3c}$ is as defined hereinbefore and R$^{20c}$ represents hydrogen, C$_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-3}$alkoxy and which cyclic group may bear one or two substituents selected from oxo, hydroxy, halogeno, $C_{1-3}$alkyl, $C_{1-3}$hydroxyalkyl and $C_{1-3}$alkoxy);

4) $C_{2-3}$alkyl$X^{4c}C_{2-3}$alkyl$X^{5c}R^{26c}$ (wherein $X^{4c}$ and $X^{5c}$ are as defined hereinbefore and $R^{26c}$ represents hydrogen or $C_{1-3}$alkyl);

5) $C_{1-5}$alkyl$R^{43c}$ (wherein $R^{43c}$ is a 5 or 6 membered saturated heterocyclic group with one or two heteroatoms, selected independently from O, S and N, which heterocyclic group is linked to $C_{1-5}$alkyl through a carbon atom and which heterocyclic group may bear one or two substituents selected from oxo, hydroxy, halogeno, $C_{1-3}$alkyl, $C_{1-3}$hydroxyalkyl and $C_{1-3}$alkoxy) or $C_{2-5}$alkyl$R^{44c}$ (wherein $R^{44c}$ is a 5 or 6 membered saturated heterocyclic group with one or two heteroatoms of which one is N and the other is selected independently from O, S and N, which heterocyclic group is linked to $C_{2-5}$alkyl through a nitrogen atom and which heterocyclic group may bear one or two substituents selected from oxo, hydroxy, halogeno, $C_{1-3}$alkyl, $C_{1-3}$hydroxyalkyl and $C_{1-3}$alkoxy);

6) $(CH_2)_{qc}X^{6c}R^{33c}$ (wherein $X^{6c}$ is as defined hereinbefore; qc is an integer from 0 to 4 if $X^{6c}$ is a direct bond and q is 0, 2 or 3 if $X^{6c}$ is other than a direct bond; and $R^{33c}$ is a phenyl group, a pyridone group or a 5 or 6 membered aromatic heterocyclic group with 1 to 3 heteroatoms selected from O, N and S, of which preferably one is N, which phenyl group, pyridone group or aromatic heterocyclic group may be substituted as hereinbefore defined, advantageously substituted with up to 2 substituents as hereinbefore defined, more preferably substituted with one substituent selected from the group of substituents as hereinbefore defined);

7) $C_{4-5}$alkenyl$R^{45c}$ (wherein $R^{45c}$ represents $R^{43c}$ or $R^{44c}$ as defined hereinbefore); and 8) $C_{4-5}$alkynyl$R^{45c}$ (wherein $R^{45c}$ represents $R^{43c}$ or $R^{44c}$ as defined hereinbefore).

Advantageously $R^{5c}$ is selected from one of the following eight groups:

1) $C_{1-4}$alkyl which may be unsubstituted or substituted with one or more fluorine atoms, or $C_{2-4}$alkyl which may be unsubstituted or substituted with one or two groups selected from hydroxy and amino;

2) $C_{2-3}$alkyl$X^{2c}COR^{15c}$ (wherein $X^{2c}$ is as defined hereinbefore and $R^{15c}$ represents —$NR^{17c}R^{18c}$— or —$OR^{19c}$— (wherein $R^{17c}$, $R^{18c}$ and $R^{19c}$ which may be the same or different each represents hydrogen, $C_{1-2}$alkyl or $C_{1-2}$alkoxyethyl));

3) $C_{2-3}$alkyl$X^{3c}R^{20c}$ (wherein $X^{3c}$ is as defined hereinbefore and $R^{20c}$ is a group selected from $C_{1-3}$alkyl, cyclopentyl, cyclohexyl, pyrrolidinyl and piperidinyl which group is linked to $X^{3c}$ through a carbon atom and which $C_{1-3}$alkyl group may bear one or two substituents selected from oxo, hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{2-3}$alkyl$X^{4c}C_{2-3}$alkyl$X^{5c}R^{26c}$ (wherein $X^{4c}$ and $X^{5c}$ are as defined hereinbefore) and $R^{26c}$ represents hydrogen or $C_{1-2}$alkyl);

5) $C_{1-4}$alkyl$R^{43c}$ (wherein $R^{43c}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-4}$alkyl through a carbon atom and which group may carry one or two substituents selected from oxo, hydroxy, halogeno, $C_{1-2}$alkyl, $C_{1-2}$hydroxyalkyl and $C_{1-2}$alkoxy) or $C_{2-4}$alkyl$R^{44c}$ (wherein $R^{44c}$ is a group selected from morpholino, thiomorpholino, pyrrolidin-1-yl, piperazin-1-yl and piperidino which group may carry one or two substituents selected from oxo, hydroxy, halogeno, $C_{1-2}$alkyl, $C_{1-2}$hydroxyalkyl and $C_{1-2}$alkoxy); and 6) $(CH_2)_{qc}X^{6c}R^{33c}$ (wherein $X^{6c}$ is as defined hereinbefore; qc is an integer from 1 to 3 if $X^{6c}$ is a direct bond and qc is 2 or 3 if $X^{6c}$ is other than a direct bond; and $R^{33c}$ is a phenyl group, a pyridone group or a 5 or 6 membered aromatic heterocyclic group with 1 to 2 heteroatoms selected from O, N and S, of which preferably one is N, which phenyl group, pyridone group or aromatic heterocyclic group may be substituted as hereinbefore defined, preferably substituted with one substituent selected from hydroxy, halogeno, $C_{1-2}$alkyl, $C_{1-2}$alkoxy, $C_{1-2}$hydroxyalkyl, $C_{1-2}$hydroxyalkoxy, carboxy, cyano, —$CONR^{39c}R^{40c}$ and —$NR^{41c}COR^{42c}$ (wherein $R^{39c}$, $R^{40c}$, $R^{41c}$ and $R^{42c}$ which may be the same or different, each represents hydrogen or $C_{1-2}$alkyl));

7) $C_{4-5}$alkenyl$R^{45c}$ (wherein $R^{45c}$ is as defined hereinbefore); and 8) $C_{4-5}$alkynyl$R^{45c}$ (wherein $R^{45c}$ is as defined hereinbefore).

Preferably $R^{5c}$ is selected from one of the following six groups:

1) $C_{1-3}$alkyl which may be unsubstituted or substituted with one or more fluorine atoms, or $C_{2-3}$alkyl which may be unsubstituted or substituted with one or two groups selected from hydroxy and amino;

2) 2-(3,3-dimethylureido)ethyl, 3-(3,3-dimethylureido) propyl, 2-(3-methylureido)ethyl, 3-(3-methylureido) propyl, 2-ureidoethyl, 3-ureidopropyl, 2-(<u>N</u>,<u>N</u>-dimethylcarbamoyloxy)ethyl, 3-<u>N</u><u>N</u>,<u>N</u>-dimethylcarbamoyloxy)propyl, 2-(<u>N</u>-methylcarbamoyloxy)ethyl, 3-(<u>N</u>-methylcarbamoyloxy)propyl, 2-(carbamoyloxy)ethyl, 3-(carbamoyloxy)propyl;

3) $C_{2-3}$alkyl$X^{3c}R^{20c}$ (wherein $X^{3c}$ is as defined hereinbefore and $R^{20c}$ is a group seleceted from $C_{1-2}$alkyl, cyclopentyl, cyclohexyl, pyrrolidinyl and piperidinyl which group is linked to $X^{3c}$ from hydroxy, halogeno and $C_{1-2}$alkoxy and oxo, and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{2-3}$alkyl$X^{4c}C_{2-3}$alkyl$X^{5c}R^{26c}$ (wherein $X^{4c}$ and $X^{5c}$ are as defined hereinbefore) and $R^{26c}$ represents hydrogen or $C_{1-2}$alkyl);

5) $C_{1-2}$alkyl$R^{43c}$ (wherein $R^{43c}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-2}$alkyl through a carbon atom and which group may carry one substituent selected from oxo, hydroxy, halogeno, $C_{1-2}$alkyl, $C_{1-2}$hydroxyalkyl and $C_{1-2}$alkoxy) or $C_{2-3}$alkyl$R^{44c}$ (wherein $R^{44c}$ is a group selected from morpholino, thiomorpholino, piperidino, piperazin-1-yl and pyrrolidin-1-yl which group may carry one substituent, or two substitutents, selected from oxo, hydroxy, halogeno, $C_{1-2}$alkyl, $C_{1-2}$hydroxyalkyl and $C_{1-2}$alkoxy); and 6) $(CH_2)_{qc}X^{6c}R^{33c}$ (wherein $X^{6c}$ is as defined hereinbefore; qc is an integer from 1 to 3 if $X^{6c}$ is a direct bond and qc is 2, or 3, if $X^{6c}$ is other than a direct bond; and $R^{33c}$ is a group selected from phenyl, a pyridone group, pyridyl, imidazolyl, thiazolyl, thienyl, triazolyl and pyridazinyl, preferably selected from phenyl, a pyridone group, pyridyl, imidazolyl, thiazolyl and triazolyl which group may be substituted with one substituent selected from hydroxy, halogeno, $C_{1-2}$alkyl, $C_{1-2}$alkoxy, $C_{1-2}$hydroxyalkyl, $C_{1-2}$hydroxyalkoxy, carboxy, cyano, —$CONR^{39c}R^{40c}$ and $NR^{41c}COR^{42c}$ (wherein $R^{39c}$ $R^{40c}$, $R^{41c}$ and $R^{42c}$ are as defined hereinbefore).

More preferably $R^{5c}$ represents methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino) propyl, 2-methylthiazol-4-ylmethyl, 2-acetamidothiazol-4-ylmethyl, 1-methylimidazol-2-ylmethyl, 2-(imidazol-1-yl)ethyl, 2-(1,2,3-triazol-1-yl)ethyl, 2-(1,2,3-triazol-2-yl)ethyl, 2-(1-yl)ethyl, 2-(1,2,4-triazol-4-yl)ethyl, 4-pyridylmethyl, 2-(4-pyridyl)ethyl, 3-(4-pyridyl)propyl, benzyl, 2-(4-pyridyloxy)ethyl, 2-(4-pyridylamino)ethyl or 2-(4-oxo-1,4-dihydro-1-pyridyl)ethyl, and additional more preferred values for $R^{5c}$ are 3-(3-pyridyl)propyl, 2-((N-(1-methylimidazol-4-ylsulphonyl)-N-methyl)amino)ethyl, 2-((N-methyl-N-4-pyridyl)amino)ethyl, 2-(4-oxidomorpholino)ethyl, 3-(4-oxidomorpholino)propyl, 3-(4-oxo-1,4-dihydro-1-pyridyl)propyl, 3-(1,2,4-triazol-1-yl)propyl, 3-(1,2,4-triazol-4-yl)propyl, 3-(4-pyridyloxy) propyl, 3-(4-pyridylamino)propyl, 2-(2-methylimidazol-1-yl)ethyl, 3-(2-methylimidazol-1-yl)propyl, 2-(5-methyl-1,2,4-triazol-1-yl)ethyl, 3-(5-methyl-1,2,4-triazol-1-yl)propyl, 3-(imidazol-1-yl)propyl, 3-(1,2,3-triazol-1-yl)propyl, 3-(1,2,3-triazol-2-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy) ethyl, 2-(4-methylpiperazin-1-yl)ethyl, 3-(4-methylpiperazin-1-yl)propyl, 3-(methylsulphinyl)propyl and 3-(methylsulphonyl)propyl.

Especially $R^{5c}$ represents methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino) propyl, 2-methylthiazol-4-ylmethyl, 2-acetamidothiazol-4-ylmethyl, 1-methylimidazol-2-ylmethyl, 2-(imidazol-1-yl)ethyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, benzyl, 2-(4-pyridyloxy)ethyl, 2-(4-pyridylamino)ethyl or 2-(4-oxo-1,4-dihydro 1-pyridyl)ethyl, and an additional value for $R^{5c}$ is 3-(3-pyridyl)propyl.

More especially $R^{5c}$ represents methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl) ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino) propyl, 2-methylthiazol-4-ylmethyl, 2-acetamidothiazol-4-ylmethyl, 1-methylimidazol-2-ylmethyl, 2-(imidazol-1-yl) ethyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, benzyl, 2-(4-pyridyloxy)ethyl, 2-(4-pyridylamino)ethyl or 2-(4-oxo-1,4-dihydro-1-pyridyl)ethyl.

The present invention also provides compounds of the formula Id:

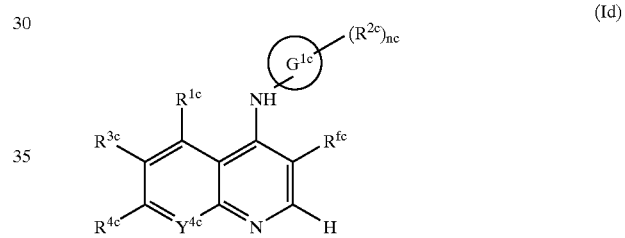

(Id)

(wherein $R^{fc}$, $R^{1c}$, $R^{2c}$, $R^{3c}$, $R^{4c}$, $Y^{4c}$, $G^{1c}$ and nc are as defined hereinbefore with the proviso that where $R^{4c}$ is chlorine at least one $R^{2c}$ is hydroxy), and salts thereof.

Thus where $R^{4c}$ is chlorine the moiety IId:

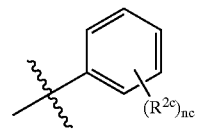

(IId)

may represent any substituted phenyl group within the definitions of $R^{2c}$ and nc as defined hereinbefore for formula I, provided that the phenyl moiety carries at least one hydroxy substituent.

Advantageously $R^{4c}$ is other than chlorine, preferably other than halogeno and especially other than hydrogen, halogeno or $C_{1-3}$alkyl.

Preferably $R^{4c}$ is a group $R^{5c}$—$X^{1c}$— wherein $R^{5c}$ and $X^{1c}$ are as defined hereinbefore with the proviso that $R^{5c}$ is other than an unsubstituted $C_{1-5}$alkyl group and other than a $C_{1-5}$alkyl group substituted with one or more fluorine atoms.

Preferred compounds are:
4-(4-chloro-2-fluoroanilino)-6-methoxy-7-(3-pyrrolidin-1-ylpropoxy)quinoline,
4-(4-chloro-2-fluoroanilino)-7-(3-(dimethylamino) propoxy)-6-methoxyquinoline, 6,7-dimethoxy-4-(3-hydroxy-4-methylanilino)quinoline, 4-(4-chloro-2-fluoroanilino)-6-methoxy-7-(2-([1,2,4]-triazol-1-yl)ethoxy)quinoline, 4-(4-bromo-2-fluoro-5-hydroxyanilino)-7-chloroquinoline, 7-chloro-4-(4-chloro-2-fluoro-5-hydroxyanilino)quinoline, 6,7-dimethoxy-4-(3-hydroxyanilino)quinoline, 4-(4-chloro-2-fluorophenoxy)-6,7-dimethoxyquinoline, 4-(4-chloro-2-fluoroanilino)-7-(3-hydroxypropoxy)-6-methoxyquinoline, 4-(4-chloro-2-fluoroanilino)-7-methoxy-6-(3-morpholinopropoxy)quinoline, 7-benzyloxy-4-(3-hydroxy-4-methylanilino)-6-methoxyquinoline and 4-(4-chloro-2-fluoroanilino)-7-methoxy-6-(N-[3-morpholinopropyl]carbamoyl)quinoline and salts thereof, particularly hydrochloride salts thereof.

More preferred compounds are:

4-(2-fluoro-5-hydroxy-4-methylanilino)-7-methoxy-6-methoxycarbonylquinoline, 4-(2-fluoro-5-hydroxy-4-methylphenoxy)-6-methoxy-7-(3-morpholinopropoxy)quinoline, 6-cyano-4-(2-fluoro-5-hydroxy-4-methylanilino)-7-(2-methoxyethoxy)quinoline, 6,7dimethoxy-4-(2-fluoro-5-hydroxy-4-methylphenoxy)quinoline, 4-(4-chloro-2-fluoro-5-hydroxyanilino)-6-methoxy-7-(2-methoxyethoxy)quinoline, 6,7-dimethoxy-3-fluoro-4-(4-chloro-2-fluoro-5-hydroxyanilino)quinoline, 4-(4-chloro-2-fluoro-5-hydroxyanilino)-7-ethoxy-6-methoxyquinoline, 4-(4-chloro-2-fluoro-5-hydroxyanilino)-6-methoxy-7-(3-(3-pyridyl)propoxy)quinoline, 6,7-dimethoxy-4-(2-fluoro-5-hydroxy-4-methylanilino)quinoline, 4-(4-chloro-2-fluoro-5-hydroxyanilino)-6-methoxy-7-(2-methylthiazol-4-ylmethoxy)quinoline, 4-(2-fluoro-5-hydroxy-4-methylanilino)-6-methoxy-7-(2-methoxyethoxy)quinoline, 4-(4-chloro-2-fluoro-5-hydroxyanilino)-6-methoxy-7-(3-pyrrolidin-1-ylpropoxy)quinoline, 4-(2-fluoro-5-hydroxy-4-methylanilino)-6-methoxy-7-(3-pyrrolidin-1-ylpropoxy)quinoline, 4-(3-hydroxy-4-methylanilino)-6-methoxy-7-(2-methoxyethoxy)quinoline, 6-cyano-4-(2-fluoro-5-hydroxy-4-methylanilino)-7-(3-morpholinopropoxy)quinoline, 4-(4-chloro-2-fluoro-5-hydroxyanilino)-6-methoxy-7-(3-morpholinopropoxy)quinoline, 4-(2-fluoro-5-hydroxy-4-methylanilino)-6-methoxy-7-(3-morpholinopropoxy)quinoline, 4-(4-chloro-2-fluoro-5-hydroxyanilino)-6-methoxy-7-(4-pyridylmethoxy)quinoline, 4-(4-chloro-2-fluoro-5-hvdroxyanilino)-6-methoxy-7-(2-morpholinoethoxy)quinoline, 6-cyano-4-(2-fluoro-5-hydroxy-4-methylanilino)-7-methoxyquinoline, 7-chloro-4-(2-fluoro-5-hydroxy-4-methylanilino)quinoline and 4-(4-chloro-2-fluoroanilino)-7-(2-hydroxyethoxy)-6-methoxyquinoline and salts thereof, particularly hydrochloride salts thereof.

Especially preferred compounds are:

6-cyano-4-(3-hydroxy-4-methylanilino)-7-(2-methoxyethoxy)quinoline, 4-(4-chloro-2-fluoro-5-hydroxyanilino)-6,7-dimethoxyquinoline, 7-benzyloxy-4-(4-chloro-2-fluoro-5-hydroxyanilino)-6-methoxyquinoline, 6-cyano-4-(2-fluoro-5-hydroxy-4-methylphenoxy)-7-(2-methoxyethoxy)quinoline, 7-benzyloxy-4-(4-bromo-2-fluoro-5-hydroxyanilino)-6-methoxyquinoline 4-(4-bromo-2-fluoro-5-hydroxyanilino)-6,7-dimethoxyquinoline, 4-(4-chloro-2-fluoro-5-hydroxyanilino)-6-methoxy-7-(1-methylimidazol-2-ylmethoxy)quinoline, 4-(4-chloro-2-fluoroanilino)-6-cyano-7-(2-methoxyethoxy)quinoline, 4-(4-chloro-2-fluoroanilino)-6-cyano-7-(3-morpholinopropoxy)quinoline, 4-(4-chloro-2-fluoroanilino)-6-methoxy-7-(2-methoxyethoxy)quinoline and 4-(4-chloro-2-fluoroanilino)-6-methoxy-7-(3-morpholinopropoxy)quinoline and salts thereof, particularly hydrochloride salts thereof.

In a particular aspect of the present invention preferred compounds are:

6-cyano-4-(2-fluoro-5-hydroxy-4-methylanilino)-7-(2-methoxyethoxy)quinoline, 4-(4-chloro-2-fluoro-5-hydroxyanilino)-6,7-dimethoxyquinoline, 4-(2-fluoro-5-hydroxy-4-methylphenoxy)-6-methoxy-7-(3-morpholinopropoxy)quinoline, 6-cyano-4-(2-fluoro-5-hydroxy-4-methylphenoxy)-7-(2-methoxyethoxy)quinoline, 4-(3-hydroxy-4-methylanilino)-6-methoxy-7-(2-methoxyethoxy)quinoline, 7-benzyloxy-4-(3-hydroxy-4-methylanilino)-6-methoxyquinoline, 4-(27fluoro-5-hydroxy-4-methylanilino)-6-methoxy-7-(3-morpholinopropoxy)quinoline, 4-(2-fluoro-5-hydroxy-4-methylphenoxy)-6,7-dimethoxyquinoline, and salts thereof, particularly hydrochloride salts thereof.

For the avoidance of doubt it is to be understood that where in this specification a group is described as defined hereinbefore this encompasses the first occurring and broadest definition as well as each and all of the preferred definitions for that group. For example, for compounds of formula I, n is defined as an integer from 0 to 5 but n is preferably an integer from 1 to 3, more preferably 2 or 3. Thus references in the specification to n as being "defined hereinbefore" are to be understood as references to not only the broadest prior definition of n, but also to incorporate the stated preferences for the definition of n.

In this specification unless stated otherwise the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1–6 carbon atoms, preferably 1–4 carbon atoms.

The term "alkoxy" as used herein, unless stated otherwise includes "alkyl"—O— groups in which "alkyl" is as hereinbefore defined. The term "aryl" as used herein unless stated otherwise includes reference to a Case aryl group which may, if desired, carry one or more substituents selected from halogeno, alkyl, alkoxy, nitro, trifluoromethyl and cyano, (wherein alkyl and alkoxy are as hereinbefore defined). The term "aryloxy" as used herein unless otherwise stated includes "aryl"—O—groups in which "aryl" is as hereinbefore defined. The term "sulphonyloxy" as used herein refers to alkylsulphonyloxy and arylsulphonyloxy groups in which "alkyl" and "aryl" are as hereinbefore defined. The term "alkanoyl" as used herein unless otherwise stated includes alkylC=O groups in which "alkyl" is as defined hereinbefore, for example ethanoyl refers to $CH_3C=O$. In this specification unless stated otherwise the term "alkenyl" includes both straight and branched chain alkenyl groups but references to individual alkenyl groups such as 2-butenyl are specific for the straight chain version only. Unless otherwise stated the term "alkenyl" advantageously refers to chains with 2–6 carbon atoms, preferably 4–5 carbon atoms. In this specification unless stated otherwise the term "alkynyl" includes both straight and branched chain alkynyl groups but references to individual alkynyl groups such as 2-butynyl are specific for the straight chain version only.

Unless otherwise stated the term "alkynyl" advantageously refers to chains with 2–6 carbon atoms, preferably 4–5 carbon atoms.

Within the present invention it is to be understood that a compound of the formula I or a salt thereof may exhibit the phenomenon of tautomerism and that the formulae drawings within this specification can represent only one of the possible tautomeric forms. It is to be understood that the invention encompasses any tautomeric form which inhibits VEGF receptor tyrosine kinase activity and is not to be limited merely to any one tautomeric form utilised within the formulae drawings.

It is also to be understood that certain compounds of the formula I and salts thereof can exist in solvated as well as unsolvated forms such as, for example, hydrated forms. It is to be understood that the invention encompasses all such solvated forms which inhibit VEGF receptor tyrosine kinase activity.

For the avoidance of any doubt, it is to be understood that when $X^1$ is, for example, a group of formula —$NR^7CO$—, it is the nitrogen atom bearing the $R^7$ group which is attached to the heterocyclic/quinoline ring and the carbonyl (CO) group is attached to $R^6$, whereas when $X^1$ is, for example, a group of formula —$CONR^8$—, it is the carbonyl group which is attached to the heterocyclic/quinoline ring and the nitrogen atom bearing the $R^8$ group is attached to $R^6$.

A similar convention applies to the other two atom $X^1$ linking groups such as —$NR^{10}SO_2$—, and —$SO_2NR^9$—. When $X^1$ is —$NR^{11}$— it is the nitrogen atom bearing the $R^{11}$ group which is linked to the heterocyclic/quinoline ring and to $R^6$. When $X^1$ is —OCO— it is the carbonyl group which is is attached to the heterocyclic/quinoline ring and the oxy group is attached to $R^6$. Analogous conventions apply to groups $X^{2-10}$. It is further to be understood that when $X^2$ represents —$NR^{13}$— and $R^{13}$ is $C_{1-3}$alkoxy$C_{2-3}$alkyl it is the $C_{2-3}$alkyl moiety which is linked to the nitrogen atom of $X^2$ and an analogous convention applies to other groups.

For the avoidance of any doubt, it is to be understood that when $R^{30}$ carries a $C_{1-4}$aminoalkyl substituent it is the $C_{1-4}$alkyl moiety which is attached to $R^{30}$ whereas when $R^{30}$ carries a $C_{1-4}$alkylamino substituent it is the amino moiety which is attached to $R^{30}$ and an analogous convention applies to other groups.

The present invention relates to the use of the compounds of formula I as hereinbefore defined as well as to the salts thereof. Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid) or with sulphuric or phosphoric acid, or with trifluoroacetic, citric or maleic acid. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

A compound of the formula Id, or salt thereof, and other compounds of the invention (as hereinafter defined) may be prepared by any process known to be applicable to the preparation of chemically-related compounds. Such processes include, for example, those illustrated in European Patent Application, Publication No. 0326330 and U.S. Pat. No. 3,936,461. Such processes, are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus the following processes (a) to (f) and (i) to (vi) constitute further features of the present invention.

Synthesis of Compounds of Formula I (a) Compounds of the formula I and salts thereof may be prepared by the reaction of a compound of the formula III:

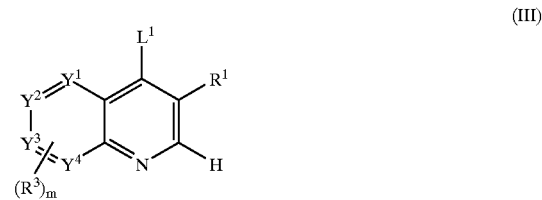

(III)

(wherein $R^1$, $R^3$, $Y^1$, $Y^2$, $Y^3$, $Y^4$ and m are as defined hereinbefore and $L^1$ is a displaceable moiety), with a compound of the formula IV:

(IV)

(wherein $G^1$, $R^2$ and n are as defined hereinbefore) whereby to obtain compounds of the formula I and salts thereof. A convenient displaceable moiety L¹ is, for example, a halogeno, alkoxy (preferably $C_{1-4}$alkoxy), aryloxy or sulphonyloxy group, or an alkylthio group, for example a chloro, bromo, methoxy, phenoxy, methanesulphonyloxy or toluene-4-sulphonyloxy group, or a methylthio group.

The reaction is advantageously effected in the presence of either an acid or a base. Such an acid is, for example, an anhydrous inorganic acid such as hydrogen chloride. Such a base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or for example, an alkali metal or alkaline earth metal carbonate or hydroxide, for example sodium carbonate, potassium carbonate, calcium carbonate, sodium hydroxide or potassium hydroxide. Alternatively such a base is, for example, an alkali metal hydride, for example sodium hydride, or an alkali metal or alkaline earth metal amide, for example sodium amide or sodium bis(trimethylsilyl)amide. The reaction is preferably effected in the presence of an inert solvent or diluent, for example an alkanol or ester such as methanol, ethanol, isopropanol or ethyl acetate, a halogenated solvent such as methylene chloride, trichloromethane or carbon tetrachloride, an ether such as tetrahydrofuran or 1,4-dioxan, an aromatic hydrocarbon solvent such as toluene, or a dipolar aprotic solvent such as N,N-dimethylformamide, N,N-dimethylacetamide, N-methylpyrrolidin-2-one or dimethylsulphoxide. The reaction is conveniently effected at a temperature in the range, for example, 10 to 150° C., preferably in the range 40 to 120° C.

The compound of the invention may be obtained from this process in the form of the free base or alternatively it may be obtained in the form of a salt with the acid of the formula H—L¹ wherein L¹ has the meaning defined hereinbefore. When it is desired to obtain the free base from the salt, the salt may be treated with a base as defined hereinbefore using a conventional procedure.

(b) Where the group of formula II:

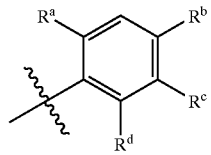

(II)

(wherein $R^a$, $R^b$, $R^c$ and $R^d$ are as defined hereinbefore) represents a phenyl group carrying one or more hydroxy groups, a compound of the formula I and salts thereof can be prepared by the deprotection of a compound of formula V:

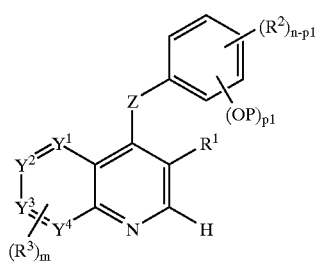

(V)

(wherein n, $Y^1$, $Y^2$, $Y^3$, $Y^4$, $R^1$, $R^2$, $R^3$, m and Z are as hereinbefore defined, P represents a phenolic hydroxy protecting group and p1 is an integer from 1 to 5 equal to the number of protected hydroxy groups and such that n-p1 is equal to the number of $R^2$ substituents which are not protected hydroxy). The choice of phenolic hydroxy protecting group P is within the standard knowledge of an organic chemist, for example those included in standard texts such as "Protective Groups in Organic Synthesis" T. W. Greene and R. G. M. Wuts, 2nd Ed. Wiley 1991, including ethers (for example, methyl, methoxymethyl, allyl and benzyl), silyl ethers (for example, t-butyldiphenylsilyl and t-butyldimethylsilyl), esters (for example, acetate and benzoate) and carbonates (for example, methyl and benzyl). The removal of such a phenolic hydroxy protecting group may be effected by any of the procedures known for such a transformation, including those reaction conditions indicated in standard texts such as that indicated hereinbefore, or by a related procedure. The reaction conditions preferably being such that the hydroxy derivative is produced without unwanted reaction at other sites within the starting or product compounds. For example, where the protecting group P is acetate, the transformation may conveniently be effected by treatment of the quinoline derivative with a base as defined hereinbefore and including ammonia, and its mono and di-alkylated derivatives, preferably in the presence of a protic solvent or co-solvent such as water or an alcohol, for example methanol or ethanol. Such a reaction can be effected in the presence of an additional inert solvent or diluent as defined hereinbefore and at a temperature in the range 0 to 50° C., conveniently at about 20° C.

(c) Production of those compounds of formula I and salts thereof wherein a substituent $R^3$ is $R^6$—$X^1$— and wherein $X^1$ is —O—, —S— or —NR¹¹— can be achieved by the reaction, conveniently in the presence of a base as defined hereinbefore, of a compound of the formula VI:

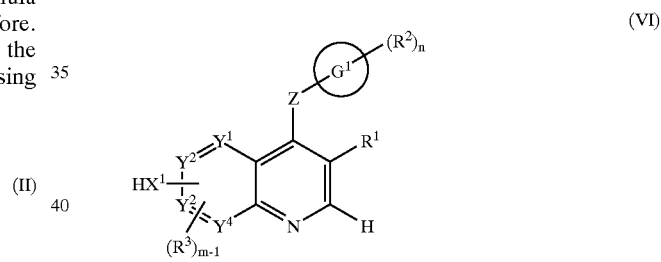

(VI)

(wherein n, $X^1$, $Y^1$, $Y^2$, $Y^3$, $Y^4$, $G^1$, $R^1$, $R^2$, $R^3$, Z and m are as hereinbefore defined) with a compound of formula VII:

$R^6$—L¹ (VII)

(wherein $R^6$ and L¹ are as hereinbefore defined); L¹ is a displaceable moiety for example a halogeno or sulphonyloxy group such as a bromo or methanesulphonyloxy group. The reaction is preferably effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 50° C.

(d) Compounds of the formula I and salts thereof wherein a substituent $R^3$ is $R^6$—$X^1$— and wherein $R^6$ is $C_{1-5}$alkyl$R^{61}$, [wherein $R^{61}$ is selected from one of the following two groups:

1) $X^{11}R^{17}$ (wherein $X^{11}$ represents —O—, —S—, —SO$_2$—, —NR$^{62}$CO—, —NR$^{63}$SO$_2$— or —NR$^{64}$— (wherein $R^{62}$, $R^{63}$ and $R^{64}$, each independently represents hydrogen, $C_{1-3}$alkyl or $C_{1-3}$alkoxy$C_{2-3}$alkyl) and $R^{17}$ is as defined hereinbefore); and 2) $X^{12}C_{1-5}$alkyl$X^5R^{23}$ (wherein $X^{12}$ represents —O—, —S—, —SO$_2$—, —NR$^{65}$CO—, —NR$^{66}$SO$_2$— or —NR$^{67}$— (wherein R$^{65}$, R$^{66}$ and R$^{67}$, each independently represents hydrogen, C$_{1-3}$alkyl or C$_{1-3}$alkoxyC$_{2-3}$alkyl) and X$^5$ and R$^{23}$ are as defined hereinbefore);] may be prepared by reacting a compound of the formula VIII:

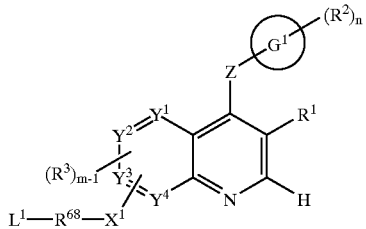

(VIII)

(wherein L$^1$, X$^1$, G$^1$, Y$^1$, Y$^2$, Y$^3$, Y$^4$, R$^1$, R$^2$, R$^3$, Z, m and n are as hereinbefore defined and R$^{68}$ is C$_{1-5}$alkyl) with a compound of the formula IX:

R$^{61}$—H  (IX)

(wherein R$^{61}$ is as defined hereinbefore) to give a compound of the formula I. The reaction may conveniently be effected in the presence of a base (as defined hereinbefore in process (a)) and advantageously in the presence of an inert solvent or diluent (as defined hereinbefore in process (a)), and at a temperature in the range, for example 0 to 150° C., conveniently at about 50° C.

Compounds of the formula I wherein a substituent R$^3$ is R$^6$—X$^1$— and wherein R$^6$ is C$_{2-5}$alkylR$^{59}$, (wherein R$^{59}$ is as defined hereinbefore), may be prepared by reacting a compound of formula VIII (wherein R$^{61}$ is C$_{1-5}$alkyl) with a compound of the formula IXa:

R$^{59}$—H  (IXa)

(wherein R$^{59}$ is as defined hereinbefore) to give a compound of the formula I. The reaction may conveniently be effected in the presence of a base (as defined hereinbefore in process (a)) and advantageously in the presence of an inert solvent or diluent (as defined hereinbefore in process (a)), and at a temperature in the range, for example 0 to 150° C., conveniently at about 50° C.

(e) The production of those compounds of the formula I and salts thereof wherein a substituent R$^3$ is represented by —NR$^4$R$^5$, where one or both of R$^4$ and R$^5$ are C$_{1-3}$alkyl, may be effected by the reaction of compounds of formula I wherein the substituent R$^3$ is an amino group and an alkylating agent, preferably in the presence of a base as defined hereinbefore. Such alkylating agents are C$_{1-3}$alkyl moieties bearing a displaceable moiety as defined hereinbefore such as C$_{1-3}$alkyl halides for example C$_{1-3}$alkyl chloride, bromide or iodide. The reaction is preferably effected in the presence of an inert solvent or diluent (as defined hereinbefore in process (a)) and at a temperature in the range, for example, 10 to 100° C., conveniently at about ambient temperature.

(f) The production of compounds of formula I and salts thereof wherein one or more of the substituents R$^2$ and R$^3$ is an amino group may be effected by the reduction of a corresponding compound of formula I wherein the substituent(s) at the corresponding position(s) of the heterocyclic/quinoline and/or heterocyclic/phenyl ring is/are a nitro group(s). The reduction of the nitro group(s) may conveniently be effected by any of the procedures known for such a transformation. The reduction may be carried out, for example, by the hydrogenation of a solution of the nitro compound in the presence of an inert solvent or diluent as defined hereinbefore in the presence of a metal effective to catalyse hydrogenation reactions such as palladium or platinum. A further reducing agent is, for example, an activated metal such as activated iron (produced for example by washing iron powder with a dilute solution of an acid such as hydrochloric acid). Thus, for example, the reduction may be effected by heating the nitro compound and the activated metal in the presence of a solvent or diluent such as a mixture of water and alcohol, for example methanol or ethanol, to a temperature in the range, for example 50 to 150° C., conveniently at about 70° C. The production of a compound of formula I and salts thereof wherein the substituent(s) at the corresponding position(s) of the heterocyclic/quinoline and/or heterocyclic/phenyl ring is/are a nitro group(s) may be effected by the processes described hereinbefore and hereinafter in processes (a–d) and (i–vi) using a compound selected from the compounds of the formulae (I–XXIII) in which the substituent(s) at the corresponding position(s) of the heterocyclic/quinoline and/or heterocyclic/phenyl ring is/are a nitro group(s).

Synthesis of Intermediates (i) Such compounds of formula III and salts thereof in which L$^1$ is halogeno may for example be prepared by halogenating a compound of the formula X:

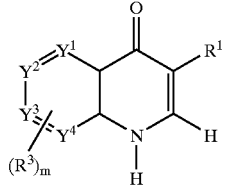

(X)

(wherein m, R$^1$, R$^3$, Y$^1$, Y$^2$, Y$^3$ and Y$^4$ are as hereinbefore defined).

Convenient halogenating agents include inorganic acid halides, for example thionyl chloride, phosphorus(III) chloride, phosphorus(V)oxychloride and phosphorus(V) chloride. The halogenation reaction is conveniently effected in the presence of an inert solvent or diluent such as for example a halogenated solvent such as methylene chloride, trichloromethane or carbon tetrachloride, or an aromatic hydrocarbon solvent such as benzene or toluene. The reaction is conveniently effected at a temperature in the range, for example 10 to 150° C., preferably in the range 40 to 100° C.

The compounds of formula X and salts thereof wherein one or more of Y$^1$, Y$^2$, Y$^3$ and Y$^4$ are nitrogen, may for example, be prepared by any of the known procedures for making azaquinolones, such as procedures analogous to those described in "Comprehensive Heterocyclic Chemistry" Volume 2, Naphthyridine Chemistry, Katritsky and Rees, 1984; DE 2423650; Cubza, Synthesis 1974, 809; Barlin et al., Aust. J. Chem. 1984, 37 1065; WO 9313097 A1; WO 9500511 A1; Hirao et al., Bull. Chem. Soc. Jpn. 1973, 46, 1826; Carboni et al., Gazz. Chim. Ital. 1972, 102, 253 and 264; Carboni et al., Gazz Chim. Ital. 1971, 101, 129 and 133 and 137; Bowie J. Chem. Soc. Perk Trans I, 1972, 1106; Brown J. Org Chem. 1965, 30, 1607; Quequiner et al., Can. J. Chem. 1992, 70, 2828; Reynolds et al., J. Chem. Soc. Perk Trans II, 1988, 4, 551; Nagai et al JP 51054596; Sato et al JP 51054593.

The compounds of formula X and salts thereof may for example be prepared by reacting a compound of the formula XI:

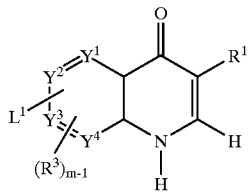
(XI)

with a compound of the formula XII:

R⁶—X¹—H  (XII)

(wherein $R^1$, $R^3$, m, $Y^1$, $Y^2$, $Y^3$, $Y^4$, $L^1$, $R^6$ and $X^1$ are as hereinbefore defined). The reaction may conveniently be effected the presence of a base (as defined hereinbefore in process (a)) and advantageously in the presence of an inert solvent or diluent (as defined hereinbefore in process (a)), advantageously at a temperature in the range, for example 10 to 200° C., preferably in the range 100 to 150° C.

The compounds of formula X and salts thereof may also be prepared by cyclising a compound of the formula XIII:

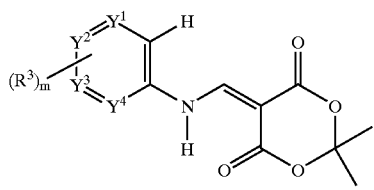
(XIII)

(wherein $Y^1$, $Y^2$, $Y^3$, $Y^4$, $R^3$ and m are as hereinbefore defined,) whereby to form a compound of formula X or salt thereof. The cyclisation may be effected by heating a compound of the formula XIII in the presence of an inert solvent or diluent such as an ether, for example diphenyl ether, at an elevated temperature, preferably in the range 200 to 300° C.

Compounds of formula XIII may for example be prepared by reacting a compound of the formula XIV:

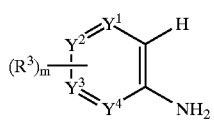
(XIV)

with a compound of the formula XV:

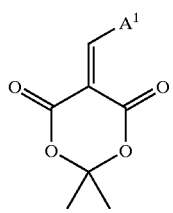
(XV)

(wherein $Y^1$, $Y^2$, $Y^3$, $Y^4$, $R^3$ and m are as hereinbefore defined and $A^1$ is an alkoxy (preferably $C_{1-4}$alkoxy) group). The reaction may conveniently be effected in the presence of an alcohol as solvent, such as ethanol and advantageously at a temperature in the range for example 20 to 100° C., preferably in the range 50 to 100° C.

The compounds of formula III and salts thereof may also be prepared for example by reacting a compound of the formula XVI:

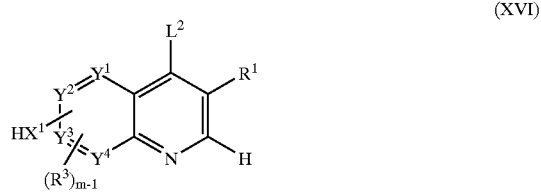
(XVI)

(wherein $Y^1$, $Y^2$, $Y^3$, $Y^4$, $R^1$, $R^3$, m and $X^1$ are as hereinbefore defined, with the proviso that $X^1$ is not —CH₂—, and $L^2$ represents a displaceable protecting moiety) with a compound of the formula VII as hereinbefore defined, whereby to obtain a compound of formula III in which $L^1$ is represented by $L^2$.

A compound of formula XVI is conveniently used in which $L^2$ represents a chloro group or a phenoxy group which may if desired carry up to 5 substituents, preferably up to 2 substituents, selected from halogeno, nitro and cyano. The reaction may be conveniently effected under conditions as described for process (c) hereinbefore.

The compounds of formula XVI and salts thereof as hereinbefore defined may for example be prepared by deprotecting a compound of the formula XVII:

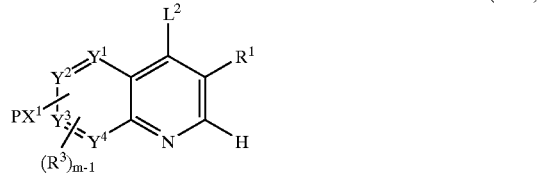
(XVII)

(wherein $R^1$, $R^3$, m, $Y^1$, $Y^2$, $Y^3$, $Y^4$, P, $X^1$ and $L^2$ are as hereinbefore defined). Deprotection may be effected by techniques well known in the literature, for example where P represents a benzyl group deprotection may be effected by hydrogenolysis or by treatment with trifluoroacetic acid.

One compound of formula III may if desired be converted into another compound of formula III in which the moiety $L^1$ is different. Thus for example a compound of formula III in which $L^1$ is other than halogeno, for example optionally substituted phenoxy, may be converted to a compound of formula III in which $L^1$ is halogeno by hydrolysis of a compound of formula III (in which $L^1$ is other than halogeno) to yield a compound of formula X as hereinbefore defined, followed by introduction of halide to the compound of formula X, thus obtained as hereinbefore defined, to yield a compound of formula III in which $L^1$ represents halogeno.

(ii) The compounds of formula V and salts thereof, constitute a further feature of the present invention, and may for example be prepared by the reaction of a compound of formula III as hereinbefore defined with a compound of the formula XVIII:

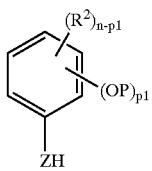

(XVIII)

(wherein $R^2$, n, Z, p1 and P are as hereinbefore defined). The reaction may for example be effected as described for process (a) hereinbefore.

The compounds of formula V and salts thereof may also be prepared by reacting a compound of formula XIX:

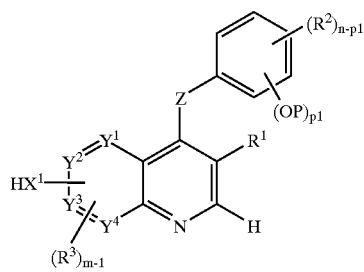

(XIX)

(wherein $R^1$, $R^2$, $R^3$, Z, $X^1$, $Y^1$, $Y^2$, $Y^3$, $Y^4$, P, p1, m and n are as hereinbefore defined with the proviso that $X^1$ is not —$CH_2$—) with a compound of the formula VII as hereinbefore defined. The reaction may for example be effected as described for process (c) hereinbefore.

Compounds of the formula XIX and salts thereof constitute another feature of the present invention and may be made by reacting compounds of the formulae XVII and XVIII as hereinbefore defined, under conditions described in (a) hereinbefore, to give a compound of formula XX:

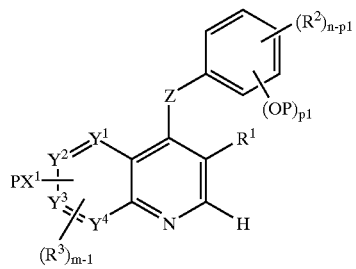

(XX)

(wherein $R^1$, $R^2$, $R^3$, Z, $Y^1$, $Y^2$, $Y^3$, $Y^4$, P, $X^1$, m, p1 and n are as hereinbefore defined) and then deprotecting the compound of formula XX for example as described in (i) above. Compounds of the formula XX as hereinbefore defined and salts thereof constitute a further feature of the present invention.

(iii) Compounds of the formula VI as hereinbefore defined and salts thereof constitute a further feature of the present invention and may be made by deprotecting the compound of formula XXI:

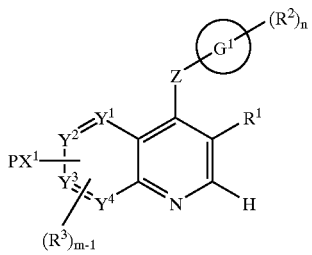

(XXI)

(wherein $R^1$, $R^2$, $R^3$, Z, $Y^1$, $Y^2$, $Y^3$, Y4, $G^1$, P, $X^1$, m and n are as hereinbefore defined) by a process for example as described in (i) above.

Compounds of the formula XXI and salts thereof may be made by reacting compounds of the formulae XVII and IV as hereinbefore defined, under the conditions described in (a) hereinbefore, to give a compound of the formula XXI or salt thereof.

(iv) Compounds of the formula VIII as defined hereinbefore and salts thereof constitute a further feature of the present invention and may for example be made by the reaction of a compound of formula VI as defined hereinbefore with a compound of the formula XXII:

$$L^1—R^{68}—L^1 \quad \text{(XXII)}$$

(wherein $L^1$ and $R^{68}$ are as hereinbefore defined) to give a compound of the formula VIII. The reaction may be effected for example by a process as described in (c) above.

Compounds of the formula VIII and salts thereof may also be made for example by deprotecting a compound of the formula XXIII:

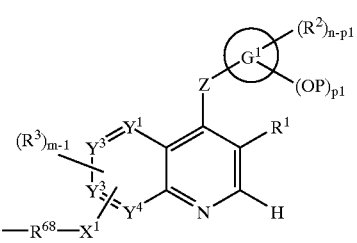

(XXIII)

(wherein $L^1$, $R^{68}$, $X^1$, $R^1$, $R^2$, $R^3$, Z, $Y^1$, $Y^2$, $Y^3$, $Y^4$, $G^1$, P, m, n and p1 are as defined hereinbefore) by a process for example as described in (b) above.

Compounds of the formula XXIII as hereinbefore defined and salts thereof constitute a further feature of the present invention and may be made for example by reacting compounds of the formulae XIX and XXII as defined hereinbefore, under the conditions described in (c) above.

(v) Compounds of the formula IV may be prepared by any known procedure for making substituted phenyl or substituted or unsubstituted heteroaromatic groups. In particular aminoindazoles may be made according to methods analogous to those described in Cockerill et al. WO 970369 Al. Davies, J. Chem. Soc., 1955, 2412–2418; Pernot et al., Bull. Soc. Chim. France, 1958, 152,156; Pfannstiel et al., Chem. Bericht., 1942, 75, 1096; U.S. Pat. No. 2,787,515, 1955; CH 543515, 1973; Boyer et al., J. Chem. Res. miniprint 1990, 11, 3601; Boyer et al., Heterocycles 1995, 41, 487.

(vi) Compounds of the formula I and salts thereof wherein $R^1$ is fluoro, may be prepared by an analogous procedure to that described in Example 14.

When a pharmaceutically acceptable salt of a compound of the formula Id is required, it may be obtained, for example, by reaction of said compound with, for example, an acid using a conventional procedure, the acid having a pharmaceutically acceptable anion.

Many of the intermediates defined herein are novel, for example, those of the formulae V, VI, VIII, XIX, XX and XXIII and these are provided as a further feature of the invention.

Intermediates of the formulae III, X and XXI are also provided as a further feature of the invention.

The identification of compounds which potently inhibit the tyrosine kinase activity associated with the VEGF receptors such as Flt and/or KDR and which inhibit angiogenesis and/or increased vascular permeability is desirable and is the subject of the present invention. These properties may be assessed, for example, using one or more of the procedures set out below:

(a) In Vitro Recepor Tyrosine Kinase Inhibition Test

This assay determines the ability of a test compound to inhibit tyrosine kinase activity. DNA encoding VEGF or epidermal growth factor (EGF) receptor cytoplasmic domains may be obtained by total gene synthesis (Edwards M, International Biotechnology Lab 5(3), 19–25, 1987) or by cloning. These may then be expressed in a suitable expression system to obtain polypeptide with tyrosine kinase activity. For example VEGF and EGF receptor cytoplasmic domains, which were obtained by expression of recombinant protein in insect cells, were found to display intrinsic tyrosine kinase activity. In the case of the VEGF receptor Flt (Genbank accession number X51602), a 1.7 kb DNA fragment encoding most of the cytoplasmic domain, commencing with methionine 783 and including the termination codon, described by Shibuya et al (Oncogene, 1990, 5: 519–524), was isolated from cDNA and cloned into a baculovirus transplacement vector (for example pAcYM1 (see The Baculovirus Expression System: A Laboratory Guide, L. A. King and R. D. Possee, Chapman and Hall, 1992) or pAc360 or pBlueBacHis (available from Invitrogen Corporation)). This recombinant construct was co-transfected into insect cells (for example Spodoptera frugiperda 21(Sf21)) with viral DNA (eg Pharmingen BaculoGold) to prepare recombinant baculovirus. (Details of the methods for the assembly of recombinant DNA molecules and the preparation and use of recombinant baculovirus can be found in standard texts for example Sambrook et al, 1989, Molecular cloning—A Laboratory Manual, 2nd edition. Cold Spring Harbour Laboratory Press and O'Reilly et al, 1992, Baculovirus Expression Vectors—A Laboratory Manual, W. H. Freeman and Co, New York). For other tyrosine kinases for use in assays, cytoplasmic fragments starting from methionine 806 (KDR, Genbank accession number L04947) and methionine 668 (EGF receptor, Genbank accession number $X^{00588}$) may be cloned and expressed in a similar manner.

For expression of cFlt tyrosine kinase activity, Sf21 cells were infected with plaque-pure cFlt recombinant virus at a multiplicity of infection of 3 and harvested 48 hours later. Harvested cells were washed with ice cold phosphate buffered saline solution (PBS) (10 mM sodium phosphate pH7.4, 138 mM sodium chloride, 2.7 mM potassium chloride) then resuspended in ice cold HNTG/PMSF (20 mM Hepes pH7.5, 150 mM sodium chloride, 10% v/v glycerol, 1% v/v Triton X100, 1.5 mM magnesium chloride, 1 mM ethylene glycol-bis(βaminoethyl ether) N,N,N',N'-tetraacetic acid (EGTA), 1 mM PMSF (phenylmethylsulphnyl fluoride); the PMSF is added just before use from a freshly-prepared 100 mM solution in methanol) using 1 ml HNTG/PMSF per 10 million cells. The suspension was centrifuged for 10 minutes at 13,000 rpm at 4° C., the supernatant (enzyme stock) was removed and stored in aliquots at −70° C. Each new batch of stock enzyme was titrated in the assay by dilution with enzyme diluent (100 mM Hepes pH 7.4, 0.2 mM sodium orthovanadate, 0.1% v/v Triton X100, 0.2 mM dithiothreitol). For a typical batch, stock enzyme is diluted 1 in 2000 with enzyme diluent and 50 μl of dilute enzyme is used for each assay well.

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100μl of diluted substrate solution was dispensed into all wells of assay plates (Nunc maxisorp 96-well immunoplates) which were sealed and left overnight at 4° C.

On the day of the assay the substrate solution was discarded and the assay plate wells were washed once with PBST (PBS containing 0.05% v/v Tween 20) and once with 50 mM Hepes pH7.4.

Test compounds were diluted with 10% dimethylsulphoxide (DMSO) and 25μl of diluted compound was transferred to wells in the washed assay plates. "Total" control wells contained 10% DMSO instead of compound. Twenty five microlitres of 40 mM manganese(II)chloride containing 8 μM adenosine-5'-triphosphate (ATP) was added to all test wells except "blank" control wells which contained manganese(II)chloride without ATP. To start the reactions 50 μl of freshly diluted enzyme was added to each well and the plates were incubated at room temperature for 20 minutes. The liquid was then discarded and the wells were washed twice with PBST. One hundred microlitres of mouse IgG anti-phosphotyrosine antibody (Upstate Biotechnology Inc. product 05–321), diluted 1 in 6000 with PBST containing 0.5% w/v bovine serum albumin (BSA), was added to each well and the plates were incubated for 1 hour at room temperature before discarding the liquid and washing the wells twice with PBST. One hundred microlitres of horse radish peroxidase (HRP)-linked sheep anti-mouse Ig antibody (Amersham product NXA 931), diluted 1 in 500 with PBST containing 0.5% w/v BSA, was added and the plates were incubated for 1 hour at room temperature before discarding the liquid and washing the wells twice with PBST. One hundred microlitres of 2,2'-azino-bis(3-ethylbenzthiazoline-6-sulphonic acid) (ABTS) solution, freshly prepared using one 50 mg ABTS tableoehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20–60 minutes at room temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibition of enzyme activity.

(b) In Vitro HUVEC Proliferation Assay

This assay determines the ability of a test compound to inhibit the growth factor-stimulated proliferation of human umbilical vein endothelial cells (HUVEC).

HUVEC cells were isolated in MCDB 131 (Gibco BRL)+ 7.5% v/v foetal calf serum (FCS) and were plated out (at passage 2 to 8), in MCDB 131+2% v/v FCS+3µg/ml heparin 1 µg/ml hydrocortisone, at a concentration of 1000 cells/well in 96 well plates. After a minimum of 4 hours they were dosed with the appropriate growth factor (i.e. VEGF 3 ng/ml, EGF 3 ng/ml or b-FGF 0.3 ng/ml) and compound. The cultures were then incubated for 4 days at 37° C. with 7.5% $CO_2$. On day 4 the cultures were pulsed with 1 µCi/well of tritiated-thymidine (Amersham product TRA 61) and incubated for 4 hours. The cells were harvested using a 96-well plate harvester (Tomtek) and then assayed for incorporation of tritium with a Beta plate counter. Incorporation of radioactivity into cells, expressed as cpm, was used to measure inhibition of growth factor-stimulated cell proliferation by compounds.

(c) In Vivo Rat Uterine Oedema Assay

This test measures the capacity of compounds to reduce the acute increase in uterine weight in rats which occurs in the first 4–6 hours following oestrogen stimulation. This early increase in uterine weight has long been known to be due to oedema caused by increased permeability of the uterine vasculature and recently Cullinan-Bove and Koos (Endocrinology, 1993,133:829–837) demonstrated a close temporal relationship with increased expression of VEGF mRNA in the uterus. We have found that prior treatment of the rats with a neutralising monoclonal antibody to VEGF significantly reduces the acute increase in uterine weight, confirming that the increase in weight is substantially mediated by VEGF.

Groups of 20 to 22-day old rats were treated with a single subcutaneous dose of oestradiol benzoate (2.5 µg/rat) in a solvent, or solvent only. The latter served as unstimulated controls. Test compounds were orally administered at various times prior to the administration of oestradiol benzoate. Five hours after the administration of oestradiol benzoate the rats were humanely sacrificed and their uteri were dissected, blotted and weighed. The increase in uterine weight in groups treated with test compound and oestradiol benzoate and with oestradiol benzoate alone was compared using a Student T test. Inhibition of the effect of oestradiol benzoate was considered significant when $p<0.05$.

According to a further aspect of the invention there is provided a pharmaceutical composition which comprises a compound of the formula I as defined hereinbefore or a pharmaceutically acceptable salt thereof, in association with a pharmaceutically acceptable excipient or carrier which is in one of the following forms: (i) a tablet, lozenge or capsule suitable for oral administration; (ii) a parenteral injection (including intravenous, subcutaneous, intramuscular, intravascular or infusion) for example as a sterile solution, suspension or emulsion; (iii) an ointment, patch or cream for topical administration; or (iv) a suppository for rectal administration. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square metre body area of the animal, i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–250 mg of active ingredient.

According to a further aspect of the present invention there is provided a compound of the formula I or a pharmaceutically acceptable salt thereof as defined hereinbefore for use in a method of treatment of the human or animal body by therapy.

We have found that compounds of the present invention inhibit VEGF receptor tyrosine kinase activity and are therefore of interest for their antiangiogenic effects and/or their ability to cause a reduction in vascular permeability.

Thus according to a further aspect of the invention there is provided the use of a compound of the formula I, or a pharmaceutically acceptable salt thereof in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a warm-blooded animal, such as a human being, in need of such treatment which comprises administering to said animal an effective amount of a compound of formula I or a pharmaceutically acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The antiangiogenic and/or vascular permeability reducing treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined hereinbefore may be: surgery, radiotherapy or chemotherapy. Such chemotherapy may cover three main categories of therapeutic agent:

(i) other antiangiogenic agents that work by different mechanisms from those defined hereinbefore (for example linomide, inhibitors of integrin αvβ3 function, angiostatin, razoxin, thalidomide);

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example EGF, FGFs, platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); topoisomerase inhibitors (for example epipodophyllotoxins like etoposide and teniposide, amsacrine, topotecan).

As stated above the compounds defined in the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, acute and chronic nephropathies, atheroma, arterial restenosis, autoimmune diseases, acute inflammation and ocular diseases with retinal vessel proliferation. In particular such compounds of the invention are expected to inhibit the growth of those primary and recurrent solid tumours which are associated with VEGF, especially those tumours which are significantly dependent on VEGF for their growth and spread, including for example, certain tumours of the colon, breast. prostate, lung, vulva and skin.

In addition to their use in therapeutic medicine, the compounds of formula I and their pharmaceutically acceptable salts are also useful as pharmacological tools in the development and standardisation of in vitro and in vivo test systems for the evaluation of the effects of inhibitors of VEGF receptor tyrosine kinase activity in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated in the following non-limiting Examples in which, unless otherwise stated:

[(i) evaporations were carried out by rotary evaporation in vacuo and work-up procedures were carried out after removal of residual solids such as drying agents by filtration:

(ii) operations were carried out at ambient temperature, that is in the range 18–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points are uncorrected and were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet;

(vii) intermediates were not generally fully characterised and purity was assessed by thin layer chromatography (TLC), high-performance liquid chromatography (HPLC), infra-red (IR) or NMR analysis;

(viii) petroleum ether refers to that fraction boiling between 40–60° C.

(ix) the following abbreviations have been used:
DMF N,N-dimethylformamide
DMSO dimethylsulphoxide
TFA trifluoroacetic acid
NMP 1-methyl-2-pyrrolidinone
DMAP 4-dimethylaminopyridine]

EXAMPLE 1

4-Chloro-6-cyano-7-(2-methoxyethoxy)quinoline hydrochloride (300 mg, 1 mmol) and 2-fluoro-5-hydroxy-4-methylaniline (141 mg, 1 mmol) in isopropanol (10 ml) was heated at reflux for 2 hours. The mixture was allowed to cool, the precipitated product collected by filtration, washed with acetone and dried to give 6-cyano-4-(2-fluoro-5-hydroxy-4-methylanilino)-7-(2-methoxyethoxy)quinoline hydrochloride (273 mg, 68%).

m.p. 300–302° C. $^1$H NMR Spectrum: (DMSOd$_6$) 2.2 (s, 3H); 3.4 (s, 3H); 3.8 (t, 2H); 4.4 (t, 2H); 6.5 (dd, 1H), 6.9 (d, 1H); 7.7 (s, 1H); 8.5 (d, 1H); 9.4 (s, 1H); 9.9 (br s, 1H); 11.2 (br s, 1H) M>S—ESI: 368 [MH]$^+$;

| Elemental analysis: | Found | C 59.3 | H 4.8 | N 10.2 |
|---|---|---|---|---|
| C$_{20}$H$_{18}$N$_3$O$_3$F 1HCl | Requires | C 57.5 | H 4.7 | N 10.4% |

The starting material was prepared as follows:

Methyl chloroformate (6.8 ml, 88 mmol) was added over 30 minutes to a solution of 4-fluoro-2-methylphenol (10 g, 79 mmol) in 6% aqueous sodium hydroxide solution at 0° C. The mixture was stirred for 2 hours, then extracted with ethyl acetate (100 ml). The ethyl acetate extract was washed with water (100 ml) and dried (MgSO$_4$) and the solvent removed by evaporation to give 4-fluoro-2-methylphenyl methyl carbonate (11.4 g, 78%) as an oil.

$^1$H NMR Spectrum: (DMSOd$_6$) 2.14 (s, 3H); 3.81 (s, 3H); 7.05 (m, 1H); 7.1–7.25 (m, 2H).

A mixture of concentrated nitric acid (6 ml) and concentrated sulphuric acid (6 ml) was added slowly to a solution of 4-fluoro-2-methylphenyl methyl carbonate (11.34 g, 62 mmol) in concentrated sulphuric acid (6 ml) such that the temperature of the mixture was kept below 50° C. The mixture was stirred for 2 hours, then ice/water was added and the precipitated product collected by filtration. The crude product was purified by chromatography on silica eluting with methylene chloride/hexane progressing through increasingly polar mixtures to methanol/methylene chloride (1:19) to give 4-fluoro-2-methyl-5-nitrophenol (2.5 g, 22%) as a solid.

$^1$H NMR Spectrum: (DMSOd$_6$; CD$_3$COOD) 2.31 (s, 3H); 7.38 (d, 1H); 7.58 (d, 1H); MS–ESI: 171 [MH]$^+$.

A mixture of 4-fluoro-2-methyl-5-nitrophenol (2.1 g, 13 mmol), iron powder (1 g, 18 mmol) and iron(II)sulphate (1.5 g, 10 mmol) in water (40 ml) was heated at reflux for 4 hours.

The mixture was allowed to cool, neutralised with 2M aqueous sodium hydroxide and extracted with ethyl acetate (100 ml). The ethyl acetate extract was dried (MgSO$_4$) and the solvent removed by evaporation to give 2-fluoro-5-hydroxy-4-methylaniline (0.8 g, 47%) as a solid.

$^1$H NMR Spectrum: (DMSOd$_6$) 1.94 (s, 3H); 4.67 (s, 2H); 6.22 (d, 1H); 6.65 (d, 1H); 8.68 (s, 1H); MS–ESI: 142 [MH]$^+$.

Sodium hydride (300 mg of an 80% suspension in mineral oil, 10 mmol) was added to 2-methoxyethanol (0.76 g, 10 mmol) in NMP (5 ml) and the mixture stirred for 15 minutes. 4-Amino-2-chlorobenzonitrile (1.5 g, 10 mmol) was added and the mixture heated at 100° C. for 5 hours. The mixture was allowed to cool, diluted with water and extracted with ethyl acetate (3×50 ml). The combined extracts were dried (MgSO$_4$) and the solvent removed by evaporation. The residue was purified by chromatography eluting with increasingly polar mixtures of methylene chloride/ethyl acetate to give 4-cyano-3-(2-methoxyethoxy)aniline (760 mg, 40%) as a dark yellow oil.

$^1$H NMR Spectrum: (DMSOd$_6$) 3.36 (s, 3H); 3.67 (t, 2H); 4.10 (t, 2H); 6.1 (s, 2H); 620 (dd, 1H); 6.23 (s 1H); 7.20 (d, 1H); MS–ESI: 193 [MH]$^+$.

4-Cyano-3-(2-methoxyethoxy)aniline (760 mg, 4 mmol) and 2,2-dimethyl-5-methoxymethylene-1,3-dioxane-4,6-dione (1.0 g, 5.4 mmol), (Montatsh. Chem. 1967, 98, 564), in ethanol (20 ml) was heated at reflux for 1 hour. The mixture was allowed to cool and the solid collected by filtration to give 5-((4-cyano-3-(2-methoxyethoxy)anilino)methylene)-2,2-dimethyl-1,3-dioxane-4,6-dione (840 mg, 61%) as an orange solid.

$^1$H NMR Spectrum: (DMSOd$_6$) 1.7 (s, 6H); 3.4 (s, 3H); 3.7 (t, 2H); 4.4 (t, 2H); 7.3 (dd, 1H); 7.6 (d, 1H); 7.7 (d, 1H): 8.7 (br d, 1H); 11.3 (br d, 1H); MS–ESI: 347 [MH]$^+$; 289 [MH–C$_3$H$_6$O]$^+$.

5-((4-Cyano-3-(2-methoxyethoxy)anilino)methylene)-2,2-dimethyl-1,3-dioxane-4,6-dione (840 mg, 2.4 mmol) was added in portions to a mixture of biphenyl (8 ml) and phenyl ether (22 ml) at 250° C. and the mixture stirred at that temperature for 30 minutes. The mixture was allowed to cool, hexane was added and the solid product collected by filtration and recrystallised from methylene chloride/methanol/hexane to give 6-cyano-7-(2-methoxyethoxy)-1,4-dihydroquinolin-4-one (230 mg, 38%).

m.p. 344–246° C.; $^1$H NMR Spectrum: (DMSOd$_6$) 3.4 (s, 3H); 3.8 (t, 2H); 4.3 (t, 2H); 6.0 (d, 1H); 7.1 (s, 1H); 7.9 (t, 1H); 8.3 (s, 1H); 9.4 (s, 1H); 11.7 (br d, 1H).

6-Cyano-7-(2-methoxyethoxy)-1,4-dihydroquinolin-4-one (1.9 g, 7.8 mmol) and DMF (0.2 ml) in thionyl chloride (50 ml) were heated at reflux for 2 hours. Excess thionyl chloride was removed by evaporation and the residue azeotroped with toluene and dried under vacuum to give 4-chloro-6-cyano-7-(2-methoxyethoxy)quinoline hydrochloride (2.4 g, 82%) as a solid.

$^1$H NMR Spectrum: (DMSOd) 3.35 (s, 3H); 3.75 (t, 2H); 4.40 (t, 2H); 7.72 (s, 1H); 7.75 (d, 1H); 7.7 (d, 1H); 8.65 (s, 1H); 8.90 (d, 1H); MS–ESI: 263 [MH]$^+$; 205 [MH–C$_3$H$_6$O]$^+$.

EXAMPLE 2

A suspension of 4-chloro-6,7-dimethoxyquinoline (0.2 g, 0.89 mmol) and 4-chloro-2-fluoro-5-hydroxyaniline (173 mg, 1 mmol), (as described in EP 61741 A2), in 2-pentanol (2.5 ml) was heated at 120° C. for 6 hours. The resulting solid was collected by filtration, washed with isopropanol and then ether and dried under vacuum to give 4-(4-chloro-2-fluoro-5-hydroxyanilino)-6,7-dimethoxyquinoline hydrochloride (231 mg, 67%) as a white solid.

m.p. 312–318° C.; $^1$H NMR Spectrum: (DMSOd$_6$) 3.95 (s, 3H); 4.0 (s, 3H); 6.52 (dd, 1H); 7.15 (d, 1H); 7.45 (s, 1H); 7.65 (d, 1H); 8.12 (s, 1H); 8.4 (d, 1H); 10.6 (s, 1H); 10.8 (s, 1H); MS–ESI: 349 [MH]$^+$;

| Elemental analysis: | Found | C 52.6 | H 4.0 | N 7.3 |
| C$_{17}$H$_{14}$N$_2$O$_3$ClF 1HCl | Requires | C 53.0 | H 3.9 | N 7.3% |

The starting material was prepared as follows:

A suspension of 6,7-dimethoxy-1,4-dihydroquinolin-4-one (3 g, 14 mmol), (J. Chem. Soc. 1940, 1209), in thionyl chloride (60 ml) and DMF (0.3 ml) was heated at reflux for 3 hours. Excess thionyl chloride was removed by evaporation and the residue azeotroped with toluene and washed with ether to give 4-chloro-6,7-dimethoxyquinoline hydrochloride.

4-Chloro-6,7-dimethoxyquinoline hydrochloride was dissolved in ethyl acetate, and the solution washed with a saturated solution of sodium hydrogen carbonate and then brine, dried (MgSO$_4$) and the volatiles removed by evaporation. The crude product was purified by flash chromatography eluting with methylene chloride/acetonitrile (9/1 followed by 8/2) to give 4-chloro-6,7-dimethoxyquinoline (2.5 g, 80%) as a yellow solid.

10 m.p. 131–132° C.; $^1$H NMR Spectrum: (CDCl$_3$) 4.05 (s, 3H); 4.1 (s, 3H); 7.35 (d, 1H); 7.42 (s, 1H); 7.45 (s, 1H); 8.6 (d, 1H); MS–ESI: 223 [MH]$^+$;

| Elemental analysis: | Found | C 58.7 | H 4.7 | N 6.1 |
| C$_{11}$H$_{10}$NO$_2$Cl | Requires | C 59.1 | H 4.5 | N 6.3% |

EXAMPLE 3

A mixture of 4-(5-benzyloxy-2-fluoro-4-methylphenoxy)-6-methoxy-7-(3-morpholinopropoxy)quinoline (274 mg, 0.5 mmol) and 10% palladium-on-charcoal catalyst (274 mg) in DMF (10 ml) and methanol (10 ml) was stirred under hydrogen at 5 atmospheres pressure for 3 hours. The catalyst was removed by filtration through diatomaceous earth and the solvent removed by evaporation. The resulting solid was suspended in ether, collected by filtration and washed with methylene chloride and isopropanol to give 4-(2-fluoro-5-hydroxy-4-methylphenoxy)-6-methoxy-7-(3-morpholinopropoxy)quinoline (134 mg, 25 60%).

m.p. 210–217° C.; $^1$H NMR Spectrum: (DMSOd$_6$; CF$_3$COOD) 2.05 (t, 2H); 2.17 (s, 3H); 2.62 (br s, 4H); 2.68 (t, 2H); 3.65 (t, 4H); 3.95 (s, 3H); 4.22 (t, 2H); 6.48 (d, 1H); 6.75 (d, 1H) 7.2 (d, 1H); 7.45 (s, 1H); 7.52 (s, 1H); 8.48 (d, 1H); MS–ESI: 443 [MH]$^+$;

| Elemental analysis: | Found | C 64.1 | H 6.5 | N 6.1 |
| C$_{24}$H$_{22}$N$_2$O$_5$F 0.4H$_2$O | Requires | C 64.1 | H 6.2 | N 6.2% |

The starting material was prepared as follows:

Concentrated aqueous ammonia solution (30 ml) was added to a solution of (4-fluoro-2-methyl-5-nitrophenyl)

methyl carbonate (6 g, 26 mmol), (prepared as described in EP 0307777 A2), in methanol (150 ml) and the mixture stirred for 1 hour at ambient temperature. Most of the organic solvent was removed by evaporation and the residue was partitioned between water and ethyl acetate. The organic layer was separated, dried (MgSO$_4$) and the volatiles removed by evaporation to give 4-fluoro-2-methyl-5-nitrophenol (4.45 g, 100%).

$^1$H NMR Spectrum: (DMSOd$_6$) 2.18 (s, 3H); 7.32 (d, 1H); 7.44 (d, 1H).

A mixture of 4-fluoro-2-methyl-5-nitrophenol (4.69 g, 27 mmol), benzyl bromide (3.59 ml, 30 mmol) and potassium carbonate (7.58 g, 55 mmol) in DMF (100 ml) was heated at 80° C. for 4 hours. The mixture was allowed to cool and diluted with water and stirred for 15 minutes. The precipitated product was collected by filtration, washed with water and dried to give 5-benzyloxy-2-fluoro-4-methyl-1-nitrobenzene (6.4 g, 89%).

$^1$H NMR Spectrum: (DMSOd$_6$) 2.28 (s, 3H); 5.22 (s, 2H); 7.3–7.5 (m, 6H); 7.70 (s, 1H).

5-Benzyloxy-2-fluoro-4-methyl-1-nitrobenzene (500 mg, 1.9 mmol) in methanol (110 ml) was added to a suspension of Raney nickel (75 mg) and hydrazine hydrate (0.47 ml, 9.5 mmol) in methanol (10 ml) and heated at reflux. The mixture was maintained under reflux for 15 minutes and then the insoluble materials removed by filtration through diatomaceous earth. The filter pad was washed with methanol and the solvent removed from the filtrate by evaporation to give 5-benzyloxy-2-fluoro-4-methylaniline (440 mg, 99%).

$^1$H NMR Spectrum: (DMSOd$_6$) 2.02 (s, 3H); 4.88 (s, 2H); 4.98 (s, 2H); 6.44 (d, 1H); 6.76 (d, 1H); 7.3–7.5 (m, 5H).

A solution of sodium nitrite (1.68 g, 24 mmol) in water (3.5 ml) was added to a solution of 5-benzyloxy-2-fluoro-4-methylaniline (4.7 g, 20 mmol) in acetic acid (25 ml) and 70% sulphuric acid (25 ml) at 10° C. The mixture was stirred at 10° C. for 20 minutes and a solution of copper(II)nitrate trihydrate (481 g, 2 mol) in water (790 ml) followed by copper(II)oxide (3 g, 19 mmol) was added. The mixture was stirred for 3 hours then extracted with ethyl acetate. The organic layer was washed with water, brine, dried (MgSO$_4$) and the solvent removed by evaporation. The residue was purified by column chromatography eluting with petroleum ether/ether (85/15) to give 5-benzyloxy-2-fluoro-4-methylphenol (1.25 g, 27%) as an orange oil.

$^1$H NMR Spectrum (DMSOd$_6$): 2.07 (s, 3H); 5.02 (s, 2H); 6.59 (d, 1H); 6.93 (d, 1H); 7.30–7.45 (m, 5H); 9.5 1 (br s, 1H).

A solution of Meldrum's acid (32 g, 22.2 mmol) in methyl orthoformate (200 ml) was stirred at 100° C. 3-Hydroxy-4-methoxyaniline (28 g, 20 mmol) was added and the solution was heated at reflux for 15 minutes. After cooling, the mixture was stirred overnight at ambient temperature. The precipitate was collected by filtration, washed with methyl orthoformate followed by ether and dried under vacuum to give 5-((3-hydroxy-4-methoxyanilino)methylene)-2,2-dimethyl-1,3-dioxane-4,6-dione (47.5 g, 82%).

$^1$H NMR Spectrum: (CDCl$_3$) 1.75 (s, 6H); 3.92 (s, 3H); 5.9–6.0 (br s, 1H); 6.72 (dd, 1H); 6.9 (m, 2H); 7.26 (s, 1H); 8.55 (d, 1H).

A mixture of 5-((3-hydroxy-4-methoxyanilino)methylene)-2,2-dimethyl-1,3-dioxane-4,6-dione (20 g, 69 mmol), potassium carbonate (12.4 g, 90 mmol) and benzyl bromide (15.4 g, 90 mmol) in DMF (100 ml) was heated at 65° C. for 2 hours. Two thirds of the DMF was removed from the mixture by evaporation, the mixture was diluted with water, adjusted to pH4 with 5M hydrochloric acid and extracted with ethyl acetate. The combined extracts were washed with water and then brine, dried (MgSO$_4$) and the volatiles removed by evaporation. The solid residue was triturated with ether, and collected by filtration and dried under vacuum to give 5-((3-benzyloxy-4-methoxyanilino)methylene)-2,2-dimethyl-1,3-dioxane-4,6-dione (22 g, 83%) as a cream solid.

$^1$H NMR Spectrum: CDCl$_3$) 1.75 (s, 6H); 3.9 (s, 3H); 5.17 (s, 2H); 6.8 (s, 1H); 6.82 (dd, 1H); 6.92 (d, 1H); 7.35 (dd, 1H); 7.4 (t, 2H); 7.48 (d, 2H); 8.5 (d, 1H); MS–ESI: 406 [MNa]$^+$;

| Elemental analysis: | Found | C 65.7 | H 5.8 | N 3.5 |
|---|---|---|---|---|
| C$_{21}$H$_{21}$NO$_6$ | Requires | C 65.8 | H 5.5 | N 3.7% |

5-((3-Benzyloxy-4-methoxyanilino)methylene)-2,2-dimethyl-1,3-dioxane-4,6-dione (10 g, 26 mmol) was rapidly added to phenyl ether (150 ml) heated at reflux. The mixture maintained a vigorous reflux for 5 minutes, and was allowed to cool to 45° C. then poured into petroleum ether. The resulting solid was collected by filtration and purified by column chromatography eluting with methylene chloride/methanol (95/5 followed by 90/10 and 85/5) to give 7-benzyloxy-6-methoxy-1,4-dihydroquinolin-4-one (6 g, 82%) as a yellow solid.

m.p. 235–236° C.; $^1$H NMR Spectrum: (DMSOd$_6$) 3.83 (s, 3H); 5.19 (s, 2H); 5.95 (d, 1H); 7.06 (s, 1H); 7.3–7.5 (m, 6H); 7.75 (d, 1H); MS–ESI: 281 [MH]$^+$;

| Elemental analysis: | Found | C 68.9 | H 5.5 | N 4.7 |
|---|---|---|---|---|
| C$_{17}$H$_{15}$NO$_3$ 0.9H$_2$O | Requires | C 68.6 | H 5.7 | N 4.7% |

A suspension of 7-benzyloxy-6-methoxy-1,4-dihydroquinolin-4-one (3.37 g, 13 mmol) in thionyl chloride (50 ml) and DMF (0.25 ml) was heated at reflux for 1 hour. Excess thionyl chloride was removed by evaporation and the residue azeotroped with toluene and triturated with ether, the product collected by filtration and dried under vacuum to give 7-benzyloxy-4-chloro-6-methoxyquinoline hydrochloride (3.9 g, 89%).

m.p. 191–192° C.; $^1$H NMR Spectrum: CDCl$_3$) 4.10 (s, 3H); 5.41 (s, 2H); 7.4 (dd, 1H); 7.43 (t, 2H); 7.49 (s, 1H); 7.58 (d, 2H); 7.70 (d, 1H); 8.39 (s, 1H); 8.60 (d, 1H); MS–ESI: 300 [MH]$^+$;

| Elemental analysis: | Found | C 59.0 | H 4.7 | N 3.9 |
|---|---|---|---|---|
| C$_{17}$H$_{14}$NO$_2$Cl 0.71H$_2$O 0.95HCl | Requires | C 58.8 | H 4.8 | N 4.0% |

A solution of 7-benzyloxy-4-chloro-6-methoxyquinoline hydrochloride (6.8 g, 20 mmol) in TFA (80 ml) was heated at reflux for 5.5 hours. The volatiles were removed by evaporation, the residue suspended in water and the mixture was adjusted to pH7 with a saturated aqueous sodium hydrogen carbonate solution. The resulting solid was collected by filtration, washed with water, ether and dried under vacuum to give 4-chloro-7-hydroxy-6-methoxyquinoline (4.1 g, 98%).

$^1$H NMR Spectrum: (DMSOd$_6$) 3.99 (s, 3H); 7.36 (s, 1H); 7.39 (s, 1H); 7.54 (d, 1H); 8.6 (d, 1H); 10.5–10.7 (br s, 1H).

Diethyl azodicarboxylate (120 μl, 0.76 mmol) was added dropwise to a solution of triphenylphosphine (200 mg, 0.76 mmol), 4-chloro-7-hydroxy-6-methoxyquinoline (100 mg, 0.47 mmol), 3-morpholino-1-propanol (75 mg, 0.52 mmol), (Tet. Lett. 1994, 35, 1715), in methylene chloride (5 ml). The mixture was stirred for 4 hours at ambient temperature, the solvent was removed by evaporation to dryness and purified by column chromatography eluting with methylene chloride/methanol (9/1) to give 4-chloro-6-methoxy-7-(3-morpholinopropoxy)quinoline (105 mg, 66%).

$^1$H NMR Spectrum: (DMSOd$_6$) 2.05 (m, 2H); 2.62 (br s, 4H); 2.68 (t, 2H); 3.65 (t, 4H); 3.98 (s, 3H); 4.25 (t, 2H); 7.4 (s, 1H); 7.48 (s, 1H); 7.55 (d, 1H); 8.62 (d, 1H).

4-Chloro-6-methoxy-7-(3-morpholinopropoxy)quinoline (250 mg, 0.74 mmol) was added to a solution of 5-benzyloxy-2-fluoro-4-methylphenol (257 mg 1.1 mmol) and potassium t-butoxide (125 mg, 1.1 mmol) in DMSO (3 ml) and the mixture heated at 160° C. for 1.5 hours. The mixture was allowed to cool and was partitioned between water and ethyl acetate. The organic layer was separated, washed with brine, dried (MgSO$_4$), and the solvent removed by evaporation. The residue was purified by column chromatography eluting with methylene chloride/methanol (95/5) to give 4-(5-benzyloxy-2-fluoro-4-methylphenoxy)-6-methoxy-7-(3-morpholinopropoxy)quinoline (105 mg, 69%).

$^1$H NMR Spectrum: CDCl$_3$) 2.1–2.2 (m, 2H); 2.31 (s, 3H); 2.5 (br s, 4H); 2.6 (t, 2H); 3.75 (t, 4H); 4.05 (s, 3H); 4.3 (t, 2H); 5.02 (s, 2H); 6.34 (d, 1H); 6.76 (d, 1H); 7.06 (d, 1H); 7.3–7.4 (m, 5H); 7.43 (s, 1H); 7.58 (s, 1H); 8.45 (d, 1H); MS–ESI: 555 [MNa]$^+$.

EXAMPLE 4

A solution of 4-(5-benzyloxy-2-fluoro-4-methylphenoxy)-6-cyano-7-(2-methoxyethoxy)quinoline (198 mg, 0.43 mmol) in TFA (4 ml) was heated at 70° C. for 1 hour.

Half the solvent was then removed by evaporation and the mixture diluted with water and adjusted to pH7 with 2M aqueous sodium hydroxide solution. The aqueous mixture was extracted with ethyl acetate, the organic layer was separated and washed with brine, dried (MgSO$_4$) and the solvent removed by evaporation. The residue was purified by column chromatography eluting with methylene chloride/methanol (95/5) to give 6-cyano-4-(2-fluoro-5-hydroxy-4-methylphenoxy)-7-(2-methoxyethoxy)quinoline (71 mg, 44%).

$^1$H NMR Spectrum: (DMSOd$_6$) 2.17 (s, 3H); 3.38 (s, 3H); 3.8 (dd, 2H); 4.45 (dd, 2H); 6.65 (d, 1H); 6.8 (d, 1H); 7.25 (d, 1H); 7.66 (s, 1H); 8.78 (d, 1H); 8.83 (s, 1H); 9.81 (br s, 1H); MS–ESI: 369 [MH]$^+$;

| Elemental analysis: | Found | C 63.9 | H 4.3 | N 7.2 |
| C$_{20}$H$_{17}$N$_2$O$_4$F | Requires | C 63.7 | H 4.8 | N 7.4% |

The starting material was prepared as follows:

4-Chloro-6-cyano-7-(2-methoxyethoxy)quinoline (187 mg, 0.71 mmol), (prepared as described for the starting material in Example 1 but with an aqueous sodium hydrogen carbonate work up), was added to a solution of 5-benzyloxy-2-fluoro-4-methylphenol (248 mg, 1 mmol), (prepared as described for the starting material in Example 3), and potassium t-butoxide (120 mg, 1 mmol) in DMSO (5 ml) and the mixture then heated at 160° C. for 1.5 hours. The mixture was diluted with water and extracted with ethyl acetate. The organic layer was separated, washed with brine, dried (MgSO$_4$) and the solvent removed by evaporation. The residue was purified by column chromatography eluting with methylene chloride/ethyl acetate (55/45) followed by preparative reverse-phase HPLC eluting with aqueous ammonium carbonate (2 g/l, adjusted to pH7 with carbon dioxide) and methanol (20/80) to give 4-(5-benzyloxy-2-fluoro-4-methylphenoxy)-6-cyano-7-(2-methoxyethoxy)quinoline (204 mg, 63%).

$^1$H NMR Spectrum: CDCl$_3$) 2.32 (s, 3H); 3.52 (s, 3H); 3.91 (dd, 2H); 4.36 (t, 2H); 5.04 (s, 2H); 6.39 (d, 1H); 6.75 (d, 1H); 7.1 (d, 1H); 7.3–7.45 (m, 5H); 7.5 (s, 1H); 8.65 (d, 1H); 8.7 (s, 1H).

EXAMPLE 5

A mixture of 4-chloro-6-methoxy-7-(2-methoxyethoxy)quinoline hydrochloride (250 mg, 0.82 mmol) and 3-hydroxy-4-methylaniline (123 mg, 1 mmol) in DMF (5 ml) was heated at 150° C. for 30 minutes. The mixture was diluted with isopropanol and the resulting solid collected by filtration and washed with isopropanol to give 4-(3-hydroxy-4-methylanilino)-6-methoxy-7-(2-methoxyethoxy)quinoline hydrochloride (168 mg, 58%).

$^1$H NMR Spectrum: (DMSO$_6$; CF$_3$COOD) 2.16 (s, 3H); 3.34 (s, 3H); 3.76 (t, 2H); 3.97 (s, 3H); 4.28 (t, 2H); 6.71 (d, 1H); 6.74 (d, 1H); 6.84 (d, 1H); 7.19 (d, 1H); 7.33 (s, 1H); 7.98 (s, 1H); 8.26 (d, 1H); MS–ESI: 355 [MNa]$^+$;

| Elemental analysis: | Found | C 61.9 | H 6.3 | N 7.3 |
| C$_{20}$H$_{22}$N$_2$O$_4$ 1HCl | Requires | C 61.5 | H 5.9 | N 7.2% |

The starting material was prepared as follows:

A mixture of 2-methoxy-5-nitrophenol (6 g, 35 mmol), 2-bromoethyl methyl ether (4 ml, 40 mmol), potassium carbonate (5.8 g, 40 mmol) and potassium iodide (0.5 g) in DMF (50 ml) was heated at 80° C. for 1 hour. The mixture was allowed to cool and poured into water (400 ml). The resulting precipitate was collected by filtration, washed with water and dried under vacuum to give 4-methoxy-3-(2-methoxyethoxy)nitrobenzene (7.75 g, 98%).

$^1$H NMR Spectrum: (CDCl$_3$) 3.46 (s, 3H); 3.82 (t, 2H); 3.96 (s, 3H); 4.25 (t, 2H); 6.91 (d, 1H); 7.79 (d, 1H); 7.92 (dd, 1H); MS–ESI: 227 [MH]$^+$;

A mixture of 4-methoxy-3-(2-methoxyethoxy)nitrobenzene (7 g, 30 mmol) and 10% palladium-on-charcoal catalyst (1.4 g) in ethyl acetate (70 ml) was stirred under hydrogen at 3.3 atmospheres pressure for 1 hour. The catalyst was removed by filtration through diatomaceous earth and the solvent removed by evaporation. The solid residue was suspended in ethyl acetate, collected by filtration and dried under vacuum to give 4-methoxy-3-(2-methoxyethoxy)aniline (6.1 g, 100%).

$^1$H NMR Spectrum: (CDCl$_3$) 3.4 (s, 3H); 3.75 (t, 2H); 3.8 (s, 3H); 4.12 (t, 2H); 6.24 (dd, 1H); 6.34 (d, 1H); 6.7 (d, 1H); MS–ESI: 197 [MH]$^+$;

A solution of 4-methoxy-3-(2-methoxyethoxy)aniline (5 g, 25.3 mmol) and diethyl ethoxymethylenemalonate (6 ml, 30 mmol) was heated at 110° C. for 30 minutes. Phenyl ether (5 ml) was added and the mixture was heated at 240° C. for 6 hours. The mixture was allowed to cool and diluted with petroleum ether. The resulting solid was collected by filtration and purified by reverse phase chromatography on a Diaion (trade mark of Mitsubishi) HP20SS resin column eluting with acetonitrile/water (40/60) to give 6-methoxy-7-(2-methoxyethoxy)-1,4-dihydroquinolin-4-one (500 mg, 8%).

$^1$H NMR Spectrum: (DMSOd$_6$) 3.35 (s, 3H); 3.75 (dd, 2H); 3.85 (s, 3H); 4.18 (dd, 2H); 5.95 (d, 1H); 7.0 (s, 1H); 7.48 (s, 1H); 7.78 (d, 1H); MS–ESI: 250 [MH]$^+$ A solution of 6-methoxy-7-(2-methoxyethoxy)-1,4-dihydroquinolin-4-one (500 mg, 2 mmol) in thionyl chloride (10 ml) and DMF (3 drops) was heated at reflux for 1 hour. Excess thionyl chloride was removed by evaporation and the residue azeotroped with toluene and then triturated with ether. The solid was collected by filtration and dried under vacuum to give 4-chloro-6-methoxy-7-(2-methoxyethoxy) quinoline hydrochloride (590 mg, 95%).

$^1$H NMR Spectrum: (DMSOd$_6$) 3.36 (s, 3H); 3.8 (t, 2H); 4.05 (s, 3H); 4.35 (t, 2H); 7.51 (s, 1H); 7.68 (s, 1H); 7.91 (d, 1H); 8.85 (d, 1H).

EXAMPLE 6

A solution of 3-hydroxy-4-methylaniline (68 mg, 0.55 mmol) and 7-benzyloxy-4-chloro-6-methoxyquinoline hydrochloride (168 mg, 0.5 mmol), (prepared as described for the starting material in Example 3), in 2-ethoxyethanol (5 ml) was heated at reflux for 1 hour. The mixture was allowed to cool, the precipitate collected by filtration, washed with 2-ethoxyethanol and then ether and dried under vacuum to give 7-benzyloxy-4-(3-hydroxy-4-methylanilino)-6-methoxyquinoline hydrochloride (130 mg, 61%).

$^1$H NMR Spectrum: (DMSOd$_6$) 2.19 (s, 3H); 4.10 (s, 3H); 5.33 (s, 2H); 6.71 (d, 1H); 6.80 (d, 1H); 6.88 (d, 1H); 7.24 (d, 1H); 7.35–7.52 (m, 6H); 7.55 (t, 2H); 8.1 (s, 1H); 8.32 (d, 1); 9.88 (s, 1H); MS–ESI: 387 [MH]$^+$

| Elemental analysis: | Found | C 67.4 | H 5.7 | N 6.5 |
| C$_{24}$H$_{22}$N$_2$O$_3$ 0.53H$_2$O 0.9HCl | Requires | C 67.2 | H 5.6 | N 6.5% |

EXAMPLE 7

A solution of 4-chloro-6-methoxy-7-(3-morpholinopropoxy)quinoline hydrochloride (300 mg, 0.73 mmol), and 4-chloro-2-fluoro-5-hydroxyaniline (130 mg, 0.8 mmol), (as described in EP 61741 A2), in 2-pentanol (15 ml) was heated at reflux for 5 hours. The resulting solid was collected by filtration, washed with acetone and dried under vacuum to give 4-(4-chloro-2-fluoro-5-hydroxyanilino)-6-methoxy-7-(3-morpholinopropoxy)quinoline hydrochloride hydrate (283 mg, 73%) as a yellow solid.

$^1$H NMR Spectrum: (DMSOd$_6$) 2.38 (t, 2H); 3.15 (dd, 2H); 3.35 (m, 2H); 3.52 (d, 2H); 3.85 (t, 2H); 4.0 (d, 2H); 4.05 (s, 3H); 4.3 (t, 2H); 6.52 (dd, 1H); 7.2 (d, 1H); 7.55 (s, 1H); 8.25 (s, 1H); 8.42 (d, 1H); 10.72 (s, 1H); 10.85 (s, 1H); 11.1 (br s, 1H); MS–ESI: 462 [MH]$^+$;

| Elemental analysis: | Found | C 50.6 | H 5.5 | N 7.2 |
| C$_{23}$H$_{25}$N$_3$O$_4$ClF 0.5H$_2$O 2HCl | Requires | C 50.8 | H 5.2 | N 7.7% |

The starting material was prepared as follows:

A solution of 5-((3-hydroxy-4-methoxyanilino) methylene)-2,2-dimethyl-1,3-dioxane-4,6-dione, (prepared as described for the starting material in Example 3), 4-(3-chloropropyl)morpholine hydrochloride (680 mg, 3.57 mmol), (J. Amer. Chem. Soc. 1945, 67, 736), in DMF (25 ml) containing potassium carbonate (940 mg, 7.48 mmol) and potassium iodide (56 mg, 0.34 mmol) was stirred at 60° C. for 2 hours. The mixture was partitioned between ethyl acetate and water. The organic layer was separated, washed with brine, dried (MgSO$_4$), the insoluble materials were removed by filtration and the volatiles were removed by evaporation. The residue was triturated with ether, collected by filtration and dried under vacuum to give 5-((3-(3-morpholinopropoxy)-4-methoxyanilino)methylene)-2,2-dimethyl-1,3-dioxane-4,6-dione 2735 mg, 5 1%).

$^1$H NMR Spectrum: (DMSOd$_6$) 1.8 (s, 6H); 2.0 (m, 2H); 2.4–2.5 (m, 4H); 2.55 (t, 2H); 3.7 (t, 4H); 3.9 (s, 3H); 4.25 (t, 2H); 7.08 (d, 1H); 7.15 (dd, 1H); 7.4 (s, 1H); 8.6 (s, 1);

A solution of 5-((3-(3-morpholinopropoxy)-4-methoxyanilino)methylene)-2,2-dimethyl-1,3-dioxane-4,6-dione (700 mg, 1.66 mmol) in phenyl ether (5 ml) was heated at reflux for 2 minutes. After cooling, the residue was triturated with ether and acetone. The solid was collected by filtration, washed with acetone followed by ether and dried under vacuum to give 6-methoxy-7-(3-morpholinopropoxy)-1,4-dihydroquinolin-4-one (207 mg, 41%).

$^1$H NMR Spectrum: (DMSOd$_6$) 2.05 (m, 2H); 2.45 (br s, 4H); 2.55 (t, 2H); 3.65 (t, 4H); 3.9 (s, 3H); 4.15 (t, 2H); 6.0 (d, 1H); 7.05 (s, 1H); 7.5 (s, 1H); 7.85 (d, 1H); 11.55 (s, 1H).

A solution of 6-methoxy-7-(3-morpholinopropoxy)-1,4-dihydroquinolin-4-one (200 mg, 0.63 mmol) in thionyl chloride (10 ml) containing DMF (3 drops) was heated at reflux for 1 hour. After removal of the volatiles by evaporation, the residue was azeotroped with toluene, triturated with ether, collected by filtration, washed with ether and dried under vacuum to give 4-chloro-6-methoxy-7-(3-morpholinopropoxy)quinoline hydrochloride (240 mg, 93%).

$^1$H NMR Spectrum: (DMSOd$_6$) 2.35–2.45 (m, 2H); 3.1–3.2 (m, 2H); 3.3 (br s, 2H); 3.5 (d, 2); 3.9 (t 2H); 4.0 (d, 2H); 4.1 (s, 3H); 4.4 (t, 2H); 7.55 (s, 1H); 7.85 (s, 1H); 8.02 (d, 1); 8.92 (d, 1H); 11.45 (br s, 1H).

EXAMPLE 8

Powdered potassium hydroxide (55 mg, 0.98 mmol) followed by 4-chloro-6,7-dimethoxyquinoline (200 mg, 0.89 mmol), (prepared as described for the starting material in Example 2), was added to 2-fluoro-5-hydroxy-4-methylphenol (600 mg, 4.2 mmol) heated at 130° C. and the mixture then stirred for 1.5 hours at 145° C. The mixture was allowed to cool then partitioned between ethyl acetate and water and the aqueous layer was adjusted to pH7 with 5M hydrochloric acid. The organic layer was separated, washed with brine, dried (MgSO$_4$) and the solvent removed by evaporation. The residue was purified by preparative reverse-phase HPLC eluting with water/methanol (90/10 to 30/o) to give 6,7-dimethoxy-4-(2-fluoro-5-hydroxy-4-methylphenoxy)quinoline (65 mg, 22%) as a white solid.

$^1$H NMR Spectrum: (DMSOd$_6$) 2.15 (s, 3H); 3.95 (s, 6H); 6.48 (d, 1H); 6.75 (d, 1H); 7.21 (d, 1H); 7.4 (s, 1H); 7.5 (s, 1H); 8.5 (d, 1H); 9.6–9.8 (br s, 1H); MS–ESI: 330 [MH]$^+$.

The starting material was prepared as follows:

A mixture of (4-fluoro-2-methyl-5-nitrophenyl) methyl carbonate (8 g, 35 mmol), (prepared as described in EP 0307777 A2), and platinum(IV)oxide (1 74 mg) in ethanol (100 ml) and ethyl acetate (70 ml) was stirred under hydrogen at 1.3 atmospheres pressure for 1.5 hours. The catalyst was removed by filtration through diatomaceous earth and the solvent removed by evaporation. The residue was purified by column chromatography eluting with petroleum ether/ethyl acetate (7/3) to give (5-amino-4-fluoro-2- methylphenyl) methyl carbonate (6.56 g, 94%) as an oil which crystallised.

¹H NMR Spectrum: (CDCl₃) 2.09 (s, 3H); 3.66 (br s, 2H); 3.90 (s, 3H); 6.54 (d, 1H); 6.83 (d, 1H).

A solution of sodium nitrite (1.63 g, 23 mmol) in water (19 ml) and ice (48 g) was added dropwise to a solution of (5-amino-4-fluoro-2-methylphenyl) methyl carbonate (3.93 g, 20 mmol) in 35% sulphuric acid (48 ml) at 0° C. The mixture was stirred at 0° C. for 30 minutes and a solution of copper(II)nitrate trihydrate (467 g, 1.93 mol) in water (780 ml) followed by copper(II)oxide (2.65 g, 18 mmol) was added. The solution was extracted with ethyl acetate, the organic layer was washed with brine, dried (MgSO₄) and the solvent removed by evaporation. The residue was purified by column chromatography eluting with petroleum ether/ethyl acetate (8/2) to give (4-fluoro-5-hydroxy-2-methylphenyl) methyl carbonate (2.13 g, 53%) as a yellow solid.

¹H NMR Spectrum: CDCl₃) 2.13 (s, 3H); 3.91 (s, 3H); 5.11 (br s, 1H); 6.78 (d, 1H); 6.93 (d, 1H).

Potassium carbonate (870 mg, 6.3 mmol) was added to a solution of (4-fluoro-5-hydroxy-2-methylphenyl) methyl carbonate (1.2 g, 6 mmol) in methanol (20 ml) and the mixture was heated at 50° C. for 1 hour. The mixture was allowed to cool, adjusted to pH3 with hydrochloric acid and extracted with ethyl acetate. The combined extracts were washed with brine, dried (MgSO₄) and the volatiles removed by evaporation. The residue was purified by column chromatography eluting with petroleum ether/ethyl acetate (7/3) to give 2-fluoro-5-hydroxy-4-methylphenol (603 mg, 70%) as a yellow solid.

¹H NMR Spectrum: CDCl₃) 2.15 (s, 3H); 4.56 (br s, 1H); 4.96 (br s, 1H); 6.46 (d, 1H); 6.82 (d, 1H).

EXAMPLE 9

As part of the procedure described in Example 8 a second compound was extracted during the column chromatography by eluting with water/methanol (90/10 to 30/70) to give 6,7-dimethoxy-4-(4-fluoro-5-hydroxy-2-methylphenoxy)quinoline (70 mg, 24%). ¹H NMR Spectrum: (DMSOd₆) 2.0 (s, 3H); 3.97 (s, 6H); 6.35 (d, 1H); 6.75 (d, 1H); 7.22 (d, 1H); 7.42 (s, 1H); 7.55 (s, 1H); 8.48 (d, 1H); MS–ESI: 330 [MH]⁺.

EXAMPLE 10

A solution of 4-chloro-6-methoxy-7-(3-morpholinopropoxy)quinoline hydrochloride (205 mg, 0.5 mmol), (prepared as described for the starting material in Example 7), and 2-fluoro-5-hydroxy-4-methylaniline (70 mg, 0.5 mmol), (prepared as described for the starting material in Example 1), in 2-pentanol (10 ml) and DMF (1 ml) was heated at reflux for 5 hours. The resulting solid was collected by filtration, partitioned between methylene chloride and aqueous sodium hydrogen carbonate solution. The organic layer was separated and purified by column chromatography eluting with methylene chloride/methanol (70/30). The purified solid product was dissolved in ethanol and concentrated hydrochloric acid (0.2 ml) added. The volatiles were removed by evaporation and the residue was recrystallised from isopropanol/ether to give 4-(2-fluoro-5-hydroxy-4-methylanilino)-6-methoxy-7-(3-morpholinopropoxy)quinoline hydrate (283 mg, 73%) as a yellow solid.

¹H NMR Spectrum: (DMSOd₆) 2.21 (s, 3H); 2.32–2.36 (m, 2H); 3.14–3.19 (m, 2H); 3.35–3.39 (m, 2H); 3.55 (d, 2H); 3.78 (t, 2H); 3.984.03 (m, 2H); 4.01 (s, 3H); 4.30–4.33 (m, 2H); 6.48 (dd, 1H); 6.90 (dd, 1H); 7.15 (dd, 1H); 7.46 (s, 1H); 8.07 (s, 1H); 8.36 (d, 1H); MS–ESI: 442 [MH]⁺;

| Elemental analysis: | Found | C 52.6 | H 6.3 | N 7.9 |
| C₂₄H₂₈N₃O₄F 2H₂O 2HCl | Requires | C 52.4 | H 6.2 | N 7.6% |

EXAMPLE 11

4-Chloro-2-fluoro-5-hydroxyaniline (97 mg, 0.6 mmol), (as described in EP 61741 A2), was added to a suspension of 4-chloro-6-methoxy-7-(2-methylthiazol-4-ylmethoxyquinoline (160 mg, 0.5 mmol) in 2-pentanol (5 ml) containing 5M hydrogen chloride in isopropanol (0.1 ml). The mixture was heated at reflux for 5 hours. The solid was collected by filtration, washed with ether and dried under vacuum to give 4-(4-chloro-2-fluoro-5-hydroxyanilino)-6-methoxy-7-(2-methylthiazol-4-ylmethoxy)quinoline hydrochloride (200 mg, 83%).

¹H NMR Spectrum: (DMSOd₆) 2.7 (s, 3H); 4.0 (s, 3H); 5.3 (s, 2H); 6.55 (dd, 1H); 7.15 (d, 1H); 7.61 (s, 1H); 7.63 (d, 1H); 7.7 (s, 1H); 8.1 (s, 1H); 8.4 (d, 1H); 10.5 (br s, 1H); 10.8 (s, 1);

| Elemental analysis: | Found | C 51.1 | H 3.9 | N 8.3 |
| C₂₁H₁₇N₃O₃ClFS 0.5H₂O 1HCl | Requires | C 51.3 | H 3.8 | N 8.5% |

The starting material was prepared as follows:

4-Chloromethyl-2-methylthiazole hydrochloride (226 mg, 1.23 mmol) was added to a suspension of 4-chloro-7-hydroxy-6-methoxyquinoline (216 mg, 1 mmol), (prepared as described for the starting material in Example 3), and potassium carbonate (483 mg, 3.5 mmol) in DMF (10 ml). The mixture was stirred for 2.5 hours at 70° C. The volatiles were removed by evaporation and the residue was partitioned between ethyl acetate and water. The organic layer was washed with brine, dried (MgSO₄), the insoluble materials were removed by filtration and the volatiles were removed by evaporation. The residue was triturated with ether, collected by filtration, washed with ether and dried under vacuum to give 4-chloro-6-methoxy-7-(2-methylthiazol-4-ylmethoxy)quinoline (352 mg, 55%).

¹H NMR Spectrum: (DMSOd₆) 2.7 (s, 3H); 3.98 (s, 3H); 5.3 (s, 2H); 7.4 (s, 11H); 7.6 (d, 1H); 7.65 (d, 2H); 8.63 (d, 1H); MS–ESI: 343 [MNa]⁺.

EXAMPLE 12

Using an analogous procedure to that described for the synthesis of Example 11, 7-benzyloxy-4-chloro-6-methoxyquinoline hydrochloride (336 mg, 1 mmol), (prepared as described for the starting material in Example 3), was reacted with 4-chloro-2-fluoro-5-hydroxyaniline (178 mg, 1.1 mmol), (as described in EP 61741 A2), in 2-butanol (15 ml) to give 7-benzyloxy-4-(4-chloro-2-fluoro-5-hydroxyanilino)-6-methoxyquinoline hydrochloride (200 mg, 43%).

¹H NMR Spectrum: (DMSOd6) 4.01 (s, 3H); 6.5 (m, 1H); 7.15 (d, 1H); 7.35–7.5 (m, 4H); 7.55 (d, 4H); 7.65 (d, 1H); 8.15 (s, 1H); 8.4 (d, 1H); MS–ESI: 425 [MH]⁺.

EXAMPLE 13

To a suspension of 4-chloro-6-methoxy-7-(3-(3-pyridyl) propoxy)quinoline (150 mg, 0.46 mmol) in 2-pentanol (5 ml) was added 4-chloro-2-fluoro-5-hydroxyaniline (91 mg, 0.55 mmol), (as described in EP 61741 A2), and 5M hydrogen chloride in isopropanol (0.1 ml). The mixture was heated at reflux for 15 minutes and DMF (3 ml) was added. The mixture was heated at reflux for 5 hours and the volatiles were removed by evaporation. The residue was triturated with isopropanol, collected by filtration and dried under vacuum to give 4-(4-chloro-2-fluoro-5-hydroxyanilino)-methoxy-7-(3-(3-pyridyl)propoxy)quinoline (150 mg, 62%).

$^1$H NMR Spectrum: (DMSOd$_6$) 2.25 (t, 2H); 3.05 (t, 2H); 4.0 (s, 3H); 4.25 (t, 2H); 6.5 (dd, 1H); 7.2 (d, 1H); 7.5 (s, 1H); 7.6 (d, 1H); 7.9 (m, 1H); 8.2 (s, 1H); 8.35–8.45 (m, 2H); 8.75 (d, 1H); 8.85 (s, 1H); 10.7 (s, 1H); 10.8 (s, 1H); MS-ESI: 454 [MH]$^+$;

| Elemental analysis: | Found | C 53.3 | H 4.7 | N 7.5 |
| --- | --- | --- | --- | --- |
| C$_{24}$H$_{21}$N$_3$O$_3$ClF | Requires | C 53.2 | H 4.8 | N 7.7% |
| 1.3H$_2$O 1.8HCl 0.08isopropanol | | | | |

The starting material was prepared as follows:

Diethyl azodicarboxylate (340 mg, 2 mmol) was added dropwise to a solution of triphenylphosphine (520 mg, 2 mmol), 4-chloro-7-hydroxy-6-methoxyquinoline (265 mg, 1.26mmol), (prepared as described for the starting material in Example 3), and 3-(3-pyridyl)-1-propanol (170 mg, 1.24 mmol) in methylene chloride (10 ml). The mixture was stirred for 1 hour at ambient temperature. The volatiles were removed by evaporation and the residue was purified by column chromatography eluting with methylene chloride/acetonitrile/methanol (50/45/5 increasing to 50/40/10). The purified product was triturated with ether, collected by filtration and dried under vacuum to give 4-chloro-6-methoxy-7-(3-(3-pyridyl)propoxy)quinoline (300 mg, 72%).

$^1$H NMR Spectrum: (DMSOd$_6$) 2.15 (m, 2H); 2.82 (t, 2H); 4.0 (s, 3H); 4.2 (t, 2H); 7.3 (dd, 1H); 7.39 (s, 1H); 7.44 (s, 1H); 7.55 (d, 1H); 7.7 (td, 1H); 8.4 (d, 1H); 8.5 (s, 1H); 8.6 (d, 1H).

EXAMPLE 14

4-Chloro-2-fluoro-5-hydroxyaniline (194 mg, 1.2 mmol), (as described in EP 61741 A2), was added to a suspension of 4-chloro-6,7-dimethoxy-3-fluoroquinoline (241 mg, 1 mmol) in 2-pentanol (5 ml). After refluxing for 15 hours, the precipitate was collected by filtration, washed with isopropanol and dried under vacuum. The solid was partitioned between ethyl acetate and aqueous sodium hydrogen carbonate. The organic layer was washed with water, brine, dried (MgSO$_4$) and the volatiles were removed by evaporation. The residue was purified by column chromatography eluting with methylene chloride/methanol 95/5. The purified product was dissolved in methylene chloride/isopropanol and 5M hydrogen chloride in isopropanol (0.5 ml) was added. After evaporation of the methylene chloride, the precipitate was collected by filtration, washed with isopropanol, followed by ether and dried under vacuum to give 6,7-dimethoxy-3-fluoro-4-(4-chloro-2-fluoro-hydroxyanilino)quinoline hydrochloride (150 mg, 37%).

$^1$H NMR Spectrum: (DMSOd$_6$) 3.98 (s, 3H); 3.99 (s, 3H); 7.12 (d, 1H); 7.46 (s, 1H); 7.49 (d, 1H); 8.04 (s, 1H); 8.96 (d, 1H); 10.38 (br s, 1H); 10.6 (br s, 1H); MS-ESI: 367 [MH]$^+$;

| Elemental analysis: | Found | C 49.8 | H 3.7 | N 6.6 |
| --- | --- | --- | --- | --- |
| C$_{17}$H$_{14}$N$_2$O$_3$ClF$_2$ 0.2H$_2$O 1HCl | Requires | C 49.8 | H 3.7 | N 6.7% |
| 0.07methylene chloride | | | | |
| 0.09isopropanol | | | | |

The starting material was prepared as follows:

Nitromethane (4 g, 66 mmol) was added dropwise to a solution of sodium hydroxide (8 g, 0.2 mol) in water (16.4 ml) while maintaining the temperature in the range 25 to 30° C. After the addition was complete, the mixture was heated at 40° C. for 10 minutes. After cooling to 25° C., further nitromethane (4 g, 66 mmol) was added. The mixture was heated at 40 to 45° C. followed by 5 minutes at 50 to 55° C. After cooling the mixture was poured onto ice (1.8 g) and concentrated hydrochloric acid (18 ml) was added. This solution was added to a solution of anthranilic acid (11.8 g, 60 mmol) in water (120 ml) containing concentrated hydrochloric acid (5.49 ml) and stirring was continued overnight. The precipitate was collected by filtration, washed with water, and dried under vacuum to give 4,5-dimethoxy-2-(β-nitroethylideneamino)benzoic acid (14 g, 87%). MS-EI: 268 [M.]$^+$.

A suspension of )benzoic acid (14 g, 52 mmol) in acetic anhydride (70 ml) was heated at reflux until it had completely dissolved. After cooling to ambient temperature, potassium acetate (5.7 g, 58 mmol), (freshly dried at 110° C. under vacuum), was added. The mixture was heated at reflux for 15 minutes and stirred overnight at ambient temperature. The precipitate was collected by filtration, washed thoroughly with acetic acid followed by water and dried under vacuum at 110° C to give 6,7-dimethoxy-3-nitro-1,4-dihydroquinolin-4-one (2.5 g, 19%).

$^1$H NMR Spectrum: (D$_2$O) 3.7 (2s, 6H); 6.4 (s, 1H); 7.0 (s, 1H); 8.5 (s, 1H) MS-EI: 250 [M.]$^+$.

Phosphorus oxychloride (1.69 g, 11 mmol) was added to a suspension of 6,7-dimethoxy-3-nitro-1,4-dihydroquinolin-4-one (2.5 g, 10 mmol) in anhydrous DMF (20 ml) and the mixture was heated at 100° C. for 30 minutes. The mixture was cooled and poured onto ice/water. The precipitate was collected by filtration, washed with water and dried under vacuum to give 4-chloro-6,7-dimethoxy-3-nitroquinoline (2.25 g, 83%).

$^1$H NMR Spectrum: CDCl$_3$) 4.09 (s, 3H); 4.1 (s, 3H); 7.48 (s, 1H); 7.56 (s, 1H); 9.13 (s, 1H); MS-EI: 268 [M.]$^+$.

A solution of 4-chloro-6,7-dimethoxy-3-nitroquinoline (1.07 g, 4 mmol) in ethanol (40 ml) containing Raney Nickel (1 g) was stirred under hydrogen at atmospheric pressure for 3 hours. The volatiles were removed by evaporation. The residue was triturated with petroleum ether, collected by filtration and dried under vacuum to give 3-amino-4-chloro-6,7-dimethoxyquinoline (925 mg, 97%).

$^1$H NMR Spectrum: CDCl$_3$) 3.99 (s, 3H); 4.05 (s, 3H); 4.15 (br s, 2H); 7.25 (s, 1H); 7.32 (s, 1H); 8.35 (s, 1H);

| Elemental analysis: | Found | C 55.1 | H 4.9 | N 11.7 |
| --- | --- | --- | --- | --- |
| C$_{11}$H$_{11}$N$_2$O$_2$Cl | Requires | C 55.4 | H 4.6 | N 11.7% |

A 50% aqueous solution of hydrogen tetrafluoroborate (1.5 ml, 12 mmol) was added to 3-amino-4-chloro-6,7-dimethoxyquinoline (716 mg, 3 mmol) in THF (12 ml) at 0° C. A solution of sodium nitrate (228 mg, 3.3 mmol) in water (1 ml) was added dropwise with vigorous stirring. After stirring for 15 minutes at 0° C., the precipitate was collected by filtration, washed with THF and dried under vacuum to give 4-chloro-3-diazonium-6,7-dimethoxyquinoline tetrafluoroborate (950 mg, 95%).

$^1$H NMR Spectrum: (DMSOd$_6$) 3.95 (s, 3H); 4.0 (s, 3H); 7.35 (s, 1H); 7.5 (s, 1H); 9.4 (s, 1H).

4-Chloro-3-diazonium-6,7-dimethoxyquinoline tetrafluoroborate (1.2 g, 3.55 mmol) was melted by heating it to approximately 180° C. After fusion, the residue was dissolved in methylene chloride (2 ml) and ether was added. Any insoluble material was removed by filtration and the volatiles were removed by evaporation. The solid was triturated with methylene chloride, collected by filtration and dried under vacuum to give 4-chloro-6,7-dimethoxy-3-fluoroquinoline (445 mg, 52%).

m.p. 159–160° C.; $^1$H NMR Spectrum; (DMSOd$_6$; CF$_3$COOD) 3.95 (s, 3H); 4.05 (s, 3H); 7.35 (s, 1H); 7.5 (s, 1H); 8.9 (s, 1H); MS—Cl: 367 [MH]$^+$;

| Elemental analysis: | Found | C 54.5 | H 4.0 | N 5.8 |
|---|---|---|---|---|
| C$_{11}$H$_9$NO$_2$ClF | Requires | C 54.7 | H 3.8 | N 5.8% |

A solution of 4,7-dichloroquinoline (198 mg, 1 mmol) and 2-fluoro-5-hydroxy-4-methylaniline (1 69 mg, 1.2 mmol), (prepared as described for the starting material in Example 1), in 2-pentanol (5 ml) containing 5M hydrochloric acid in isopropanol (0.5 ml) was heated at reflux for 2 hours. The volatiles were removed by evaporation and the residue was triturated with ether. The solid was collected by filtration, washed with isopropanol, followed by ether and dried under vacuum to give 7-chloro-4-(2-fluoro-5-hydroxy-4-methylanilino)quinoline hydrochloride (300 mg, 88%).

$^1$H NMR Spectrum: (DMSOd$_6$) 2.19 (s, 31H); 6.55 (m, 1H): 6.9 (d, 1H); 7.25 (d, 1H); 7.9 (d, 1H); 8.15 (s, 1H): 8.56 (d, 1H): 8.8 (d, 1H); 9.9 (s, 1H): 10.9 (s, 1H); MS–ESI: 303 [MH]$^+$;

| Elemental analysis: | Found | C 56.4 | H 4.1 | N 8.1 |
|---|---|---|---|---|
| C$_{16}$H$_{12}$N$_2$OClF 1HCl | Requires | C 56.7 | H 3.9 | N 8.3% |

EXAMPLE 16

A suspension of 4-chloro-6,7-dimethoxyquinoline (200 mg, 0.9 mmol), (prepared as described for the starting material in Example 2), and 4-bromo-2-fluoro-5-hydroxyaniline (206 mg, 1 mmol), as described in EP 61741 A2), in 2-pentanol (8 ml) was heated at reflux for 4 hours. The precipitate was collected by filtration, washed with isopropanol, followed by ether, and dried under vacuum to give 4-(4-bromo-2-fluoro-5-hydroxyanilino)-6,7-dimethoxyquinoline (225 mg, 58%).

$^1$H NMR Spectrum: (DMSOd$_6$) 3.98 (s, 3H); 4.0 (s, 3H); 6.55 (m, 1H); 7.15 (d, 1H); 7.43 (s, 1H), 7.75 (d, 1H); 8.1 (s, 1H); 8.4 (d, 1H); 10.5 (br s, 1H); 10.8 (s, 1H); MS–ESI: 395 [MH]$^+$.

EXAMPLE 17

A solution of 3-acetoxy-4-methylaniline (182 mg, 1.1 mmol) and 7-benzyloxy-4 4-chloro-6-methoxyquinoline hydrochloride (336 mg, 1 mmol), (prepared as described for the starting material in Example 3), in isopropanol (5 ml) was heated at reflux for 1 hour. The volatiles were removed by evaporation. The residue was partitioned between ethyl acetate and water and the aqueous layer was adjusted to pH7–8 with aqueous sodium hydrogen carbonate. The organic layer was separated, washed with water, brine, dried (MgSO$_4$) and the volatiles were removed by evaporation. The residue was purified by column chromatography eluting with methylene chloride/methanol (95/5 increasing to 85/15). The purified product was dissolved in methylene chloride/methanol and 5M hydrochloric acid in isopropanol (0.5 ml) was added. Methylene chloride was removed by evaporation. The precipitate was collected by filtration, washed with isopropanol and dried under vacuum to give 4-(3-acetoxy-4-methylanilino)-7-benzyloxy-6-methoxyquinoline hydrochloride (144 mg, 31%).

m.p. 230–232° C.; $^1$H NMR Spectrum: (DMSOd$_6$) 2.19 (s, 3H); 2.33 (s, 3H); 3.99 (s, 3H); 5.3 (s, 2H); 6.7 (d, 1H); 7.22 (s, 1H); 7.3 (d, 1H); 7.4–7.6 (m, 8H); 8.1 (s, 1H); 8.4 (d, 1H); MS–ESI: 429 [MH]$^+$;

| Elemental analysis: | Found | C 66.9 | H 5.8 | N 5.8 |
|---|---|---|---|---|
| C$_{26}$H$_{24}$N$_2$O$_4$ 1HCl | Requires | C 67.2 | H 5.4 | N 6.0% |

The starting material was prepared as follows:

To a mixture of 2-methyl-5-nitrophenol (2.5 g, 16.3 mmol) and 1M aqueous sodium hydroxide (24.5 ml) at ambient temperature was added acetic anhydride (1.9 ml 120.3 mmol). The mixture was stirred for 40 minutes, the solid was removed by filtration and the filtrate was extracted with ethyl acetate. The organic layers were combined, washed with an aqueous saturated sodium chloride solution, dried (MgSO$_4$) and the volatiles were removed by evaporation to yield 2-acetoxy-4-nitrotoluene (3.1 g, 100%). A mixture of this material (3.1 g, 15.9 mmol) and 10% palladium-on-charcoal catalyst (0.12 g) in ethyl acetate (50 ml) was stirred at ambient temperature under hydrogen for 2 hours. The catalyst was removed by filtration and the volatiles were removed by evaporation to give 3-acetoxy-4-methylaniline (2.45 g, 94%).

EXAMPLE 18

4-Dimethylaminopyridine (12 mg, 0.1 mmol) and acetic anhydride (122 mg, 1.2 mmol) were added to a suspension of 7-benzyloxy-4-(4-chloro-2-fluoro-5-hydroxyanilino)-6-methoxyquinoline hydrochloride (461 mg, 1 mmol), (prepared as described in Example 12). The mixture was heated at reflux for 1 hour and the volatiles were removed by evaporation. The residue was triturated with water and the resulting precipitate was collected by filtration and dried under vacuum to give 4-(5-acetoxy-4-chloro-2-fluoroanilino)-7-benzyloxy-6-methoxyquinoline (480 mg, 95%).

$^1$H NMR Spectrum: (DMSOd$_6$) 2.3 (s, 3H); 4.0 (s, 3H); 5.32 (s, 2H); 6.6 (d, 1H); 7.35–7.5 (m, 3H); 7.5–7.6 (m, 3H); 7.65 (d, 1H); 7.95 (d, 1H); 8.15 (s, 1H); 8.45 (d, 1H); 10.65 (br s, 1H); MS–ESI: 467 [MH]$^+$.

EXAMPLE 19

A suspension of 7-benzyloxy-4-chloro-6-methoxyquinoline hydrochloride (1.68, 5 mmol), (prepared as described for the starting material in Example 3), and 4-bromo-2-fluoro-5-hydroxyaniline (1.03 g, 5 mmol), (as described in EP 61741 A2), in 2-pentanol (25 ml) was heated at reflux for 3 hours under nitrogen. The precipitate was collected by filtration, washed with isopropanol, followed by ether and dried under vacuum to give 7-benzyloxy-4-(4-bromo-2-fluoro-5-hydroxyanilino)-6-methoxyquinoline hydrochloride (1.45 g, 57%).

$^1$H NMR Spectrum: (DMSOd$_6$) 4.01 (s, 3H); 5.33 (s, 2H); 6.5 (dd, 1H); 7.13 (d, 1H); 7.35–5 7.5 (m, 3H); 7.5–7.6 (m, 3H); 7.75 (d, 1H); 8.12 (s, 1H); 8.4 (d, 1H). 10.55 (br s, 1H); 10.85 (s, 1H); MS–ESI: 469 [MH]$^+$;

| Elemental analysis: | Found | C 54.5 | H 3.9 | N 5.3 |
|---|---|---|---|---|
| C$_{23}$H$_{18}$ N$_2$O$_3$BrF 0.26H$_2$O 1HCl | Requires | C 54.1 | H 3.9 | N 5.5% |

EXAMPLE 20

A 1M solution of tetrabutylammonium fluoride in THF (0.4 ml 0.4 mmol) was added to a solution of 4-(4-chloro-5-diphenyl-t-butylsilyloxy-2-fluoroanilino)-6-methoxy-7-(4-pyridylmethoxy)quinoline (226 mg, 0.34 mmol) in THF (3 ml). After stirring for 30 minutes at ambient temperature, the mixture was diluted with water and the precipitate was collected by filtration. The precipitate was dissolved in a mixture of methylene chloride/methanol and 7M hydrogen chloride in isopropanol (1 ml) was added. The volatiles were removed by evaporation and the residue was triturated with methylene chloride, collected by filtration, washed with ether and dried under vacuum to give 4-(4-chloro-2-fluoro-5-hydroxyanilino)-6-methoxy-7-(4-pyridylmethoxy) quinoline hydrochloride (150 mg, 88%).

$^1$H NMR Spectrum: (DMSOd$_6$; CF$_3$COOD) 4.08 (s, 3H); 5.74 (s, 2H); 6.6 (m, 1H); 7.15 (d, 1H); 7.52 (s,: 11H); 7.65 (d, 1H); 8.1–8.2 (m, 31H); 8.45 (d, 1H); 9.1 (d, 2H); MS–ESI: 426 [MH]$^-$;

| Elemental analysis: | Found | C 52.3 | H 4.3 | N 8.0 |
|---|---|---|---|---|
| C$_{22}$H$_{17}$N$_3$O$_3$ClF 0.74H$_2$O 2HCl | Requires | C 51.6 | H 4.0 | N 8.2% |

The starting material was prepared as follows:

A mixture of 7-benzyloxy-4-(4-chloro-2-fluoro-5-hydroxyanilino)-6-methoxyquinoline (2.35 g, 7 mmol), (prepared as described in Example 12), imidazole (1.2 g, 17.5 mmol), t-butyldiphenylsilyl chloride (2.1 g, 7.7 mmol) and DMAP (20 mg) in DMF (10 ml) was stirred for 2 hours, then water was added. The precipitate was collected by filtration, suspended in ethyl acetate (30 ml)/water (10 ml) and stirred for 15 minutes at ambient temperature. The solid was collected by filtration, washed with water and dried under vacuum to give 7-benzyloxy-4-(4-chloro-5-diphenyl-t-butylsilyloxy-2-fluoroanilino)-6-methoxyquinoline (2 g, 43%).

$^1$H NMR Spectrum: (DMSOd$_6$) 1.09 (s, 9H); 3.9 (s, 3H); 5.3 (s, 2H); 6.05 (d, 1H); 6.52 (d, 1H); 7.35–7.55 (m, 13H); 7.7 (m, 3H); 7.85 (d, 1H); 7.9 (s, 1H); 8.25 (d, 1H); MS–ESI: 573 [MH]$^+$.

A solution of 7-benzyloxy-4-(4-chloro-5-diphenyl-t-butylsilyloxy-2-fluoroanilino)-6-methoxyquinoline (2 g, 3 mmol) in a mixture of DMF (20 ml), methanol (20 ml) and ethyl acetate (20 ml) containing 10% palladium-on-charcoal catalyst (400 mg) was stirred under hydrogen at 1.7 atmospheres pressure for 2 hours. The solids were removed by filtration and the volatiles were removed by evaporation. The residue was purified by column chromatography eluting with methylene chloride/methanol (95/5 increasing to 90/10) to give an oil that crystallised from ether. The solid was collected by filtration and dried under vacuum to give 4-(4-chloro-5-diphenyl-t-butylsilyloxy-2-fluoroanilino)-7-hydroxy-6-methoxyquinoline (1.65 g, 95%).

$^1$H NMR Spectrum: CDCl$_3$) 1.12 (s, 9H); 3.76 (s, 3H); 5.6 (d, 1H); 6.6 (d, 1H); 7.2 (d, 1H); 7.3–7.45 (m, 8H); 7.6 (d 1H); 7.7 (d, 4H).

Diethyl azodicarboxylate (218 mg, 1.25 mmol) was added dropwise to a mixture of 4-(4-chloro-5-diphenyl-t-butylsilyloxy-2-fluoroanilino)-7-hydroxy-6-methoxyquinoline (286 mg, 0.5 mmol), triphenylphosphine (328 mg, 1.25 mmol) and 4-pyridylcarbinol (65 mg, 0.6 mmol) in methylene chloride (10 ml) at 0° C. under argon. The mixture was stirred for 45 minutes at ambient temperature and poured onto a column of silica. The product was purified by column chromatography eluting with methylene chloride/acetonitrile/methanol (1/1/0 increasing to 50/30/20) to give 4-(4-chloro-5diphenyl-t-butylsilyloxy-2-fluoroanilino)-6-methoxy-7-(4-pyridylmethoxy)quinoline (100 mg, 30%).

$^1$H NMR Spectrum: (DMSOd$_6$) 1.07 (s, 9H); 3.89 (s, 3H); 5.3 (s, 2H); 5.84 (d, 1H); 6.48 (d, 1H); 7.23 (s, 1H); 7.4–7.52 (m, 8H); 7.6 (s, 1H); 7.6 –7.7 (m, 5H); 8.0 (d, 1H); 8.6 (d, 2H); MS–ESI: 664 [MH]$^+$.

EXAMPLE 21

Using an analogous procedure to that described for Example 20, 4-(4-chloro-5-diphenyl-t-butylsilyloxy-2-fluoroanilino)-7-ethoxy-6-methoxyquinoline (1 70 mg, 0.28 mmol) was reacted with tetrabutylammonium fluoride (0.34 ml, 0.34 mmol) to give 4-(4-chloro-2-fluoro-5-hydroxyanilino)-7-ethoxy-6-methoxyquinoline hydrochloride (75 mg, 67%).

$^1$H NMR Spectrum: (DMSOd$_6$) 1.44 (t, 3H); 4.0 (s, 3H); 4.22 (q, 2H); 6.55 (dd, 1H); 7.15 (d, 1H); 7.4 (s, 1H); 7.65 (d, 1H); 8.05 (s, 1H); 8.4 (d, 1H); 10.45 (br s, 1H); 10.8 (s, 1H); MS–ESI: 363 [MH]$^+$.

The starting material was prepared as follows:

As parts of the procedure described for the starting material in Example 20 a second compound was extracted during the column chromatography by eluting with methylene chloride/acetonitrile/methanol (1/1/0 increasing to 50/30/20) to give 4-(4-chloro-5-diphenyl-t-butylsilyloxy-2-fluoroanilino)-7-ethoxy-6-methoxyquinoline (170 mg, 57%).

$^1$H NMR Spectrum: (DMSOd$_6$) 1.08 (s, 9H); 1.4 (t, 3H); 3.85 (s, 3H); 4.15 (q, 2H); 5.8 (d, 1H); 6.5 (d, 1H); 7.2 (s, 1H): 7.3 (d, 1H); 7.4–7.7 (m, 1H); 8.0 (d, 1H); 8.55 (d, 1H); MS–ESI: 601 [MH]$^-$.

1M Tetrabutylammonium fluoride in THF (0.5 ml, 0.5 mmol) was added to a solution of 4-(4-chloro-5-diphenyl-t-butylsilyloxy-2-fluoroanilino)-6-methoxy-7-(1-methylimidazol-2-ylmethoxy)quinoline (280 mg, 0.42 mmol) in THF (3 ml). The mixture was stirred for 1 hour at ambient temperature and water was added. THF was removed by evaporation and the precipitate was collected by filtration, washed with water and dried under vacuum. The solid was dissolved in methylene chloride/methanol and 5M hydrogen chloride in methanol (0.3 ml) was added. The volatiles were removed by evaporation and the solid was triturated with methylene chloride, collected by filtration, washed with methylene chloride followed by ether and dried under vacuum to give 4-(4-chloro-2-fluoro-5-hydroxyanilino)-6-methoxy-7-(1-methylimidazol-2-ylmethoxy)quinoline hydrochloride (120 mg, 57%).

$^1$H NMR Spectrum: (DMSOd$_6$) 3.9 (s, 3H); 4.0 (s, 3H); 5.7 (s, 2H); 6.55 (dd, 1H); 7.2 (d, 1H); 7.63 (d, 1H); 7.69 (s, 1H): 7.73 (s, 1H); 7.78 (s, 1H); 8.29 (s, 1H); 8.44 (d, 1H); 10.84 (br s, 2H); MS–ESI: 429 [MH]$^-$;

| Elemental analysis: | Found | C 49.4 | H 4.4 | N 10.7 |
|---|---|---|---|---|
| C$_{21}$H$_{18}$N$_4$O$_3$ClF 0.71H$_2$O 1.9HCl | Requires | C 49.4 | H 4.2 | N 11.0% |

The starting material was prepared as follows:

1,1'-(Azodicarbonyl)dipiperidine (756 mg, 3 mmol) was added to a mixture of 4-(4-chloro-5-diphenyl-t-butylsilyloxy-2-fluoroanilino)-7-hydroxy-6-methoxyquinoline (572 mg, 1 mmol), (prepared as described for the starting material in Example 20), tributylphosphine (300 mg, 3 mmol), and 2-hydroxymethyl-1-methylimidazole (134 mg, 1.2 mmol), (J. Chem. Soc. 1927, 3128–3136), in a mixture of methylene chloride (20 ml) and toluene (20 ml). The mixture was stirred at ambient temperature for 1 hour and acetic acid (120 mg, 2 mmol) was added, followed by ether. The insoluble materials were removed by filtration and the volatiles were removed by evaporation. The residue was purified by column chromatography eluting with methylene chloride/acetonitrile/methanol (50/40/10 increasing to 50/30/20) to give 4-(4-chloro-5-diphenyl-t-butylsilyloxy-2-fluoroanilino)-6-methoxy-7-(1-methylimidazol-2-ylmethoxy)quinoline (280 mg, 42%).

$^1$H NMR Spectrum: (DMSOd$_6$) 1.1 (s, 9H); 3.7 (s, 3H); 3.9 (s, 3H); 5.3 (s, 2H); 5.95 (d, 1H); 6.5 (d, 1H); 6.9 (s, 1H); 7.2 (s, 1H); 7.4–7.5 (m, 7H); 7.6 (s, 1H); 7.65–7.75 (m, 5H); 8.1 (d, 1); MS–ESI: 667 [MH]$^+$.

EXAMPLE 23

Using an analogous procedure to that described for Example 22, 4-(4-chloro-5-diphenyl-t-butylsilyloxy-2-fluoroanilino)-6-methoxy-7-(2-morpholinoethoxy)quinoline (140 mg, 0.2 mmol) was reacted with 1M tetrabutylammonium fluoride (0.3 ml, 0.3 mmol) to give 4-(4-chloro-2-fluoro-5-hydroxyanilino)-6-methoxy-7-(2-morpholinoethoxy)quinoline hydrochloride (65 mg, 61%).

$^1$H NMR Spectrum: (DMSOd$_6$; CF$_3$COOD) 3.35 (t, 2H); 3.64 (d, 2H); 3.7–3.85 (m, 4H); 4.04 s, 3H); 4.40 (br s, 2H); 4.65 (t, 2H); 6.6 (dd, 1H); 7.15 (d, 1H); 7.5 (s, 1H); 7.6 (d, 1H); 8.1 (s, 1); 8.5 (d, 1H); MS–ESI: 448 [MH]$^+$.

The starting material was prepared as follows:

1,1'-(Azodicarbonyl)dipiperidine (378 mg, I.5 mmol) was added in portions to 4-(4-chloro-5-diphenyl-t-butylsilyloxy-2-fluoroanilino)-7-hydroxy-6-methoxyquinoline (286 mg, 0.5 mmol), (prepared as described for the starting material in Example 20), 4-(2-hydroxyethyl)morpholine (98 mg, 0.6 mmol) and tributylphosphine (300 mg, 1.5 mmol) in methylene chloride (10 ml) at 0° C. under argon. The mixture was stirred for 1 hour at ambient temperature and was diluted with ether. The precipitate was collected by filtration, washed with ether and dried under vacuum. The solid was purified by column chromatography eluting with methylene chloride/methanol (95/5 increasing to 85/15) to give 4-(4-chloro-5-diphenyl-t-butylsilyloxy-2-fuoroanilino)-6-methoxy-7-(2-morpholinoethoxy)quinoline (150 mg, 43%).

$^1$H NMR Spectrum. DMSOd$_6$) 1.1 (s, 9H); 2.78 (t, 2H); 3.1–3.3 (m, 2H); 3.55 (t, 2H); 3.6 (t, 4H); 3.85 (s, 3H); 4.2 (t, 2H); 5.85 (d, 1H); 6.5 (d, 1H); 7.2 (s, 1H); 7.4–7.55 (m, 8H); 7.65–7.7 (m, 5H); 8:.0 (d, 1H).

EXAMPLE 24

A suspension of 4-chloro-6,7-dimethoxyquinoline (300 mg, 1.3 mmol), (prepared as described for the starting material in Example 2), and 3-hydroxy-4-methylaniline (181 mg, 1.47 mol) in 2-butanol (13 ml) containing 5M hydrogen chloride in isopropanol (3 drops) was heated at 110° C. for 5.5 hours. Ethanol was added until the solids were completely dissolved and the solution was cooled to 0° C. Ether was added and the precipitate was collected by filtration, washed with ether and dried under vacuum to give 6,7-dimethoxy-4-(3-hydroxy-4-methylanilino)quinoline (209 mg, 46%).

$^1$H NMR Spectrum: (DMSOd$_6$) 2.2 (s, 3H); 3.99 (s, 3H); 4.0 (s, 3H); 6.7 (d, 1H); 6.8 (d, 1H); 6.9 (s, 1H); 7.25 (d, 1H); 7.45 (s, 1H); 8.1 (s, 1H); 8.32 (d, 1H); 9.9 (s, 1H); MS–ESI: 311 [MH]$^+$.

EXAMPLE 25

A suspension of 4-chiloro-2-fluoroaniline (164 μl, 1.4 mmol) and 4-chloro-6,7-dimethoxyquinoline (300 mg, 1.3 mmol), (prepared as described for the starting material in Example 2), in DMF (6 ml) was heated at reflux for 4 hours and the solvent was removed by evaporation. The residue was triturated with ether and collected by filtration. The solid was washed with water, ether and dried under vacuum to give 4-(4-chloro-2-fluoroanilino)-6,7-dimethoxyquinoline hydrochloride (98 mg, 20%).

$^1$H NMR Spectrum: (DMSOd$_6$) 4.00 (s, 3H); 4.02 (s, 3H); 6.55 (d, 1H); 7.5 (s, 1H): 7.55 (d, 1H): 7.65 (t, 1H); 7.8 (d, 1H); 8.15 (s, 1H); 8.42 (d, 1H); MS–ESI: 333 [MH]$^+$.

EXAMPLE 26

Potassium hydroxide (14 mg, 0.25 mmol) and 4-chloro-6,7-dimethoxyquinoline (50 mg, 0.22 mmol), (prepared as described for the starting material in Example 2), were added to 1,3-dihydroxybenzene (1 g, 9 mmol) melted at 140° C. under argon. After stirring for 1 hour at 140° C., the mixture was partitioned between ethyl acetate and water and 2M hydrochloric acid was added to adjust the aqueous phase to pH4. The organic layer was washed with water, brine, dried (MgSO$_4$) and the volatiles were removed by evaporation. The residue was purified by column chromatography eluting with methylene chloridelethyl acetate (6/4 increasing to 3/7). The purified product was triturated with ether, collected by filtration and dried under vacuum to give 6,7-dimethoxy-4-(3-hydroxyphenoxy)quinoline (51 mg 78%).

$^1$H NMR Spectrum: (DMSOd$_6$) 3.93 (s, 3H); 3.96 (s, 3H); 6.55 (d, 1H); 6.6 (s, 1H); 6.7 (d, 1H); 6.75 (d, 1H); 7.3 (t, 1H); 7.42 (s, 1H); 7.5 (s, 1H); 8.52 (d, 1H); 9.8–9.9 (br s, 1H); ESI: 297 [M.]$^-$;

| Elemental analysis: | Found | C 68.0 | H 5.5 | N 4.4 |
|---|---|---|---|---|
| C$_{17}$H$_{15}$NO$_4$0.15ethyl acetate | Requires | C 68.1 | H 5.3 | N 4.5% |

EXAMPLE 27

A suspension of 4-chloro-6,7-dimethoxyquinoline (200 mg, 0.89 mmol), (prepared as described for the starting material in Example 2), and 6-aminoindazole (131 mg, 0.98 mmol) in DMF (2.5 ml) was heated at 140° C. for 1.5 hours. The solid was collected by filtration, washed with isopropanol and dried under vacuum to give 6,7-dimethoxy-4-(1H-indazol-6-ylamino)quinoline hydrochloride (171 mg, 54%).

¹H NMR Spectrum: (DMSOd₆) 3.99 (s, 3H); 4.01 (s, 3H); 6.8 (d, 1H); 7.2 (d, 1H); 7.45 (s, 1H); 7.65 (s, 1H); 7.95 (d, 1H); 8.18 (br s, 2H); 8.35 (d, 1H); MS–ESI: 321 [MH]⁺.

EXAMPLE 28

Using an analogous procedure to that described in Example 26, 4-chloro-6,7-dimethoxyquinoline (170 mg, 0.76 mmol), (prepared as described for the starting material in Example 2), was reacted with 4-chloro-2-fluorophenol (600 mg, 4.1 mmol) and potassium hydroxide (49 mg, 0.87 mmol) for 3 hours to give, after purification, 4-(4-chloro-2-fluorophenoxy)-6,7-dimethoxyquinoline (119 mg, 47%).

¹H NMR Spectrum: (DMSOd₆) 3.95 (s, 3H); 3.96 (s, 3H); 6.55 (d, 1H): 7.45 (s, 1H); 7.48 (d, 1H); 7.52 (s, 1H); 7.55 (t, 1H); 7.78 (d, 1H); 8.52 (d, 1H); MS–ESI: 334 [MH]⁺.

EXAMPLE 29

Using an analogous procedure to that described in Example 25, 4-chloro-6-methoxy-7-(2-methoxyethoxy) quinoline hydrochloride (500 mg, 1.64 mmol), (prepared as described for the starting material in Example 5), was reacted with 4-chloro-2-fluoro-5-hydroxyaniline (270 mg, 1.64 mmol), (as described in EP 61741 A2), for 5 hours to give 4-(4-chloro-2-fluoro-5-hydroxyanilino)-6-methoxy-7-(2-methoxyethoxy)quinoline hydrochloride (475 mg, 67%).

¹H NMR Spectrum: (DMSOd₆) 3.37 (s, 3H); 3.8 (t, 2H); 4.03 (s, 3H); 4.31 (t, 2H); 6.5 (m, 1H); 7.2 (d, 1H); 7.49 (s, 1H); 7.64 (d, 1H); 8.16 (s, 1H); 8.40 (d, 1H); 10.66 (s, 1H); 10.82 (s, 1H); MS–ESI: 393 [MH]⁺;

| Elemental analysis: | Found | C 52.7 | H 4.6 | N 6.4 |
|---|---|---|---|---|
| $C_{19}H_{18}N_2O_4ClF$ 1HCl | Requires | C 53.1 | N 4.4 | N 6.5% |

EXAMPLE 30

A solution of 4-chloro-6-methoxy-7-(2-methoxyethoxy) quinoline hydrochloride (300 mg, 1 mmol) (prepared as described for the starting material in Example 5), and 6-aminoindazole (130 mg, 0.97 mmol) in 2-pentanol (10 ml) was heated at reflux for 3 hours. The precipitate was collected by filtration, washed with acetone and dried under vacuum. The residue was purified by reverse phase column chromatography eluting with methanol/water containing 1% acetic acid (40/60). Concentrated hydrochloric acid (5 drops) was added to the combined fractions of the product and the volatiles were removed by evaporation to give 4-(1H-indazol-6-ylamino)-6-methoxy-7-(2-methoxyethoxy) quinoline hydrochloride (213 mg, 54%).

¹H NMR Spectrum: (DMSOd₆) 3.37 (s, 3H); 3.8 (t, 2H); 4.04 (s, 3H); 4.3 (t, 2H); 6.8 (d, 1H); 7.2 (d, 1H); 7.5 (s, 1H); 7.68 (s, 1H); 7.98 (d, 1H); 8.2 (s, 1H); 8.25 (s, 1H); 8.35 (br s, 1H); 10.9 (s, 1H); MS–ESI: 365 [MH]⁺;

| Elemental analysis: | Found | C 57.2 | H 5.3 | N 13.2 |
|---|---|---|---|---|
| $C_{20}H_{20}N_4O_3$ 1.5HCl | Requires | C 57.3 | H 5.2 | N 13.4% |

EXAMPLE 31

A solution of 4-chloro-6-methoxy-7-(3-pyrrolidin-1-ylpropoxy)quinoline hydrochloride (325 mg, 0.82 mmol) and 4-chloro-2-fluoro-5-hydroxyaniline (133 mg, 0.82 mmol), (as described in EP 61741 A2), in 2-pentanol (10 ml) and DMF (1 ml) was heated at reflux for 5 hours. The volatiles were removed by evaporation and the residue was purified by column chromatography eluting with acetonitrile/water containing 1% TFA (30/70). Concentrated hydrochloric acid was added to the fractions and the solvents were removed by evaporation. The residue was azeotroped with toluene, and triturated with isopropanol. The solid was collected by filtration, washed with ether and dried under vacuum to give 4-(4-chloro-2-fluoro-5-hydroxyanilino)-6-methoxy-7-(3-pyrrolidin-1-ylpropoxy)quinoline hydrochloride (215 mg, 50%).

¹H NMR Spectrum: (DMSOd₆) 1.85–2.1 (m, 4H); 2.35 (t, 2H); 3.0–3.1 (br s, 2H); 3.35 (br s, 2); 3.6 (br s, 2H); 4.05 (s, 3H); 4.32 (t, 2H); 6.55 (dd, 1H); 7.25 (d, 1H); 7.55 (s, 1H); 7.65 (d, 1); 8.2 (s, 1H); 8.42 (d, 1H); 10.7 (br s, 1H); 10.75–10.85 (br s, 2H); MS–ESI: 446 [MH]⁺;

| Elemental analysis: | Found | C 52.3 | H 5.7 | N 7.7 |
|---|---|---|---|---|
| $C_{23}H_{25}N_3O_3ClF$ 1.3H₂O 1.7HCl | Requires | C 52.0 | H 5.6 | N 7.9% |

The starting material was prepared as follows:

A mixture of 5-((3-hydroxy-4-methoxyanilino) methylene)-2,2-dimethyl-1,3dioxane-4,6-dione (10 g, 34.1 mmol), (prepared as described for the starting material in Example 3), 3-(pyrrolidin-1-yl)propyl chloride (7.55 g, 51.1 mmol), (J. Am. Chem. Soc. 1955, 77, 2272), potassium carbonate (7.06 g, 51.1 mmol) and potassium iodide (600 mg, 3.41 mmol) in DMF (100 ml) was heated at 80° C. for 2 hours. The mixture was poured into water (800 ml) and the precipitate was collected by filtration. The solid was dissolved in methylene chloride and the organic solution was washed with brine, dried (MgSO₄) and the volatiles were removed by evaporation. The residue was dissolved in ether and the insoluble materials were removed by filtration. The volatiles were removed by evaporation and the residue was precipitated by trituration with petroleum ether, collected by filtration and dried under vacuum to give 5-((3-(3-pyrrolidin-1-ylpropoxy)-4-methoxyanilino)methylene)-2,2-dimethyl-1,3-dioxane-4,6-dione (5.1 g, 37%).

¹H NMR Spectrum: (DMSOd₆; CD₃COOD) 1.7 (s, 6H); 1.95 (m, 4H); 2.1–2.2 (m, 2.H); 3.3 (m, 6H); 3.8 (br s, 3H); 4.15 (t, 2H); 7.05 (d, 1H); 7.1 (d, 1H); 7.32 (d, 1H); 8.55 (s, 1H).

After refluxing a solution of 5-((3-(3-pyrrolidin-1-ylpropoxy)-4-methoxyanilino)methylene)-2,2-dimethyl-1,3-dioxane-4,6-dione (4.9 g, 12 mmol) in phenyl ether (50 ml) for 1 minute, the mixture was poured into petroleum ether (500 ml). The solid was collected by filtration and purified by reverse phase chromatography on a Diaion (trade mark of Mitsubishi) HP20SS resin column eluting with water/methanol (100/0 increasing to 20/80). After removal of the solvent by evaporation, the purified product was azeotroped with a mixture of ethanol and toluene to give 6-methoxy-7-(3-pyrrolidin-1-ylpropoxy)-1,4-dihydroquinolin-4-one (1 g, 27%).

¹H NMR Spectrum: (DMSOd₆) 1.7 (s, 4H); 1.95 (m, 2H); 2.45 (br s, 4H); 2.55 (t, 2H); 3.8 (s, 3H); 4.10 (t, 2H); 5.95 (d, 1H); 7.0 (s, 1H); 7.45 (s, 1H); 7.80 (d, 1H); 11.55 (br s, 1H).

A solution of 6-methoxy-7-(3-pyrrolidin-1-ylpropoxy)-1, 4-dihydroquinolin-4-one (950 mg, 3.1 mmol) in thionyl chloride (25 ml) containing DMF (10 drops) was heated at reflux for 1.5 hours. After cooling, toluene was added and the volatiles were removed by evaporation. The residue was triturated with ether, collected by filtration, washed with ether and dried under vacuum to give 4-chloro-6-methoxy-7-(3-pyrrolidin-1-ylpropoxy)quinoline hydrochloride (1.23 g, 100%).

$^1$H NMR Spectrum: (DMSOd$_6$) 1.9–2.0 (m, 2H); 2.0–2.1 (m, 2H); 2.3–2.4 (m, 2H); 3.0–3.1 (m, 2H); 3.3–3.4 (m, 2H); 3.5–3.6 (m, 2H); 4.05 (s, 3H); 4.35 (t, 2H); 7.55 (s, 1H); 7.8 (s, 1H); 8.0 (d, 1H); 8.92 (d, 1H); 11.1 (br s, 1H).

EXAMPLE 32

A solution of 4-chloro-6-methoxy-7-(2-methoxyethoxy)quinoline hydrochloride (3 g, 9.8 mmol), (prepared as described for the starting material in Example 5), and 4-chloro-2-fluoroaniline (2.2 ml, 19.6 mmol) in DMF (50 ml) was heated at 150° C. for 30 minutes. After dilution with isopropanol (50 ml), the precipitate was collected by filtration and dried under vacuum to give 4-(4-chloro-2-fluoroanilino)-6-methoxy-7-(2-methoxyethoxy)quinoline hydrochloride (2.05 g, 50%).

$^1$H NMR Spectrum: (DMSOd$_6$) 3.37 (s, 3H); 3.8 (t, 2H); 4.03 (s, 3H); 4.35 (t, 2H); 6.5 (d, 1H); 7.52 (s, 1H); 7.54 (d, 1H); 7.68 (t, 1H); 7.8 (d, 1H); 8.2 (s, 1H); 8.42 (d, 1H); 10.72 (br s, 1H); MS–ESI: 337 [MH]$^+$;

| Elemental analysis: | Found | C 55.0 | H 4.9 | N 6.7 |
|---|---|---|---|---|
| C$_{19}$H$_{18}$N$_2$O$_3$ClF 0.34H$_2$O 0.95HCl 0.08isopropanol 0.04DMF | Requires | C 54.7 | H 4.9 | N 6.6% |

EXAMPLE 33

Using an analogous procedure to that described for Example 31, 4-chloro-6-methoxy-7-(3-morpholinopropoxy)quinoline hydrochloride (300 mg, 0.73 mmol), (prepared as described for the starting material in Example 7), was reacted with 4-chloro-2-fluoroaniline (160 µl, 1.4 mmol) to give 4-(4-chloro-2-fluoroanilino)-6-methoxy-7-(3-morpholinopropoxy)quinoline hydrochloride (88 mg, 23%).

$^1$H NMR Spectrum: (DMSOd$_6$) 2.35 (t, 2H); 3.05–3.2 (br s, 2H); 3.2–3.6 (m, 4H); 3.95 (br s, 4H); 4.05 (s, 3H); 4.35 (t, 2H); 6.5 (d, 1H); 7.52 (d, 1H); 7.55 (s, 1H); 7.65 (t, 1H); 7.8 (dd, 1H); 8.25 (s, 1H); 8.42 (d, 1H); 10.8 (br s, 1H); MS–ESI: 446 [MH]$^+$;

| Elemental analysis: | Found | C 51.9 | H 5.6 | N 7.6 |
|---|---|---|---|---|
| C$_{23}$H$_{25}$N$_3$O$_3$ClF 1.3H$_2$O 1.8HCl | Requires | C 51.6 | H 5.5 | N 7.8% |

EXAMPLE 34

Using an analogous procedure to that described for Example 15, 4,7-dichloroquinoline (198 mg, 1 mmol) was reacted with 4-chloro-2-fluoro-5-hydroxyaniline (194 mg, 1.2 mmol), (as described in EP 61741 A2), in 2-pentanol (5 ml) to give 7-chloro-4-(4-chloro-2-fluoro-5-hydroxyanilino)quinoline (258 mg, 72%).

$^1$H NMR Spectrum: (DMSOd$_6$) 6.65 (dd, 1H); 7.15 (d, 1H); 7.68 (d, 1H); 7.95 (dd, 1H); 8.15 (d, 1H); 8.6 (d, 1H); 8.8 (d, 1H); MS–EI: 322 [MH]$^+$.

EXAMPLE 35

Using an analogous procedure to that described for Example 15, 4,7-dichloroquinoline (198 mg, 1 mmol) was reacted with 4-bromo-2-fluoro-5-hydroxyaniline (248 mg, 1.2 mmol), (as described in EP 61741 A2), in 2-pentanol (5 ml) to give 4-(4-bromo-2-fluoro-5-hydroxyanilino)-7-chloroquinoline hydrochloride (327 mg, 81%).

$^1$H NMR Spectrum: (DMSOd$_6$) 6.65 (dd, 1H); 7.15 (d, 1H); 7.8 (d, 1H); 7.95 (d, 1H); 8.15 (s, 1H); 8.62 (d, 1H); 8.8 (d, 1H); 10.85 (s, 1H); 11.0 (br s, 1H); MS–EI: 367 [M.]$^+$;

| Elemental analysis: | Found | C 44.4 | H 2.6 | N 6.8 |
|---|---|---|---|---|
| C$_{15}$H$_9$N$_2$OBrClF 1HCl | Requires | C 44.6 | H 2.5 | N 6.9% |

EXAMPLE 36

Using an analogous procedure to that described for Example 15, 4-chloro-6-methoxy-7-(3-pyrrolidin-1-ylpropoxy)quinoline hydrochloride (197 mg, 0.5 mmol), (prepared as described for the starting material in Example 31), was reacted with 2-fluoro-5-hydroxy-4-methylaniline (85 mg, 0.6 mmol), (prepared as described for the starting material in Example 1), in 2-pentanol (5 ml) to give 4-(2-fluoro-5-hydroxy-4-methylanilino)-6-methoxy-7-(4-pyrrolidin-1-ylpropoxy)quinoline hydrochloride (202 mg, 83%).

$^1$H NMR Spectrum: (DMSOd$_6$; CF$_3$COOD) 1.85–1.95 (m, 2H); 2.0–2.1 (m, 2H); 2.2 (s, 3H); 2.2–2.3 (m, 2H); 3.0–3.1 (m, 2H); 3.3–3.4 (m, 2H); 3.6–3.7 (m, 2H); 4.0 (s, 3H); 4.3 (t, 2); 6.5 (dd, 1H); 6.9 (d, 1H); 7.22 (d, 1H); 7.45 (s, 1H); 8.05 (s, 1H); 8.4 (d, 1H); MS–ESI: 426 [MH]$^+$;

| Elemental analysis: | Found | C 57.5 | H 6.7 | N 7.9 |
|---|---|---|---|---|
| C$_{24}$H$_{28}$N$_3$O$_{3F\ 0.45H2}$O 1.95HCl 0.44 2-pentanol | Requires | C 57.9 | H 6.7 | N 7.7% |

EXAMPLE 37

Using an analogous procedure to that described for Example 15, 4-chloro-6-methoxy-7-(3-pyrrolidin-1-ylpropoxy)quinoline hydrochloride (236 mg, 0.6 mmol), (prepared as described for the starting material in Example 31), was reacted with 4-chloro-2-fluoroaniline (80 µl, 0.72 mmol) in 2-pentanol (5 ml) to give 4-(4-chloro-2-fluoroanilino)-6-methoxy-7-(3-pyrrolidin-1-ylpropoxy)quinoline hydrochloride (124 mg, 42%).

$^1$H NMR Spectrum: (DMSOd$_6$; CF$_3$COOD) 1.9–2.0 (m, 2H); 2.0–2.1 (m, 2H); 2.25–2.35 (m, 2H); 3.0–3.15 (m, 2H); 3.35 (t, 2H); 3.6–3.7 (m, 2H); 4.05 (s, 3H); 4.32 (t, 2H); 6.55 (dd, 1); 7.48 (s, 1H); 7.52 (d, 1H); 7.65 (t, 1H); 7.78 (d, 1H); 8.1 (s, 1H); 8.45 (d, 1H); MS–ESI: 430 [MH]$^+$;

| Elemental analysis: | Found | C 52.6 | H 5.6 | N 8.0 |
|---|---|---|---|---|
| C$_{23}$H$_{25}$N$_3$O$_2$ClF 1.3H$_2$O 1.9HCl | Requires | C 52.9 | H 5.7 | N 8.0% |

EXAMPLE 38

A mixture of 4-chloro-6-methoxy-7-(2-([1,2,4]-triazol-1-yl)ethoxy)quinoline (132 mg, 0.43 mmol), 4-chloro-2-fluorophenol (400 mg, 2.7 mmol) and potassium hydroxide (28 mg, 0.49 mmol) was head at 165° C. for 3 hours under argon. The mixture was partitioned between ethyl acetate and water. The organic layer was washed with water, brine, dried (MgSO$_4$) and the volatiles were removed by evaporation. The residue was purified by column chromatography eluting with methylene chloride/methanol (95/5). The purified product was dissolved in methylene chloride and 2M ethereal hydrogen chloride (0.5 ml) was added. The volatiles were removed by evaporation and the residue was triturated with ether, collected by filtration and dried under vacuum to give 4-(4-chloro-2-fluorophenoxy)-6-methoxy-7-(2-([1,2,4]-triazol-1-yl)ethoxy)quinoline hydrochloride (110 mg, 61%).

$^1$H NMR Spectrum: (DMSOd$_6$; CF$_3$COOD) 4.02 (s, 3H); 4.65 (t, 2H); 4.85 (t, 2H); 7.15 (d, 1H); 7.55 (d, 1H); 7.68 (d, 1H); 7.7 (s, 1H); 7.78 (s, 1H); 7.88 (dd, 1H); 8.25 (s, 1H); 8.88 (s, 1H); 8.90 (d, 1H); MS–ESI: 415 [MH]$^{30}$;

| Elemental analysis: | Found | C 48.8 | H 4.0 | N 11.1 |
|---|---|---|---|---|
| C$_{20}$H$_{16}$N$_4$O$_3$ClF 0.8H$_2$O 1.65HCl | Requires | C 49.1 | H 3.9 | N 11.4% |

The starting material was prepared as follows:

Diethyl azodicarboxylate (1 ml, 6.5 mmol) was added dropwise to a solution of 4-chloro-7-hydroxy-6-methoxyquinoline (845 mg, 4.0 mmol), (prepared as described for the starting material in Example 3), 2-([1,2,4]-triazol-1-yl)ethanol (500 mg, 4.4 mmol), (Ann. Pharm. Fr. 1977, 35, 503–508), and triphenylphosphine (1.7 g, 6.5 mmol) in methylene chloride (40 ml) under argon. After stirring for 4 days at ambient temperature, the insoluble materials were removed by filtration. The volatiles were removed by evaporation and the residue was purified by column chromatography on silica eluting with methylene chloride/acetonitrile/methanol (75/20/5). The product was purified by a second chromatography on neutral alumina eluting with methylene chloride/acetonitrile/methanol (75/20/5). The purified product was triturated with ether, collected by filtration and dried under vacuum to give 4-chloro-6-methoxy-7-(2-([1,2,4]-triazol-1-yl)ethoxy)quinoline (544 mg, 45%).

$^1$H NMR Spectrum: (DMSOd$_6$) 3.94 (s, 3H); 4.58 (t, 2H); 4.68 (t, 2H); 7.38 (s, 1H); 7.5 (s, 1H) 7.58 (d, 1H); 8.0 (s, 1H); 8.58 (s, 1H); 8.62 (d, 1H).

EXAMPLE 39

A solution 2 4-chloro-6-methoxy-7-(2-([1,2,4]-triazol-1-yl)ethoxy)quinoline (203 mg, 0.66 mmol), (prepared as described for the starting material in Example 38), and 4-chloro-2-fluoroaniline (74 µl, 0.66 mmol) in DMF (10 ml) containing 5M hydrogen chloride in isopropanol (0.4 ml) was heated at 150° C. for 8 hours. The volatiles were removed by evaporation and the residue was partitioned between water and methylene chloride. The aqueous layer was adjusted to pH9 with I M sodium hydroxide. The organic layer was washed with brine, dried (MgSO$_4$) and the volatiles were removed by evaporation. The residue was dissolved in methylene chloride/methanol and 2M ethereal hydrogen chloride (1 ml) was added. After removal of the volatiles by evaporation, the residue was triturated with ether, collected by filtration, washed with ether and dried under vacuum to give 4-(4-chloro-2-fluoroanilino)-6-methoxy-7-(2-([1,2,4]-triazol-1-yl)ethoxy)quinoline hydrochloride (60 mg, 17%).

$^1$H NMR Spectrum: (DMSOd$_6$; CF$_3$COOD) 4.0 (s, 3H); 4.6 (t, 2H); 4.8 (t, 2H); 6.55 (dd, 1H); 7.45 (s, 1H); 7.52 (d, 1H); 7.65 (t, 1H); 7.78 (dd, 1H); 8.0 (s, 1H); 8.2 (s, 1H); 8.45 (d, 1H); 8.82 (s, 1H); MS–ESI: 414 [MH]$^+$;

| Elemental analysis: | Found | C 49.8 | H 4.2 | N 14.6 |
|---|---|---|---|---|
| C$_{20}$H$_{17}$N$_5$O$_2$ClF 0.3H$_2$O 1.75HCl | Requires | C 49.7 | H 4.0 | N 14.5% |

EXAMPLE 40

A solution of 4-chloro-6-methoxy-7-(2-methoxyethoxy)quinoline hydrochloride (304 mg, 1 mmol), (prepared as described for the starting material in Example 5), 2-fluoro-5-hydroxy-4-methylaniline (155 mg, 1.1 mmol), (prepared as described for the starting material in Example 1), in 2-pentanol (15 ml) was heated at reflux for 15 hours. The precipitate was collected by filtration, washed with isopropanol and dried under vacuum to give 4-(2-fluoro-5-hydroxy-4-methylanilino)-6-methoxy-7-(2-methoxyethoxy)quinoline hydrochloride (205 mg, 50%).

$^1$H NMR Spectrum: (DMSOd$_6$) 2.2 (s, 3H); 3.34 (s, 3H); 3.8 (t, 2H); 4.02 (s, 3H); 4.32 (t, 2H); 6.45 (d, 1H); 6.95 (d, 1H); 7.23 (d, 1H); 7.5 (s, 1H); 8.12 (s, 1H); 8.4 (d, 1H); 9.9 (s, 1H); 10.5 (s, 1H); MS–ESI: 373[MH]$^+$;

| Elemental analysis: | Found | C 57.9 | R 5.7 | N 6.6 |
|---|---|---|---|---|
| C$_{20}$H$_{21}$N$_2$O$_4$F 0.5H$_2$O 0.9HCl | Requires | C 58.0 | H 5.6 | N 6.8% |

EXAMPLE 41

A mixture of 7-benzyloxy-4-chloro-6-methoxyquinoline hydrochloride (300 mg, 0.89 mmol), (prepared as described for the starting material in Example 3), and 4-chloro-2-fluoroaniline (160 mg, 1.1 mmol) was heated at reflux in cyclohexane (20 ml) for 24 hours. The solvent was removed by evaporation and the residue was triturated with ether. The solid crude product was collected by filtration and purified by column chromatography eluting with methylene chloride/methanol (100/0 increasing to 95/5) to give 7-benzyloxy-4-(4-chloro-2-fluoroanilino)-6-methoxyquinoline hydrochloride (83 mg, 21%).

m.p. 222–225° C.; $^1$H NMR Spectrum: (DMSOd$_6$) 3.92 (s, 3H); 5.22 (s, 2H); 6.35 (m, 1H); 7.52–7.32 (m, 8H); 7.59 (dd, 1H); 7.68 (s, 1H); 8.24 (d, 1H); 8.64 (s, 1H); MS–ESI: 409 [MH]$^+$.

EXAMPLE 42

A mixture of 4-(4-chloro-2-fluoroanilino)-7-hydroxy-6-methoxyquinoline (500 mg, 1.7 mmol), potassium carbonate (232 mg, 1.7 mmol) and 2-bromoethanol (1181l, 1.7 mmol) in DMF (15 ml) was heated at 80° C. for 5 hours. The mixture was allowed to cool, was diluted with water and extracted with ethyl acetate. The combined extracts were washed with water, dried (MgSO$_4$) and the solvent removed by evaporation. The residue was purified by column chromatography eluting with methylene chloride/methanol (100/0 increasing to 95/5) to give 4-(4-chloro-2-fluoroanilino)-7-(2-hydroxyethoxy)-6-methoxyquinoline (160 mg, 26%).

$^1$H NMR Spectrum: (DMSOd$_6$) 3.80 (t, 2H); 3.94 (s, 3H); 4.12 (t, 2H); 4.90 (s, 1H); 6.34 (dd, 1H); 7.24 (s, 1H); 7.38 (dd, 1H); 7.43 (s, 1H); 7.60 (dd, 1H); 7.68 (s, 1H); 8.24 (d, 1H); MS—ESI: 363 [MH]$^+$;

| Elemental analysis: | Found | C 57.9 | H 4.3 | N 7.5 |
| --- | --- | --- | --- | --- |
| $C_{18}H_{16}N_2O_3ClF$ 0.6$H_2O$ | Requires | C 57.9 | R 4.6 | N 7.5% |

The starting material was prepared as follows:

A mixture of 7-benzyloxy-4-(4-chloro-2-fluoroanilino)-6-methoxyquinoline hydrochloride (4.7 g, 11 mmol), (prepared as described in Example 41), in TFA (100 ml) was heated at reflux for 4 hours. The volatiles were removed by evaporation. Saturated aqueous sodium hydrogen carbonate solution was added to the residue and the mixture was extracted with ethyl acetate. The combined extracts were dried (MgSO$_4$), and the solvent was removed by evaporation. The residue was dissolved in methanol, aqueous ammonia was added and the mixture was stirred for 1 hour. The volatiles were removed by evaporation and the residue was diluted with water. The precipitated product was collected by filtration, washed with water and dried to give 4-(4-chloro-2-fluoroanilino)-7-hydroxy-6-methoxyquinoline (3 g, 76%).

$^1$H NMR Spectrum: (DMSOd$_6$) 3.94 (s, 3H); 6.28 (dd, 1H); 7.18 (s, 1H); 7.35–7.50 (m, 2H); 7.60 (d, 1H); 7.64 (s, 1H); 8.22 (d, 1H); MS–ESI: 319 [MH]$^+$.

EXAMPLE 43

A mixture of 4-(4-chloro-2-fluoroanilino)-7-hydroxy-6-methoxyquinoline (1.2 g, 4 mmol), (prepared as described for the starting material in Example 42), potassium carbonate (556 mg, 4 mmol) and 1,3-dibromopropane (408 μl, 4 mmol) in DMF (30 ml) was heated at 80° C. for 2 hours. The mixture was allowed to cool, was diluted with water and extracted with ethyl acetate. The combined extracts were washed with water, dried (MgSO$_4$) and the solvent removed by evaporation. The residue was purified by column chromatography eluting with methylene chloride/methanol (100/0 increasing to 70/30) to give 4-(4-chloro-2-fluoronilino)-7-(3-hydroxypropoxy)-6-methoxyquinoline (36 mg, 3%).

m.p. 1716–1780° C.; $^1$H NMR Spectrum: (DMSOd$_6$) 1.95 (t, 2H); 3.58 (q, 2H); 3.92 (s, 3H); 4.18 (t, 2H); 4.58 (t, 1H); 6.54 (dd, 1H); 7.25 (s, 1H); 7.38 (dd, 1H); 7.42 (t, 1H); 7.60 (dd, 1H); 7.70 (s 1H); 8.24 (d, 1H); MS–ESI: 376 [MH]$^+$.

EXAMPLE 44

1,1'-(Azodicarbonyl)dipiperidine (963 mg, 4 mmol) was added in portions to a mixture of 4-(4-chloro-2-fluoroanilino)-7-hydroxy-6-methoxyquinoline (400 mg, 1.2 mmol), (prepared as described for the starting material in Example 42), tributylphosphine (921 μl, 44 mmol) and 2-(dimethylamino)ethanol (251 μl, 2.5 mmol) in methylene choride (30 ml) at 10° C. under argon. The mixture was stirred for 18 hours at ambient temperature, was diluted with ether and the insoluble materials were removed by filtration. The solvent was removed by evaporation and the residue was purified by column chromatography eluting with methylene chloride/methanol/triethylamine (100/0/0 increasing to 70/30/0.5). The purified product was dissolved in methanol and 1M ethereal hydrogen chloride (8 ml) was added. The volatiles were removed by evaporation and the residue was triturated with methylene chloride, collected by filtration washed with ether and dried to give 4-(4-chloro-2-fluoroanilino)-7-(2-(dimethylamino)ethoxy)-6-methoxyquinoline hydrochloride (145 mg, 30%).

m.p. >250° C.; $^1$H NMR Spectrum: (DMSOd$_6$) 2.90 (s, 6H); 3.60 (t, 2H); 4.05 (s, 3H); 4.60 (t, 2H); 6.50 (dd, 1H); 7. 5 (dd, 1H); 7.62 (t, 2H); 7.78 (dd, 1H); 8.32 (s, 1H); 8.40 (s, 1H); MS–ESI: 390 [MH]$^+$;

| Elemental analysis: | Found | C 45.0 | H 5.6 | N 7.6 |
| --- | --- | --- | --- | --- |
| $C_{20}H_{21}N_3O_2ClF$ 4$H_2O$ 2HCl | Requires | C 45.0 | H 5.8 | N 7.9% |

EXAMPLE 45

1,1'-(Azodicarbonyl)dipiperidine (963 mg, 4 mmol) was added in portions to a mixture of 4-(4-chloro-2-fluoroanilino)-7-hydroxy-6-methoxyquinoline (400 mg, 1.2 mmol), (prepared as described for the starting material in Example 42), tributylphosphine (921 μl, 4 mmol) and 3-(dimethylamino)-1-propanol (179 μl, 1.5 mmol) in methylene choride (50 ml) at 10° C. under argon. The mixture was stirred for 18 hours at ambient temperature, was diluted with ether and the insoluble materials were removed by filtration. The solvent was removed by evaporation and the residue was dissolved in ethyl acetate, washed with water and brine and dried (MgSO$_4$). The volatiles were removed by evaporation. The residue was purified by column chromatography eluting with methylene chloride/methanol/triethylamine (97/3/0 increasing to 75/25/0.5). The purified product was dissolved in methanol and 1M ethereal hydrogen chloride (8 ml) was added. The volatiles were removed by evaporation and the residue was triturated with methylene chloride, collected by filtration washed with ether and dried to give 4-(4-chloro-2-fluoroanilino)-7-(3-(dimethylamino)propoxy)-6-methoxyquinoline (94 mg, 20%).

$^1$H NMR Spectrum: (DMSOd$_6$) 2.24 (t, 2H); 2.78 (s, 6H); 3.38 (m, 2H); 3.98 (s, 3H); 4.21 (t, 2H); 6.38 (dd, 1H); 6.98 (s, 1H); 7.00 (dd, 1H); 7.52 (t, 1H); 7.62 (dd, 1H); 7.94 (s, 1H); 8.30 (d, 1H); MS–ESI: 404 [MH]$^+$.

EXAMPLE 46

A mixture of 4-chloro-6,7-dimethoxyquinoline hydrochloride (540 mg, 2.08 mmol), (prepared as described for the starting material in Example 2), in 3-aminophenol (1 ml) and isopropanol (15 ml) was heated at reflux for 2 hours. The mixture was allowed to cool and the solid product was collected by filtration, washed with acetone and dried to give 6,7-dimethoxy-4-(3-hydroxyanilino)quinoline hydrochloride (336 mg, 47%).

m.p. 280–283° C.; $^1$H NMR Spectrum: (DMSOd$_6$) 3.97 (s, 3H); 4.03 (s, 3H); 6.74–6.78 (d, 1H); 6.80–6.90 (m, 3H); 7.30–7.40 (t, 1H); 7.48 (s, 1H); 8.15 (s, 1H); 8.30–8.35 (d, 1H); 10.62 (s, 1H); 14.30 (br s, 1H); MS–ESI: 297 [MH]$^+$;

| Elemental analysis: | Found | C 59.6 | H 5.1 | N 8.4 |
| --- | --- | --- | --- | --- |
| $C_{17}H_{16}N_2O_3$ 1.5$H_2O$ 1HCl | Requires | C 59.7 | H 5.3 | N 8.2% |

EXAMPLE 47

A mixture of 4-chloro-6,7-dimethoxyquinoline hydrochloride (360 mg, 1.4 mmol), (prepared as described for the starting material in Example 2), and 2-fluoro-5-hydroxy-4-methylaniline (212 mg 1.5 mmol), (prepared as described for the starting material in Example 1), in isopropanol (15 ml) was heated at reflux for 3 hours. The mixture was allowed to cool and the solid product was collected by filtration, washed with acetone and dried to give 6,7- dimethoxy-4-(2-fluoro-5-hydroxy-4-methylanilino) quinoline hydrochloride (146 mg, 29%).

m.p. >280° C.; $^1$H NMR Spectrum: (DMSOd$_6$) 2.15 (s, 3H); 3.98 (s, 3H); 4.0 (s, 3H); 6.40–6.45 (dd, 1H); 6.87–6.90 (d, 1H); 7.13–7.17 (d, 1H); 7.47 (s, 1H); 8.11 (s, 1H); 8.55–8.62 (d, 1H); 9.75 (br s, 1H); 10.42 (s, 1H); 14.32 (br s, 1H); MS–ESI: 329 [MH]$^+$;

| Elemental analysis: | Found | C 58.7 | H 5.1 | N 7.3 |
|---|---|---|---|---|
| C$_{18}$H$_{17}$N$_2$O$_3$F 1HCl | Requires | C 59.3 | H 5.0 | N 7.7% |

EXAMPLE 48

A mixture of 4-chloro-6-cyano-7-(2-methoxyethoxy) quinoline hydrochloride (220 mg 0.84 mmol), (prepared as described for the starting material in Example 1), and 3-hydroxy-4-methylaniline (123 mg, 1 mmol) in isopropanol (10 ml) was heated at reflux for 1 hour. The mixture was allowed to cool, the solid product was collected by filtration, washed with acetone and dried to give 6-cyano-4-(3-hydroxy-4-methylanilino)-7-(2-methoxyethoxy) quinoline hydrochloride (210 mg, 60%) as an orange solid.

m.p. 275–278° C.; $^1$H NMR Spectrum: (DMSOd$_6$) 2.28 (s, 3H); 3.18 (s, 3H); 3.64–3.68 (t, 2H); 4.18–4.46 (t, 2H); 6.70–6.80 (dt, 2H); 6.88 (d, 1H); 7.22–7.27 (d, 1H); 7.60 (s, 1H); 8.40–8.45 (d, 1); 9.30 (s, 1H); 9.90 (s, 1H); 11.02 (s, 1H); MS–ESI: 350 [MH]$^{30}$ ;

| Elemental analysis: | Found | C 62.0 | H 4.9 | N 10.6 |
|---|---|---|---|---|
| C$_{20}$H$_{19}$N$_3$O$_3$ 1HCl | Requires | C 62.2 | H 5.2 | N 10.9% |

EXAMPLE 49

A mixture of 4-chloro-6-cyano-7-methoxyquinoline hydrochloride (500 mg, 2 mmol), (prepared by an analogous procedure to that described for the starting material in Example 1 but using methanol instead of 2-methoxyethanol), and 2-fluoro-5-hydroxy-4-methylaniline (141 mg, 1 mmol), (prepared as described for the starting material in Example 1), in isopropanol (10 ml) was heated at reflux for 4 hours. The mixture was allowed to cool, the solid product was collected by filtration, washed with acetone and dried to give 6-cyano-4-(2-fluoro-5-hydroxy-4-methylanilino)-7-methoxyquinoline hydrochloride (176 mg, 54%) as a light brown solid.

m.p. 278–281° C.; $^1$H NMR Spectrum: (DMSOd$_6$) 2.16 (s, 3H); 4.08 (s, 3H); 6.45–6.50 (dd, 1H), 6.88–6.90 (d, 1H); 7.15–7.120 (d, 1H); 7.60 (s, 1H); 8.48 (d, 1H); 9.35 (s, 1H); 9.88 (br s, 1H); 11.07 (br s, 1H); MS–ESI: 324 [MH]$^{30}$;

| Elemental analysis: | Found | C 58.3 | H 4.0 | N 12.0 |
|---|---|---|---|---|
| C$_{18}$H$_{14}$N$_3$O$_2$F 0.5H$_2$O 1HCl | Requires | C 58.6 | H 4.3 | N 11.4% |

EXAMPLE 50

1,3-Dihydroxybenzene (110 mg, 1 mmol) was added to a stirred suspension of sodium hydride (60 mg, 2 mmol) in DMF (10 ml) and the mixture was stirred for 30 minutes. 4-Chloro-6-cyano-7-(2-methoxyethoxy)quinoline hydrochloride (300 mg 1 mmol), (prepared as described for the starting material in Example 1), was added and the mixture was heated at 100° C. for 4 hours. The mixture was allowed to cool, was quenched with water and extracted with ethyl acetate (2×75 ml). The extracts were combined, washed with water (×2) and then brine and dried (MgSO$_4$). The solvent was removed by evaporation and the residue was triturated with ethyl acetate/hexane, collected by filtration and dried to give 6-cyano-4-(3-hydroxyphenoxy)-7-(2-methoxyethoxy) quinoline (115 mg, 34%).

m.p. 159–163° C.; $^1$H NMR Spectrum: (DMSOd$_6$) 3.35 (s, 3H); 3.72–3.80 (t, 2H); 4.38–4.46 (t, 2H); 6.56–6.59 (d, 1H); 6. 62–6.64 (t, 1H); 6.60–6.72 (dd, 1H); 6.74–6.78 (dd, 1H); 7.25–7.32 (t, 1H); 7.60 (s, 1H); 8.70 (s, 1H); 8.70–8.75 (d, 1H); 9.88 (s, 1H); MS–ESI: 337 [MH]$^+$.

| Elemental analysis: | Found | C 67.2 | H 4.9 | N 8.2 |
|---|---|---|---|---|
| C$_{20}$H$_{18}$N$_2$O$_4$ | Requires | C 67.8 | H 4.8 | N 8.3% |

EXAMPLE 51

A mixture of 5-((4-cyano-3-(3-morpholinopropoxy) anilino)methylene)-2,2-dimethyl-1,3-dioxane-4,6-dione (2.96 g, 7 mmol) in DOWTHERM A, (trade mark of Fluka Chemie AG), (100 ml) was heated at 250° C. for 30 minutes. The mixture was allowed to cool, hexane was added and the solvent was decanted from the resulting gum. The residue was triturated with hexane to give crude 6-cyano-7-(3-morpholinopropoxy)-1,4-dihydroquinolin-4-one(1.0 g) as a brown solid. A portion of this product (380 mg, 1.3 mmol) was added to thionyl chloride (10 ml)and DMF (0.1 ml) and the mixture was heated at reflux for 3 hours. The volatiles were removed by evaporation and the residue was azeotroped with toluene (×3). 2-Fluoro-5-hydroxy-4-methylaniline (184 mg, 1.3 mmol), (prepared as described for the starting material in Example 1), in isopropanol (10 ml) was added to the residue, and the mixture was heated at reflux for 3 hours. The mixture was allowed to cool, the solid product was collected by filtration and recrystallised twice from methylene chloride/methanol/ethyl acetate to give 6-cyano-4-(2-fluoro-5-hydroxy-4-methylanilino)-7-(3-morpholinopropoxy)quinoline (05 mg, 3% overall).

m.p. >3130° C.; $^1$H NMR Spectrum: (DMSOd6) 2.16 (s, 3H); 2.75 (br t, 2H); 3.05 (m, 2H); 3.30 (m, 2H); 3.80–4.00 (m, 4H); 4.40 (t, 2H); 6.45 (dd, 1H); 6.92 (d, 1H); 7.20 (d, 1H); 7.65 (s, 1H); 8.50 (d, 1H); 9.40 (s, 1H); 11.16 (br s, 1H); 11.23 (br s, 1H); MS–ESI: 437 [MH]$^+$.

The starting material was prepared as follows:

Sodium hydride (2.0 g of an 85% dispersion in mineral oil, 60 mmol) was added to 4-(3-hydroxypropyl)morpholine (4.8 g, 30 mmol), (Tet. Lett. 1994, 35, 1715), in NMP (50 ml) and the mixture was stirred for 15 minutes. 3-Chloro-4-cyanoaniline (4.8 g, 30 mmol) was added and the mixture was heated at 145° C. for 6 hours. The mixture was allowed to cool and was partitioned between ethyl acetate and water. The organic layer was separated, washed with water and then brine and dried (MgSO$_4$). The solvent was removed by evaporation and the residue was purified by column chromatography eluting with ethyl acetate and then methylene chloride/methanol (9/1) to give 4-cyano-3-(3-morpholinopropoxy)aniline (2.0 g, 26%) as a yellow gum.

$^1$H NMR Spectrum: (DMSOd$_6$) 1.80–1.95 (t, 2H); 2.30–2.45 (m, 6H); 3.55 (t, 4H); 4.00 (t, 2H); 6.10 (s, 2H); 6.15 (d,l H); 6.22 (s, 1H); 7.20 (d, 1H);

4-Cyano-3-(3-morpholinopropoxy)aniline (2.5 g, 9.6 mmol) and 2,2-dimethyl-5-methoxymethylene-1,3-dioxane- 4,6-dione (2.4 g, 13 mmol), (Montatsh. Chem. 1967, 98, 564), in ethanol (40 ml) was heated at reflux for 2 hours. The mixture was allowed to cool and the solid was collected by filtration to give 5-((4-cyano-3-(3-morpholinopropoxy) anilino)methylene)-2,2-dimethyl-1,3-dioxane-4.6-dione (2.96 g, 74%).

$^1$H NMR Spectrum: (DMSOd$_6$) 1.70 (s, 6H); 2.00 (br m, 2H; 2.50 (br m, 6H); 2.65 (br m, 4H), 4.25 (t, 2H); 7.25–7.30 (dd, 1H); 7.55 (d, 1H); 7.75–7.80 (d, 1H); 8.70–8.75 (d, 1H); MS—SI: 416 [MH]$^+$.

EXAMPLE 52

A mixture of 4-chloro-6-cyano-7-(2-methoxyethoxy) quinoline hydrochloride (300 mg 1 mmol), (prepared as described for the starting material in Example 1), and 4-chloro-2-fluoroaniline (0.5 ml, 3.4 mmol) in isopropanol (20 ml) was heated at reflux for 3 hours. The mixture was allowed to cool, the solid product was collected by filtration, washed with acetone and dried to give 4-(4-chloro-2-fluoroanilino)-6-cyano-7-(2-methoxyethoxy)quinoline hydrochloride (400 mg, 98%).

m.p. 247–250° C.; $^1$H NMR Spectrum: (DMSOd$_6$) 3.35 (s, 3H); 3.80 (t, 2H); 4.42 (t, 2H); 6.85 (dd, 1H); 7.50 (dd, 1H); 7.60 (t, 1H); 7.65 (s, 1H) 7.78 (dd, 1H); 9.52 (d, 1H); 9.40 (s, 1H); MS–ESI: 372 [MH]$^+$;

| Elemental analysis: | Found | C 55.1 | H 3.8 | N 10.1 |
|---|---|---|---|---|
| C$_{19}$H$_{15}$N$_3$O$_2$ClF 0.3H$_2$O 1HCl | Requires | C 55.2 | H 4.0 | N 10.2% |

EXAMPLE 53

A mixture of 2-acetamido-5-chloro-1,8-naphthyridine (357 mg, 1.6 mmol) and 2-fluoro-5-hydroxy-4-methylaniline (200 mg, 1.4 mmol), (prepared as described for the starting material in Example 1), in isopropanol (20 ml) was heated at reflux for 5 hours. The mixture was allowed to cool and the precipitate was collected by filtration, washed with acetone and dried to give 2-acetamido-5-(2-fluoro-5-hydroxy-4-methylanilino)-1,8-naphthyridine hydrochloride (280 mg, 61%).

$^1$H NMR Spectrum: (DMSOd$_6$) 2.16 (s, 3H); 2.46 (s, 3H); 6.41–6.46 (dd, 1H); 6.88–6.92 (d, 1H); 7.17–7.82 (d, 1H); 8.34–8.39 (d, 1H); 8.39–8.44 (d, 1H); 9.16–9.22 (d, 1H); 9.92 (br s, 1H); 11.07 (br s, 1H), 11.20 (br s 1H); MS–ESI: 327 [MH]$^{30}$ ;

| Elemental analysis: | Found | C 54.4 | H 4.6 | N 14.1 |
|---|---|---|---|---|
| C$_{17}$H$_{15}$N$_4$O$_2$F 0.5H$_2$O 1HCl | Requires | C 54.9 | | H 4.5 N 15.1% |

The starting material was prepared as follows:

A mixture of 2-acetamido-6-aminopyridine (2.9 g, 19 mmol), (Angew. chem. 1995, 107, 2589), and 2,2-dimethyl-5-methoxymethylene-1,3-dioxane-4,6-dione (4.28 g, 23 mmol), (Montatsh. Chem. 1967, 98, 564), in ethanol (75 ml) was stirred and heated at reflux for 5 hours. The mixture was allowed to cool and the precipitated product was collected by filtration and dried to give 5-((6-acetamido-2-pyridylamino)methylene)-2,2-dimethyl-1,3-dioxane-4,6-dione (1.3 g, 22%) as a yellow solid.

$^1$H NMR Spectrum: (DMSOd$_6$) 1.62 (s, 6H); 2.08 (s, 3H); 7.25–7.30 (d, 1H); 7.78–7.82 (t, 1H); 7.90–7J95 (d, 1H); 9.13–9.20 (d, 1H); 10.61 (br s, 1H); 11.29 (br d, 1H);

5-((6-Acetamido-2-pyridylamino)methylene)-2,2-dimethyl-1,3-dioxane-4,6-dione (1.3 g, 4.3 mmol) was added in portions to a stirred mixture of biphenyl (13.3 ml) and phenyl ether (36.8 ml) heated at 250° C. and the resulting mixture was stirred for 1 hour at 250° C. The mixture was allowed to cool and was diluted with hexane. The precipitate was collected by filtration and dried to give 2-acetamido-5-hydroxy-1,8-naphthyridine (720 mg, 83%).

$^1$H NMR Spectrum: (DMSOd$_6$) 2.15 (s, 3H); 6.00 (d, 1H); 7.00 (t, 1H); 8.05 (d, 1H); 8.36 (d, 1H); 10.66 (br s, 1H); 11.75 (br d, 1H); MS–ESI: 204 [MH]$^{30}$ .

Phosphorous oxychloride (6.0 ml) was added to a stirred mixture of 2-acetamido-5-hydroxy-1,8-naphthyridine (2.4 g, 11.8 mmol) and N,N-dimethylaniline (6.0 ml) in toluene (100 ml). The mixture was then heated at reflux for 1 hour. The mixture was allowed to cool, the toluene was removed by evaporation and the residue was partitioned between methylene chloride and aqueous sodium hydrogen carbonate solution. The organic layer was separated, dried (MgSO$_4$) and the solvent was removed by evaporation to give 2-acetamido-5-chloro-1,8-naphthyridine (470 mg, 18%) as a brown solid.

$^1$H NMR Spectrum: (DMSOd$_6$) 2.15 (s, 3H); 7.69–7.72 (d, 1H); 8.48–8.5 1(d, 1H); 8.58–8.62 (d, 1H), 8.90–8.93 (d, 1H); 11.25 (br s, 1H); MS–ESI: 222 [MH]$^+$.

EXAMPLE 54

A mixture of 2-acetamido-5-(2-fluoro-5-hydroxy-4-methylanilino)-1,8-naphthyridine hydrochloride (170 mg, 0.46 mmol), (prepared as described in Example 53), and concentrated hydrochloric acid (0.5 ml) in ethanol (10 ml) was heated at reflux for 2 hours. The mixture was allowed to cool and the organic volatiles were removed by evaporation. The aqueous residue was basified to pH9 with aqueous sodium hydroxide solution and the resulting precipitate was collected by filtration, washed with water and dried to give 2-amino-5-(2-fluoro-5-hydroxy-4-methylanilino)-1,8-naphthyridine (100 mgs 76%).

$^1$H NMR Spectrum: (DMSOd6) 2.15 (s, 3H); 6.15–6.20 (dd, 1H); 6.80–6.86 (m, 2H); 7.08–7.15 (d, 1H); 7.50 (s, 2H); 8.08–8.12 (d, 1H); 8.54–9.02 (d, 1H); 9.75 (br s, 1H); MS–ESI: 285 [MH]$^+$.

EXAMPLE 55

4-Chloro-7-methoxy-6-methoxycarbonylquinoline (1.4 g, 5.5 mmol) was dissolved in cyclohexanol (30 ml) and 4-chloro-2-fluoroaniline (0.786 g, 5.8 mmol) was added. The mixture was heated at 130° C. for 1 hour then at 160° C. for 3hours. The solvent was removed by evaporation and the residue was purified by flash chromatography eluting with methylene chloride/ethylacetate (100/0 increasing to 50/50). The solvent was removed by evaporation and the solid was triturated with ether/isohexanes. The solid was collected by filtration, washed with ether and dried under vacuum to give 4-(4-chloro-2-fluoroanilino)-7-methoxy-6-methoxycarbonylquinoline (570 mg, 28%).

$^1$H NMR Spectrum: (DMSOd$_6$) 3.85 (s, 3H); 3.95 (s, 3H); 6.30 (m, 1H); 7.35 (br s, 2H); 7.45 (m, 1H); 7.60 (d, 1H); 8.40 (br s, 1H); 8.75 (s, 11H); 9.15 (br s, 1H); MS–ESI: 361 [MH]$^{30}$ ;

| Elemental analysis: | Found | C 59.6 | H 3.8 | N 7.6 |
| --- | --- | --- | --- | --- |
| $C_{18}H_{14}N_2O_3ClF$ | Requires | C 59.9 | H 3.9 | N 7.8% |

The starting material was prepared as follows:

3-Methoxy-4-methoxycarbonylaniline (14.15 g, 78 mmol) was suspended in isopropanol and heated at 50° C. 2,2-Dimethyl-5-methoxymethylene-1,3-dioxane-4,6-dione (14.8 g, 80 mmol), (Montatsh. Chem. 1967, 98, 564), was then added in portions over 10 minutes and the mixture was heated at reflux for 30 minutes. The mixture was left to cool to ambient temperature overnight. The precipitate formed was collected by filtration, washed with isopropanol and dried under vacuum to give 5-((3-methoxy-4-methoxycarbonylanilino)methylene)-2,2-dimethyl-1,3-dioxane-4,6-dione (25.2 g, 96%).

$^1$H NMR Spectrum: (DMSOd$_6$) 1.65 (s, 6H); 3.75 (s, 3H); 3.85 (s, 3H); 7.18 (d, 1H); 7.40 (s, 1H); 7. 70 (d, 1H); 8.65 (s, 1H); 11.2 (br s, 1H).

5-((3-Methoxy-4-methoxycarbonylanilino)methylene)-2,2-dimethyl-1,3-dioxane-4,6-dione (10 g, 29.8 mmol) was suspended in DOWTHERM A, (trade mark of Fluka Chemie AG), (125 ml) and heated to 180–190° C. over 30 minutes. The starting material dissolved at 100° C. and carbon dioxide came off at approximately 180° C. The heating was stopped after a further 30 minutes and the product precipitated out as the temperature dropped. Upon reaching 40° C. ether was added and the mixture was stirred for 30 minutes. The solid was collected by filtration, washed with ether and dried under vacuum to give 7-methoxy-6-methoxycarbonyl-1,4-dihydroquinolin-4-one (5.56 g, 80%).

1$^1$H NMR Spectrum: (DMSOd$_6$) 3.80 (s, 3H); 3.85 (s, 3H); 5.95 (d, 1H); 7.00 (s, 1H); 7.85 (d, 1H); 8.40 (s, 1H); 11.6 (br s, 1H); MS-ESI: 234 [MH]$^+$;

| Elemental analysis: | Found | C 61.3 | H 4.6 | N 5.8 |
| --- | --- | --- | --- | --- |
| $C_{12}H_{11}NO_4$ | Requires | C 61.8 | H 4.8 | N 6.0% |

A mixture of 7-methoxy-6-methoxycarbonyl-1,4-dihydroquinolin-4-one (5.4 g, 23 mmol), DMF (0.4 ml) and thionyl chloride (75 ml) was heated at reflux for 2 hours and then stirred at ambient temperature for a further 2 hours. The excess thionyl chloride was removed by evaporation and by azeotroping with toluene. The residue was suspended in methylene chloride and washed with saturated aqueous sodium hydrogen carbonate solution. The organic layer was separated, dried by passing through phase separating paper and the solvent was removed by evaporation. The residue was suspended in ether, collected by filtration, washed with hexane and dried to give 4-chloro-7-methoxy-6-methoxycarbonylquinoline (4.06 g, 70%) as an orange solid.

$^1$H NMR Spectrum: (DMSOd$_6$) 3.86 (s, 3H); 3.98 (s, 3H); 7.58 (s, 1H); 7.64 (d, 1H); 8.40 (s, 1H); 8.82 (d, 11H); MS-ESI: 252 [MH]$^+$.

EXAMPLE 56

3-Morpholinopropylamine (290 mg, 2 mmol) was added to a solution of 6-carboxy-4-(4-chloro-2-fluoroanilino)-7-methoxyquinoline (200 mg, 0.5 mmol), 1-(3-dimethylaminopropyl)-3-ethylcarbodiimide hydrochloride (191 mg, 1 mmol) and 1-hydroybenzotriazole hydrate (135 mg, 1 mmol) in DMF (15 ml). The mixture was stirred at ambient temperature for 2 hours. The solution was partitioned between water (100 ml) and methylene chloride. The organic layer was washed with brine and dried by passing through phase separating paper. The solvent was removed by evaporation and the crude product was purified by flash chromatography eluting with methylene chloride/methanol (99/1 increasing to 90/10). The pure fractions were combined and the solvent was removed by evaporation. The remaining oil was dissolved in methanol and an ethereal solution of hydrogen chloride was added. The solvent was removed by evaporation and the solid was dried overnight in a vacuum 1 oven at 40° C. to give 4-(4-chloro-2-fluoroanilino)-7-methoxy-6-(N-[3-morpholinopropyl]carbamoyl)quinoline (95 mg, 33%).

$^1$H NMR Spectrum: (DMSOd$_6$) 2.00 (br s, 2H); 3.30 (br s, 8H); 3.90 (br s, 5H); 4.05 (s, 3H); 6.45 (s, 1H); 7.45 (d, 1H); 7.6 (m, 2H); 7.75 (d, 1H); 8.50 (s, 1H); 8.70 (s, 1H); 9.20 (s, 1H); MS-ESI: 473 [MH]$^+$.

The starting material was prepared as follows:

A mixture of 4-(4-chloro-2-fluoroanilino)-7-methoxy-6-methoxycarbonylquinoline (1.79 g, 4.9 mmol), (prepared as described in Example 55), and sodium hydroxide (0.6 g, 15 mmol) in methanol (75 ml) and water (5 ml) was heated at 70° C. for 4 hours. The mixture was allowed to cool and the volatiles were removed by evaporation. The solid residue was suspended in water and acetic acid was added to adjust the aqueous suspension to pH5. The mixture was stirred for 15 minutes and the solid product was collected by filtration, washed with water and then acetone and finally ether, and dried to give 6-carboxy-4-(4-chloro-2-fluoroanilino)-7-methoxyquinoline (1.55 g, 90%).

$^1$H NMR Spectrum: (DMSOd$_6$) 3.92 (s, 3H); 6.25 (m, 1H); 7.30 (m, 2H); 7.40 (t, 1H); 7.57 (dd, 1H); 8.135 (m, 1H); 8.72 (s, 1H); MS-ESI: 347 [MH]$^+$.

| Elemental analysis: | Found | C 52.9 | H 3.9 | N 7.3 |
| --- | --- | --- | --- | --- |
| $C_{17}H_{12}N_2O_3ClF$ 2.15$H_2O$ | Requires | C 53.0 | H 4.3 | N 7.3% |

EXAMPLE 57

A suspension of 4-chloro-7-methoxy-6-methoxycarbonylquinoline (0.252 g, 1 mmol), (prepared as described for the starting material in Example 55), and 2-fluoro-5-hydroxy-4-methylaniline (0.15 g, 1.2 mmol), (prepared as described for the starting material in Example 1), in cyclohexanol (5 ml) containing 1M ethereal hydrogen chloride (1.2 ml) was heated at 100° C. for 2 hours. The mixture was cooled to ambient temperature and diluted with ether. The solid was collected by filtration then absorbed onto silica using methylene chloride/methanol (1/1) containing ammonium hydroxide (1 ml). The product was eluted with methylene chloride/methanol (100/0 increasing to 94:6). Removal of the solvent by evaporation and trituration of the solid with ether followed by collection of the solid by filtration gave 4-(2-fluoro-5-hydroxy-4-methylanilino)-7-methoxy-6-methoxycarbonylquinoline as a cream solid. (195 mg, 54%).

$^1$H NMR Spectrum: (DMSOd$_6$) 2.10 (s, 3H); 3.85 (s, 3H); 3.90 (s, 3H); 6.25 (br s, 1H); 6.75 (d, 1H); 77.5 (d, 1H); 7.35 (s, 1H); 8.40 (br s, 1H); 8.75 (s, 1H); 9.0 (br s, 1H); 9.45 (s, 1H); MS-ESI: 357 [MH]$^+$;

| Elemental analysis: | Found | C 63.5 | H 4.8 | N 7.7 |
| --- | --- | --- | --- | --- |
| $C_{19}H_{17}N_2O_4F$ | Requires | C 64.0 | H 4.8 | N 7.8% |

EXAMPLE 58

A suspension of 7-benzyloxy-4-chloro-6-cyanoquinoline (2 g, 6.8mmol), 4-chloro-2-fluoroaniline (1.1 g, 7.5 mmol) in isopropanol (50 ml) containing 1M ethereal hydrogen chloride (8 ml) was heated at reflux for 2 hours. After cooling to ambient temperature ether was added. The precipitate was collected by filtration, washed with isopropanol, followed by ether and dried under vacuum to give 7-benzyloxy-4-(4-chloro-2-fluoroanilino)-6-cyanoquinoline hydrochloride (2.41 g, 81%).

$^1$H NMR Spectrum: (DMSOd$_6$) 5.45 (s, 2H); 6.60 (dd, 1H);7.50 (m, 8H); 7.75 (s, 1H); 7.80 (dd, 1H); 8.55 (d, 1H); 9.45 (s, 1H); MS–ESI: 404 [MH]$^+$;

| Elemental analysis: | Found | C 61.9 | H 3.7 | N 9.2 |
| --- | --- | --- | --- | --- |
| $C_{23}H_{15}N_3OClF$ 0.4H$_2$O 1HCl | Requires | C 61.7 | H 3.8 | N 9.4% |

The starting material was prepared as follows:

Sodium hydride (2.7 g, 67.5 mmol) was suspended in NMP (75 ml) and benzyl alcohol (7.3 g, 67.6 mmol) was added over 10 minutes. When the addition was complete the solution was stirred at 50° C. for 30 minutes. 4-Amino-3-chlorobenzonitrile (10.3 g, 67.5 mmol), (Synthesis 1985, 669), was added and the mixture was heated at 120–130° C. for 4 hours. After cooling to ambient temperature the mixture was partitioned between water and ether. The ether extracts were washed with brine, dried (MgSO$_4$), the insoluble materials were removed by filtration and the volatiles were removed by evaporation. The crude product was purified by flash chromatography eluting with ether/isohexanes (1/1 increasing to 1/0). The purified product was recrystallized from ethyl acetate/isohexanes to give 4-amino-3-benzyloxybenzonitrile (4.7 g, 31%).

$^1$H NMR Spectrum,; (DMSOd$_6$) 5.10 (s, 2H); 6.10 (s, 2H); 6.20 (d, 1H); 6.35 (s, 1H); 7.25 (d, 1H); 740 (m, 5H); MS–ESI: 225 [MH]$^+$.

4-Amino-3-benzyloxybenzonitrile (6.8 g, 16.9 mmol) was suspended in isopropanol at ambient temperature and heated at 50° C. to give a pale yellow solution. 2,2-Dimethyl-5-methoxymethylene-1,3-dioxane-4,6-dione (4.24 g, 22.8 mmol), (Montatsh. Chem. 1967, 98, 564), was added and the product came out of solution immediately to give a thick yellow slurry The mixture was heated at reflux for 30 minutes and cooled to ambient temperature. The precipitate was collected by filtration, washed with isopropanol, ether and isohexanes and dried under vacuum to give 5-((3-benzyloxy-4-cyanoanilino)methylene)-2,2-dimethyl-1,3-dioxane-4,6-dione (6.05 g, 94%).

$^1$H NMR Spectrum: (DMSOd$_6$) 1.65 (s, 6H); 5.3 (s, 2H); 7.40 (m, 6H); 7.65 (s, 1H); 7.75 (s, 1H); 8.75 (s, 1H); 11.25 (br s, 1H).

5-((3-Benzyloxy-4-cyanoanilino)methylene)-2,2-dimethyl-1,3-dioxane-4,6-dione (6 g, 15.9 mmol) was suspended in DOWTHERM A, (trade mark of Fluka Chemie AG), (100 ml) and heated to 190° C. The mixture was stirred for 1 hour at 190° C. Upon cooling to ambient temperature the product precipitated out. Ether (125 ml) was added and the suspension was stirred for 30 minutes. The product was collected by filtration, washed with ether and dried under vacuum to give 7-benzyloxy-6-cyano-1,4-dihydroquinolin-4-one (3.5 g) which was used without further purification in the next step.

A mixture of 7-benzyloxy-6-cyano-1,4-dihydroquinolin-4-one (3.5 g), thionyl chloride (50 ml) and DMF (10 drops) was heated at reflux for 3 hours. The volatiles were removed by evaporation and the residue was partitioned between water and methylene chloride. A saturated solution of sodium hydrogen carbonate was added until the aqueous phase became alkaline. The aqueous phase was extracted with methylene chloride, the organic phases were combined, washed with water and dried by passing through phase separating paper. Removal of the solvent by evaporation gave a solid which was triturated with ether (50 ml) and collected by filtration. The orange solid obtained was dried in a vacuum oven to give 7-benzyloxy-4-chloro-6-cyanoquinoline (2.28 g, 36% over the last two steps).

$^1$H NMR Spectrum: (DMSOd$_6$) 5.45 (s, 2H); 7.40 (m, 3H); 7.55 (d, 2H); 7.75 (d, 1H); 7.80 (d, 1H); 8.65 (s, 1H); 8.90 (s, 1H).

EXAMPLE 59

A mixture of 4-(4-chloro-2-fluoroanilino)-6-cyano-7-hydroxyquinoline (1 95 mg, 0.6 mmol), 4-(3-chloropropyl) morpholine (124 mg, 0.76 mol), (J. Amer. Chem. Soc. 1945, 67, 736), potassium carbonate (172 mg, 1.2 mmol) and DMF (5 ml) was heated at 100° C. for 6 hours. The mixture was cooled to ambient temperature, and was partitioned between water and methylene chloride. The organic layer was dried (MgSO$_4$), insoluble materials were removed by filtration and silica (2 g) was added to the filtrate. The solvent was removed by evaporation and the powder obtained was purified by flash chromatography eluting with methylene chloride/methanol/ammonia (100/2/0.5 increasing to 100/20/1). Removal of the volatiles by evaporation gave an oil which was triturated with ether, collected by filtration and dried under vacuum to give 4-(4-chloro-2-fluoroanilino)-6-cyano-7-(3-morpholinopropoxy)quinoline (150 mg, 55%).

$^1$H NMR Spectrum: (DMSOd$_6$) 1.95 (m, 2H); 2.35 (m, 4H); 2.50 (m, 2H); 3.55 (m, 4H); 4.25 (m, 2H); 6 40 (br s, 1H); 7.40 (m, 3H); 7.60 (d, 1H); 8.45 (d, 1H); 8.90 (s, 1H); 9.15 (s, 1H); M—ESI: 441 [MH]$^+$;

| Elemental analysis: | Found | C 62.6 | H 5.0 | N 12.6 |
| --- | --- | --- | --- | --- |
| $C_{23}H_{22}N_4O_{2ClF}$ | Requires | C 62.7 | H 5.1 | N 12.7% |

The starting material was prepared as follows:

A suspension of 7-benzyloxy-4-(4-chloro-2-fluoroanilino)-cyanoquinoline hydrochloride (2.2 g, 5mmol), (prepared as described in Example 58), in TFA (35 ml) was heated at reflux for 9 hours. The volatiles were removed by evaporation and the residue was basified using a saturated solution of sodium hydrogen carbonate. The solution was purified by reverse phase C18 HPLC eluting with methanol/water (6/4) to give 444-chloro-2-fluoroanilino)-6-cyano-7-hydroxyquinoline (390 mg, 25%).

$^1$H NMR Spectrum: (DMSOd$_6$) 6.20 (m, 1H); 7.10 (s, 1H);7.40 (m, 2H); 7.60 (dd, 1H); 8.25 (d, 1H); 8.80 (s, 1H); MS–ESI: 314 [MH]$^+$.

EXAMPLE 60

Triflic anhydride (620 mg, 2.2 mmol) was added to 4-(4-chloro-2-fluoroanilino)-6-hydroxy-7- methoxyquinoline (637 mg, 2 mmol) in pyridine (6 ml) at 0° C. over 5 minutes. The mixture was stirred 1 hour and left to warm up to ambient temperature. The volatiles were removed by evaporation and the residue was partitioned between ethyl acetate and water containing 1M hydrochloric acid. The organic layer was dried (MgSO$_4$), insoluble materials were removed by filtration and the volatiles were removed by evaporation. The resulting crude oil was purified by flash chromatography eluting with ethyl acetate/isohexanes (1/9 increasing to 9/1). The volatiles were removed by evaporation and the residue was triturated with ether, collected by filtration, washed with ether and dried under vacuum to give 4-(4-chloro-2-fluoroanilino)-7-methoxy-6-trifluoromethylsulphonyloxyquinoline (560 mg, 62%).

$^1$H NMR Spectrum: (DMSOd$_6$) 4.00 (s, 3H); 6.35 (m, 1H); 7.35 (dd, 1H); 7.45 (t, 1H); 7.55 (s, 1H); 7.60 (dd, 1H); 8.45 (d, 1H); 8.50 (s, 1H); 9.00 (br s, 1H); MS (ESI): 451 [MH]$^+$;

| Elemental analysis: | Found | C 45.4 | H 2.4 | N 6.1 |
|---|---|---|---|---|
| C$_{17}$H$_{11}$N$_2$O$_4$ClF$_4$S | Requires | C 45.3 | H 2.5 | N 6.2% |

The starting material was prepared as follows:

A mixture of the potassium salt of 4-nitroguaiacol (10.15 g, 49 mmol), acetic anhydride (80 ml) DMAP (250 mg) and DMF (5 ml) was heated at 80° C. After stirring for 10 minutes, acetic arhydride was removed by evaporation and water was added to give a cream solid. The solid was collected by filtration, washed with water followed by ether and isohexanes to give 4-acetoxy-3-methoxynitrobenzene (9.84 g, 95%).

$^1$H NMR Spectrum: (DMSOd$_6$) 2.30 (s, 3H); 3.90 (s 3H); 7.40 (d, 1H); 7.90 (dd, 2H).

A solution of 4-acetoxy-3-methoxynitrobenzene (8.5 g, 40 mmol) in ethanol (175 ml) containing 10% palladium-on-charcoal catalyst (50% in water, 0.5 g) was stirred under hydrogen at atmospheric pressure for 1.5 hours. The catalyst was removed by filtration and the volatiles were removed by evaporation to give 4-acetoxy-3-methoxyaniline as an oil (6.92 g, 95%).

MS–ESI: 182 [MH]$^+$.

4-Acetoxy-3-methoxyaniline (6.95 g, 38.2 mmol) was dissolved in isopropanol (50 ml) and 212-dimethyl-5-methoxymethylene-1,3-dioxane4,6-dione (7.11 g, 38.2 mmol), (Montatsh. Chem. 1967, 98, 564), was added. The product immediately crystallised out. The mixture was heated briefly to 80° C. then cooled to ambient temperature. The solid product was collected by filtration and washed with isopropanol, followed by ether/isopropanol (1/1) and ether to give 5-((4-acetoxy-3-methoxyanilino)methylene)-2,2-dimethyl-1,3-dioxane-4.6-dione (11.83 g, 82%). $^1$H NMR Spectrum: (DMSOd$_6$) 1.65 (s, 6H); 2.25 (s, 3H); 3.80 (s, 3H); 7.15 (s, 2H); 7.45 (s, 1H); 8.6 (s, 1H); 11.20 (s, 1H).

A suspension of 5-((4-acetoxy-3-methoxyanilino) methylene)-2,2-dimethyl-1,3-dioxane-4,6-dione (11.5 g) in DOWTHERM A, (trade mark of Fluka Chemie AG), (125 ml) was heated at 195° C. for 30 minutes. After cooling, ether was added (100 ml) and the precipitate was collected by filtration. The solid was washed with ether and dried under vacuum to give 6-acetoxy-7-methoxy-1,4-dihydroquinolin-4-one which was used without further purification for the next step.

A solution of 6-acetoxy-7-methoxy-1,4-dihydroquinolin-4-one (6.2 g, 28 mmol) and thionyl chloride (75 ml) containing DMF (0.5 ml) was heated at reflux for 1 hour. The volatiles were removed by evaporation. The residue was suspended in methylene chloride (5 ml) and poured slowly into a stirred solution of methanol/ammonium hydroxide. The mixture was partitioned between water and methylene chloride and dried by passing through ,phase separating paper. Removal of the solvent by evaporation gave a solid which was triturated with ether, collected by filtration, washed with ether and dried under vacuum to give 4-chloro-6-hydroxy-7-methoxyquinoline.

$^1$H NMR Spectrum: (DMSOd$_6$) 3.95 (s, 3H); 7.38 (s, 1H); 7.42 (s, 1H); 7.45 (d, 1H); 8.50 (d, 1H); 10.3 (br s, 1H); MS–ESI: 210 [MH]$^+$.

A solution of 4-chloro-6-hydroxy-7-methoxyquinoline (3.0 g, 14 mmol) and 4-chloro-2-fluoroaniline (3.5 g, 23 mmol) in cyclohexanol (100 ml) containing 1M ethereal hydrogen chloride (16 ml) was heated at 155° C. for 18 hours. After cooling the mixture was diluted with ether and isohexanes and the precipitate was collected by filtration. The crude product was dissolved in a mixture of methylene chloride/methanol/ammonia (100/10/1) and silica (10 g) was added. The solvent was removed by evaporation and the resulting powder was purified by flash chromatography eluting with methylene chloride/methanol/ammonia (95/5/1 increasing to 80/20/1) to give 4-(4-chloro-2-fluoroanilino)-6-hydroxy-7-methoxyquinoline (1.12 g, 25%).

$^1$H NMR Spectrum: (DMSOd$_6$) 3.95 (s, 3H); 6.30 (m, 1H); 7.25 (s, 1H);7.35 (m, 2H); 7.55 (m, 2H); 8.20 (d, 1H); MS (ESI): 319 [MH]$^+$.

EXAMPLE 61

A solution of (4-chloro-2-fluoroanilino)-6-hydroxy-7-methoxyquinoline (210 mg, 0.66 mmol), (prepared as described for the starting material in Example 60), 4-(3-chloropropyl)morpholine (132 mg, 0.66 mmol), (J. Amer. Chem. Soc. 1945, 67, 736), potassium carbonate (182 mg, 1.2 mmol) and DMF (7.5 ml) was heated at 80° C. for 4 hours. The mixture was cooled to ambient temperature and partitioned between water and methylene chloride. The organic layer was washed with brine, dried by passing through phase separating paper and silica (2 g) was added. After removal of the solvent by evaporation the resulting powder was purified by flash chromatography eluting with methylene chloride/methanol/ammonia (100/2/0.5 increasing to 100/20/1). After removal of the volatiles by evaporation, the resulting oil was triturated with ether until it solidified. The solid was collected by filtration, washed with ether and dried under vacuum to give 4-(4-chloro-2-fluoroanilino)-7-methoxy-6-(3-morpholinopropoxy) quinoline (80 mg, 27%).

$^1$H NMR Spectrum: (DMSOd$_6$) 1.95 (m, 2H); 2.35 (m, 4H); 2.45 (m, 2H); 3.55 (m, 4H); 3.90 (s, 3H); 4.15 (m, 2H); 6.35 (m, 1H); 7.25 (s, 1H); 7.35 (dd, 1H); 7.40 (t, 1H); 7.60 (dd, 1H); 7.65 (s, 1H); 8.25 (d, 1H); MS–ESI: 446 [MH]$^+$;

| Elemental analysis: | Found | C 61.1 | H 5.9 | N 8.8 |
|---|---|---|---|---|
| C$_{23}$H$_{25}$N$_3$O$_3$ClF 0.3H$_2$O | Requires | C 61.2 | H 5.7 | N 9.3% |

EXAMPLE 62

4-(4-Chloro-2-fluoroanilino)-7-methoxy-6-trifluoromethylsulphonyloxyquinoline (560 mg, 1.2 mmol), (prepared as described in Example 60), was suspended in THF (40 ml) and toluene (40 ml) and degassed several times using alternatively vacuum and argon. Tetrakis(triphenylphosphine)palladium(0) (100 mg) and sodium tri-isopropylsilanethiolate (600 mg, 2.8 mmol), (Tet Lett 1994, 35, 3221), were added and the mixture was heated at reflux for 3 hours. The mixture was cooled to ambient temperature and 2-bromoethyl methyl ether (1.0 g, 7.2 mmol), DMF (20 ml) and 1M tetrabutylammonium fluoride in THF (10 ml) were added. After stirring for 1 hour at ambient temperature, the mixture was partitioned between water and ethyl acetate. The organic layer was washed with brine, dried ($MgSO_4$) and the volatiles were removed by evaporation. The residue was purified by flash chromatography eluting with ethyl acetate/isohexanes (25/75) followed by ethyl acetate/methanol (95/5). The solvent was removed by evaporation and the residue was triturated with ethyl acetate/ether (1/4), collected by filtration and dried under vacuum to give 4-(4-chloro-2-fluoroanilino)-7-methoxy-6-(2-methoxyethylthio)quinoline (210 mg, 43%).

$^1$H NMR Spectrum: ($DMSOd_6$) 3.20 (t, 2H); 3.25 (s, 3H); 3.60 (t, 2H); 3.95 (s, 3H); 6.35 (m, 1H); 71.25 (s, 1H); 7.35 (dd, 1H); 7.45 (t, 1H); 7.60 (dd, 1H). 8.05 (s, 1H); 8.3 (d, 1H); 8.8 (s, 1H); MS–ESI: 393 [MH]$^+$.

EXAMPLE 63

4-(4-Chloro-2-fluoroanilino)-7-methoxy-6-(2-methoxyethylthio)quinoline (175 mg, 0.45 mmol), (prepared as described in Example 62), was dissolved in methanol (40 ml), OXONE, (trade mark of E.I. du Pont de Nemours & Co.,Inc), (230 mg in 5 ml of water) was added and the mixture was stirred at ambient temperature for 30 minutes. More OXONE, (trade mark of E.I. du Pont de Nemours & Co.,Inc), (60 mg) was added and the mixture was stirred for a further hour. The mixture was diluted with 100 ml of water and extracted with methylene chloride (3×100 ml). The combined extracts were washed with brine, dried by passing through phase separating paper and the volatiles were removed by evaporation. The solid was purified on a Mega Bond Elute (trade mark of Varian Sample Preparation Products) column using first methylene chloride (100%) and gradually increasing the solvent polarity up to methylene chloride/methanol (95/5). The volatiles were removed by evaporation to give 4-(4-chloro-2-fluoroanilino)-7-methoxy-6-(2-methoxyethylsulphinyl)quinoline (120 mg, 66%).

$^1$H NMR Spectrum: ($DMSOd_6$) 2.85 (m, 1H); 3.25 (s, 3H); 3.40 (m, 1H); 3.65 (m, 1H); 3.80 (m, 1H); 3.95 (s 3H); 6.35 (m, 1H); 7.35 (dd, 1H); 7.40 (s, 1H); 7.45 (t, 1H); 7.55 (dd, 1H), 8.60 (s, 1H); 9.3 (s, 1H); MS (ESI): 409 [MH]$^+$.

EXAMPLE 64

The following illustrate representative pharmaceutical dosage forms containing the compound of formula I, or a pharmaceutically acceptable salt thereof (hereafter compound X), for therapeutic or prophylactic use in humans:

| (a) | Tablet I | mg/tablet |
|---|---|---|
| | Compound X | 100 |
| | Lactose Ph.Eur | 182.75 |
| | Croscarmellose sodium | 12.0 |
| | Maize starch paste (5% w/v paste) | 2.25 |
| | Magnesium stearate | 3.0 |

| (b) | Tablet II | mg/tablet |
|---|---|---|
| | Compound X | 50 |
| | Lactose Ph.Eur | 223.75 |
| | Croscarmellose sodium | 6.0 |
| | Maize starch | 15.0 |
| | Polyvinylpyrrolidone (5% w/v paste) | 2.25 |
| | Magnesium stearate | 3.0 |

| (c) | Tablet III | mg/tablet |
|---|---|---|
| | Compound X | 1.0 |
| | Lactose Ph.Eur | 93.25 |
| | Croscarmellose sodium | 4.0 |
| | Maize starch paste (5% w/v paste) | 0.75 |
| | Magnesium stearate | 1.0 |

| (d) | Capsule | mg/tablet |
|---|---|---|
| | Compound X | 10 |
| | Lactose Ph.Eur | 488.5 |
| | Magnesium stearate | 1.5 |

| (e) | Injection I | (50 mg/ml) |
|---|---|---|
| | Compound X | 5.0% w/v |
| | 1N Sodium hydroxide solution | 15.0% v/v |
| | 0.1N Hydrochloric acid (to adjust pH to Polyethylene glycol 400 Water for injection to 100% | 4.5% w/v |

| (f) | Injection II | 10 mg/ml) |
|---|---|---|
| | Compound X | 1.0% w/v |
| | Sodium phosphate BP | 3.6% w/v |
| | 0.1N Sodium hydroxide solution | 15.0% v/v |
| | Water for injection to 100% | |

| (g) | Injection III | (1 mg/ml, buffered to pH6) |
|---|---|---|
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

Note
The above formulations may be obtained by conventional procedures well known in the pharmaceutical art. The tablets (a)-(c) may be enteric coated by conventional means, for example to provide a coating of cellulose acetate phthalate.

What is claimed is:
1. A compound of the formula Id:

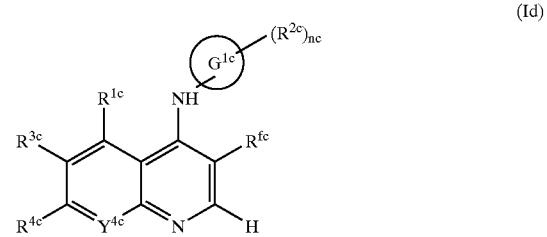

wherein:
$G^{1c}$ represents phenyl or 1H-indazol-6-yl;
$Y^{4c}$ represents C—H;
$R^{fc}$ represents hydrogen or fluoro;
$R^{2c}$ represents hydroxy, halogeno, $C_{1-3}$alkyl, $C_{1-3}$alkoxy, $C_{1-3}$alkanoyloxy, trifluoromethyl, cyano, amino or nitro;

nc is an integer from 1 to 3;

$R^{1c}$ represents hydrogen, hydroxy, methoxy, amino, nitro or halogeno;

$R^{3c}$ represents hydrogen, hydroxy, halogeno, cyano, nitro, trifluoromethyl, $C_{1-3}$alkyl, $C_{1-3}$alkoxy, $C_{1-3}$alkylthio, or —$NR^{6c}R^{7c}$ (wherein $R^{6c}$ and $R^{7c}$, which may be the same or different, each represents hydrogen or $C_{1-3}$alkyl), and additionally $R^{3c}$ may have any of the values of $R^{5c}$—$X^{1c}$— (wherein $R^{5c}$ and $X^{1c}$ are as defined below);

$R^{4c}$ represents cyano, —$NR^{8c}R^{9c}$ (wherein $R^{8c}$ and $R^{9c}$, which may be the same or different, each represents $C_{1-3}$alkyl), or a group $R^{5c}$—$X^{1c}$ represents —OCO—, —S—, —SO—, —$SO_2$—, —$CONR^{11c}$, —$SO_2NR^{12c}$— or —$NR^{14c}$— (wherein $R^{11c}$, $R^{12c}$ and $R^{14c}$ each independently represents hydrogen, $C_{1-3}$alkyl or $C_{1-3}$alkoxy$C_{2-3}$alkyl), and $R^{5c}$ is selected from one of the following eight groups:

1) $C_{1-5}$alkyl which may be unsubstituted or which may be substituted with one or more groups selected from hydroxy and amino;

2) $C_{1-5}$alkyl$X^{2c}COR^{15c}$ (wherein $X^{2c}$ represents —O— or —$NR^{16c}$— (wherein $R^{16c}$ represents hydrogen, $C_{1-3}$alkyl or $C_{1-3}$alkoxy$C_{2-3}$alkyl) and $R^{15c}$ represents —$NR^{17c}R^{18c}$— or —$OR^{19c}$— (wherein $R^{17c}$, $R^{18c}$ and $R^{19c}$ which may be the same or different each represents hydrogen, $C_{1-3}$alkyl or $C_{1-3}$alkoxy$C_{2-3}$alkyl));

3) $C_{1-5}$alkyl$X^{3c}R^{20c}$ (wherein $X^{3c}$ represents —O—, —S—, —SO—, —$SO_2$—, —OCO—, —$NR^{21c}CO$—, —$CONR^{22c}$, —$SO_2NR^{23c}$—, —$NR^{24c}SO^2$— or —$NR^{25c}$— (wherein $R^{21c}$, $R^{22c}$, $R^{23c}$, $R^{24c}$ and $R^{25c}$ each independently represents hydrogen, $C_{1-3}$alkyl or $C_{1-3}$alkoxy$C_{2-3}$alkyl) and $R^{20c}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);

4) $C_{1-5}$alkyl$X^{4c}C_{1-5}$alkyl$X^{5c}R^{26c}$ (wherein $X^{4c}$ and $X^{5c}$ which may be the same or different are each —O—, —S—, —SO—, —$SO_2$—, —$NR^{27c}CO$—, —$CONR^{28c}$—, —$SO_2NR^{29c}$—, —$NR^{30c}SO_2$— or —$NR^{31c}$— (wherein $R^{27c}$, $R^{28c}$, $R^{29c}$, $R^{30c}$ and $R^{31c}$ each independently represents hydrogen, $C_{1-3}$alkyl or $C_{1-3}$alkoxy$C_{2-3}$alkyl) and $R^{26c}$ represents hydrogen or $C_{1-3}$alkyl);

5) $C_{1-5}$alkyl$R^{32c}$ (wherein $R^{32c}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);

6) $(CH2)_{qc}X^{6c}R^{33c}$ (wherein qc is an integer from 0 to 5, $X^{6c}$ represents a direct bond, —O—, —S—, —SO—, —$NR^{34c}CO$, $CONR^{35c}$, —$SO_2N^{36c}$—, —$NR^{37c}SO_2$— or —$NR^{38c}$— (wherein $R^{34c}$, $R^{35c}$, $R^{36c}$, $R^{37c}$ and $R^{38c}$ each independently represents hydrogen, $C_{1-3}$alkyl or $C_{1-3}$alkoxy$C_{2-3}$alkyl) and $R^{33c}$ is a phenyl group, a pyridone group or a 5 or 6 membered aromatic heterocyclic group with 1 to 3 heteroatoms selected from O, N and S, which phenyl, pyridone or aromatic heterocyclic group may carry up to 5 substituents selected from hydroxy, halogeno, $C_{1-4}$alkyl, $C_{1-4}$alkoxy, $C_{1-4}$hydroxyalkyl, $C_{1-4}$hydroxyalkoxy, carboxy, cyano, —$CONR^{39c}R^{40c}$ and —$NR^{41c}COR^{42c}$ (wherein $R^{39c}$, $R^{40c}$, $R^{41c}$ and $R^{42c}$, which may be the same or different, each represents hydrogen or $C_{1-4}$alkyl));

7) $C_{2-6}$alkenyl$R^{32c}$ (wherein $R^{32c}$ is as defined above); and

8) $C_{2-6}$alkynyl$R^{32c}$ (wherein $R^{32c}$ is as defined above); or a salt thereof.

2. The compound as claimed in claim 1 wherein $R^{3c}$ represents hydrogen, hydroxy, cyano, nitro, trifluoromethyl, methyl, ethyl, methoxy, ethoxy or methoxycarbonyl.

3. The compound as claimed in claim 1 wherein $R^{4c}$ represents $R^{5c}$—$X^{1c}$— (wherein $X^{1c}$ represents —S—) and $R^{5c}$ is selected from one of the following eight groups:

1) $C_{1-4}$alkyl, or $C_{2-4}$alkyl which may be unsubstituted or substituted with one or two groups selected from hydroxy and amino;

2) $C_{2-3}$alkyl$X^{2c}COR^{15c}$ (wherein $X^{2c}$ is as defined in claim 1 and $R^{15c}$ represents —$NR^{17c}R^{18c}$— or —$OR^{19c}$— (wherein $R^{17c}$, $R^{18c}$ and $R^{19c}$ which may be the same or different each represents hydrogen, $C_{1-2}$alkyl or $C_{1-2}$alkoxyethyl));

3) $C_{2-3}$alkyl$X^{3c}R^{20c}$ (wherein $X^{3c}$ is as defined in claim 1 and $R^{20c}$ is a group selected from $C_{1-3}$alkyl, cyclopentyl, cyclohexyl, pyrrolidinyl and piperidinyl which group is linked to $X^{3c}$ through a carbon atom and which $C_{1-3}$alkyl group may bear one or two substituents selected from oxo, hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{2-3}$alkyl$X^{4c}C_{2-3}$alkyl$X^{5c}R^{26c}$ (wherein $X^{4c}$ and $X^{5c}$ are as defined in claim 1) and $R^{26c}$ represents hydrogen or $C_{1-2}$alkyl);

5) $C_{1-4}$alkyl$R^{43c}$ (wherein $R^{43c}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-4}$alkyl through a carbon atom and which group may carry one or two substituents selected from oxo, hydroxy, halogeno, $C_{1-2}$alkyl, $C_{1-2}$hydroxyalkyl and $C_{1-2}$alkoxy) or $C_{2-4}$alkyl$R^{44c}$ (wherein $R^{44c}$ is a group selected from morpholino, thiomorpholino, pyrrolidin-1-yl, piperazin-1-yl and piperidino which group may carry one or two substituents selected from oxo, hydroxy, halogeno, $C_{1-2}$alkyl, $C_{1-2}$hydroxyalkyl and $C_{1-2}$alkoxy); and 6) $(CH_2)_{qc}X^{6c}R^{33c}$ (wherein $X^{6c}$ is as defined in claim 1; qc is an integer from 1 to 3 if $X^{6c}$ is a direct bond and qc is 2 or 3 if $X^{6c}$ is other than a direct bond; and $R^{33c}$ is a phenyl group, a pyridone group or a 5 or 6 membered aromatic heterocyclic group with 1 to 2 heteroatoms selected from O, N and S, which phenyl group, pyridone group or aromatic heterocyclic group may be substituted as defined in claim 1);

7) $C_{4-5}$alkenyl$R^{45c}$ (wherein $R^{45c}$ represents $R^{43c}$ or $R^{44c}$ as defined above); and 8) $C_{4-5}$alkynyl$R^{45c}$ (wherein $R^{45c}$ represents $R^{43c}$ or $R^{44c}$ as defined above).

4. The compound as claimed in claim 3 wherein $R^{5c}$ is methyl, ethyl, 2-hydroxyethyl, 3-hydroxypropyl, 2-methoxyethyl, 3-methoxypropyl, 2-(methylsulphinyl) ethyl, 2-(methylsulphonyl)ethyl, 2-(N,N- dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, benzyl, 2-(4-pyridyloxy)ethyl, 2-(4-pyridylamino)ethyl, 2-(4-oxo-1,4-dihydro-1-pyridyl)ethyl, 3-(3-pyridyl)propyl, 2-(N-(1-methylimidazol-4-ylsulphonyl)-N-methyl)amino ethyl, 2-((N-methyl-N-4-pyridyl)amino)ethyl, 2-(4-oxidomorpholino)ethyl, 3-(4-oxidomorpholino)propyl, 3-(4-oxo-1,4-dihydro-1-pyridyl)propyl, 3-(1,2,4-triazol-1-yl)propyl, 3-(1,2,4-triazol-4-yl)propyl, 3-(4-pyridyloxy)propyl, 3-(4-pyridylamino)propyl, 2-(2-methylimidazol-1-yl)ethyl, 3-(2-methylimidazol-1-yl)propyl, 2-(5-methyl-1,2,4-triazol-1-yl)ethyl, 3-(5-methyl-1,2,4-triazol-1-yl)propyl, 3-(imidazol-1-yl)propyl,3-(1,2,3-triazol-1-yl)propyl, 3-(1,2,3-triazol-2-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl)propyl or 3-(methylsulphonyl)propyl.

5. The compound as claimed in claim 3 wherein $R^{5c}$ is methyl, ethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl)ethyl, 2-sulphamoyiethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, benzyl, 2-(4-pyridyloxy)ethyl, 2-(4-pyridylamino)ethyl or 2-(4-oxo-1,4-dihydro-1-pyridyl)ethyl.

6. A compound as claimed in claim 1 selected from:
  4-(4-chloro-2-fluoroanilino)-6-methoxy-7-(3-pyrrolidin-1-ylpropoxy)quinoline;
  4-(4-chloro-2-fluoroanilino)-7-(3-(dimethylamino)propoxy)-6-methoxyquinoline;
  4-(4-chloro-2-fluoroanilino)-6-methoxy-7-(2-([1,2,4]-triazol-1-yl)ethoxy)quinoline;
  4-(4-chloro-2-fluoroanilino)-7-(3-hydroxypropoxy)-6-methoxyquinoline;
  4-(4-chloro-2-fluoroanilino)-7-methoxy-6-(3-morpholinopropoxy)quinoline;
  7-benzyloxy-4-(3-hydroxy-4-methylanilino)-6-methoxyquinoline; and
  4-(4-chloro-2-fluoroanilino)-7-methoxy-6-(N-[3-morpholinopropyl]carbamoyl)quinoline; and salts thereof.

7. A compound as claimed in claim 1 selected from:
  4-(2-fluoro-5-hydroxy-4-methylanilino)-7-methoxy-6-methoxycarbonylquinoline;
  6-cyano-4-(2-fluoro-5-hydroxy-4-methylanilino)-7-(2-methoxyethoxy)quinoline;
  4-(4-chloro-2-fluoro-5-hydroxyanilino)-6-methoxy-7-(2-methoxyethoxy)quinoline;
  4-(4-chloro-2-fluoro-5-hydroxyanilino)-6-methoxy-7-(3-(3-pyridyl)propoxy)quinoline;
  4-(4-chloro-2-fluoro-5-hydroxyanilino)-6-methoxy-7-(2-methylthiazol-4-ylmethoxy)-quinoline;
  4-(2-fluoro-5-hydroxy-4-methylanilino)-6-methoxy-7-(2-methoxyethoxy)quinoline;
  4-(4-chloro-2-fluoro-5-hydroxyanilino)-6-methoxy-7-(3-pyrrolidin-1-ylpropoxy)quinoline;
  4-(2-fluoro-5-hydroxy-4-methylanilino)-6-methoxy-7-(3-pyrrolidin-1-ylpropoxy)quinoline;
  4-(3-hydroxy-4-methylanilino)-6-methoxy-7-(2-methoxyethoxy)quinoline;
  6-cyano-4-(2-fluoro-5-hydroxy-4-methylanilino)-7-(3-morpholinopropoxy)quinoline;
  4-(4-chloro-2-fluoro-5-hydroxyanilino)-6-methoxy-7-(3-morpholinopropoxy)quinoline;
  4-(2-fluoro-5-hydroxy-4-methylanilino)-6-methoxy-7-(3-morpholinopropoxy)quinoline;
  4-(4-chloro-2-fluoro-5-hydroxyanilino)-6-methoxy-7-(4-pyridylmethoxy)quinoline;
  4-(4-chloro-2-fluoro-5-hydroxyanilino)-6-methoxy-7-(2-morpholinoethoxy)quinoline;
  6-cyano-4-(2-fluoro-5-hydroxy-4-methylanilino)-7-methoxyquinoline; and
  4-(4-chloro-2-fluoroanilino)-7-(2-hydroxyethoxy)-6-methoxyquinoline; and salts thereof.

8. A compound as claimed in claim 1 selected from:
  6-cyano-4-(3-hydroxy-4-methylanilino)-7-(2-methoxyethoxy)quinoline;
  7-benzyloxy-4-(4-chloro-2-fluoro-5-hydroxyanilino)-6-methoxyquinoline;
  7-benzyloxy-4-(4-bromo-2-fluoro-5-hydroxyanilino)-6-methoxyquinoline;
  4-(4-chloro-2-fluoro-5-hydroxyanilino)-6-methoxy-7-(1-methylimidazol-2-ylmethoxy)-quinoline;
  4-(4-chloro-2-fluoroanilino)-6-cyano-7-(2-methoxyethoxy)quinoline;
  4-(4-chloro-2-fluoroanilino)-6-cyano-7-(3-morpholinopropoxy)quinoline;
  4-(4-chloro-2-fluoroanilino)-6-methoxy-7-(2-methoxyethoxy)quinoline; and
  4-(4-chloro-2-fluoroanilino)-6-methoxy-7-(3-morpholinopropoxy)quinoline; and salts thereof.

9. A compound of the formula Id:

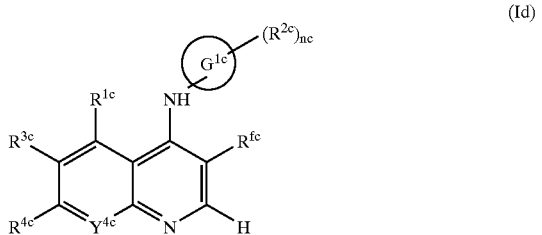

wherein:
G$^{1c}$ represents phenyl or 1H-indazol-6-yl;
Y$^{4c}$ represents C—H;
R$^{fc}$ represents hydrogen or fluoro;
R$^{2c}$ represents hydroxy, halogeno, C$_{1-3}$alkyl, C$_{1-3}$alkoxy, C$_{1-3}$alkanoyloxy, trifluoromethyl, cyano, amino or nitro;
nc is an integer from 0 to 5;
R$^{1c}$ represents hydrogen, hydroxy, methoxy, amino, nitro or halogeno;
R$^{3c}$ represents hydrogen, hydroxy, halogeno, cyano, nitro, trifluoromethyl, C$_{1-3}$alkyl, C$_{1-3}$alkoxy, C$_{1-3}$alkylthio, or —NR$^{6c}$R$^{7c}$ (wherein R$^{6c}$ and R$^{7c}$, which may be the same or different, each represents hydrogen or C$_{1-3}$alkyl), and additionally R$^{3c}$ may have any of the values of R$^{5c}$—X$^{1c}$— (wherein R$^{5c}$ and X$^{1c}$ are as defined below);
R$^{4c}$ represents cyano, —NR$^{8c}$R$^{9c}$ (wherein R$^{8c}$ and R$^{9c}$, which may be the same or different, each represents C$_{1-3}$alkyl), or a group R$^{5c}$—X$^{1c}$— wherein X$^{1c}$ represents —O—, —CH$_2$—, —OCO—, —S—, —SO—, —SO$_2$—, —NR$^{10c}$CO—, —CONR$^{11c}$—, —SO$_2$NR$^{12c}$—, —NR$^{13c}$SO$_2$— or —NR$^{14c}$— (wherein R$^{10c}$, R$^{11c}$, R$^{12c}$, R$^{13c}$ and R$^{14c}$ each independently represents hydrogen, C$_{1-4}$alkyl or C$_{1-3}$alkoxyC$_{2-3}$ alkyl), and R$^{5c}$ is selected from one of the following seven groups:
1) C$_{1-5}$alkylX$^{2c}$COR$^{15c}$ (wherein X$^{2c}$ represents —O— or —NR$^{16c}$— (wherein R$^{16c}$ represents hydrogen, C$_{1-3}$alkyl or C$_{1-3}$alkoxyC$_{2-3}$alkyl) and R$^{15c}$ represents —NR$^{17c}$R$^{18c}$— or —OR$^{19c}$— (wherein R$^{17c}$, R$^{18c}$ and R$^{19c}$ which may be the same or different each represents hydrogen, C$_{1-4}$alkyl or C$_{1-3}$alkoxyC$_{2-3}$alkyl));
2) C$_{1-5}$alkylX$^{3c}$R$^{20c}$ (wherein X$^{3c}$ represents —O—, —S—, —SO—, —SO$_2$—, —OCO—, —NR$^{21c}$CO—, —CONR$^{22c}$—, —SO$_2$NR$^{23c}$—, —NR$^{24c}$SO$_2$— or —NR$^{25c}$— (wherein R$^{21c}$, R$^{22c}$, R$^{23c}$, R$^{24c}$ and R$^{25c}$ each independently represents hydrogen, C$_{1-3}$alkyl or C$_{1-3}$alkoxyC$_{2-3}$alkyl) and R$^{20c}$ represents hydrogen, C$_{1-3}$alkyl, cyclopentyl, cyclohexyl or a 5 or 6 membered saturated heterocyclic group with one or two heteroatoms, selected independently from O, S and N, which C$_{1-3}$alkyl group may bear one or two substituents selected from oxo, hydroxy, halogeno and C$_{1-4}$alkoxy and which cyclic group may bear one or two substituents selected from oxo, hydroxy, halogeno, C$_{1-4}$alkyl, C$_{1-4}$hydroxyalkyl and C$_{1-4}$alkoxy);
3) C$_{1-5}$alkylX$^{4c}$C$_{1-5}$alkylX$^{5c}$R$^{26c}$ (wherein X$^{4c}$ and X$^{5c}$ which may be the same or different are each —O—, —S—, —SO—, —SO$_2$—, —NR$^{27c}$CO—, —CONR$^{28c}$—, —SO$_2$NR$^{29c}$—, —NR$^{30c}$SO$_2$— or —NR$^{31c}$— (wherein R$^{27c}$, R$^{28c}$, R$^{29c}$, R$^{30c}$ and R$^{31c}$ each independently represents hydrogen, C$_{1-3}$alkyl or C$_{1-3}$alkoxyC$_{2-3}$alkyl) and R$^{26c}$ represents hydrogen or C$_{1-3}$alkyl);
4) C$_{1-5}$alkylR$^{32c}$ (wherein R$^{32c}$ is a 5 or 6 membered saturated heterocyclic group with one or two heteroatoms, selected independently from O, S and N, which heterocyclic group may bear one or two substituents selected from oxo, hydroxy, halogeno, C$_{1-4}$alkyl, C$_{1-4}$hydroxyalkyl and C$_{1-4}$alkoxy);
5) (CH$_2$)$_{qc}$X$^{6c}$R$^{33c}$ (wherein qc is an integer from 0 to 5, X$^{6c}$ represents a direct bond, —O—, —S—, —SO—, —SO$_2$—, NR$^{34c}$CO—, CONR$^{35c}$C—, —SO$_2$NR$^{36c}$—, —NR$^{37c}$SO$_2$— or NR$^{38c}$— (wherein R$^{34c}$, R$^{35c}$, R$^{36c}$, R$^{37c}$ and R$^{38c}$ each independently represents hydrogen, C$_{1-3}$alkyl or C$_{1-3}$alkoxyC$_{2-3}$alkyl) and R$^{33c}$ is a pyridone group or a 5 or 6 membered aromatic heterocyclic group with 1 to 3 heteroatoms selected from O, N and S, which pyridone or aromatic heterocyclic group may carry up to 5 substituents selected from hydroxy, halogeno, C$_{1-4}$alkyl, C$_{1-4}$alkoxy, C$_{1-4}$hydroxyalkyl, C$_{1-4}$hydroxyalkoxy, carboxy, cyano, —CONR$^{39c}$R$^{40c}$ and —NR$^{41c}$COR$^{42c}$ (wherein R$^{39c}$, R$^{40c}$, R$^{41c}$ and R$^{42c}$, which may be the same or different, each represents hydrogen or C$_{1-4}$alkyl));
6) C$_{2-6}$alkenylR$^{32c}$ (wherein R$^{32c}$ is as defined above); and
7) C$_{2-6}$alkynylR$^{32c}$ (wherein R$^{32c}$ is as defined above);
or a salt thereof.

10. The compound as claimed in claim 9 wherein R$^{4c}$ represents R$^{5c}$—X$^{1c}$— (wherein X$^{1c}$ represents —O—, —S—,—NR$^{10c}$CO— or —NR$^{13c}$SO$_2$— (wherein R$^{10c}$ and R$^{13c}$ each independently represents hydrogen or C$_{1-2}$alkyl) and R$^{5c}$ is selected from one of the following seven groups:
1) C$_{2-3}$alkylX$^{2c}$COR$^{15c}$ (wherein X$^{2c}$ is as defined in claim 1 and R$^{15c}$ represents —NR$^{17c}$R$^{8c}$— or —OR$^{19c}$— (wherein R$^{17c}$, R$^{18c}$ and R$^{19c}$ which may be the same or different each represents hydrogen, C$_{1-2}$alkyl or C$_{1-2}$alkoxyethyl));
2) C$_{2-3}$alkylX$^{3c}$R$^{20c}$ (wherein X$^{3c}$ is as defined in claim 1 and R$^{20c}$ is a group selected from C$_{1-3}$alkyl, cyclopentyl, cyclohexyl, pyrrolidinyl and piperidinyl which group is linked to X$^{3c}$ through a carbon atom and which C$_{1-3}$alkyl group may bear one or two substituents selected from oxo, hydroxy, halogeno and C$_{1-2}$alkoxy and which cyclopentyl, cyclohexyl, pyrrolidinyl or piperidinyl group may carry one substituent selected from oxo, hydroxy, halogeno, C$_{1-2}$alkyl, C$_{1-2}$hydroxyalkyl and C$_{1-2}$alkoxy);
3) C$_{2-3}$alkylX$^{4c}$C$_{2-3}$alkylX$^{5c}$R$^{26c}$ (wherein X$^{4c}$ and X$^{5c}$ are as defined in claim 1) and R$^{26c}$ represents hydrogen or C$_{1-2}$alkyl);
4) C$_{1-4}$alkylR$^{43c}$ (wherein R$^{43c}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to C$_{1-4}$alkyl through a carbon atom and which group may carry one or two substituents selected from oxo, hydroxy, halogeno, C$_{1-2}$alkyl, C$_{1-2}$hydroxyalkyl and C$_{1-2}$alkoxy) or C$_{2-4}$alkylR$^{44c}$ (wherein R$^{44c}$ is a group selected from morpholino, thiomorpholino, pyrrolidin-1-yl, piperazin-1-yl and piperidino which group may carry one or two substituents selected from oxo, hydroxy, halogeno, C$_{1-2}$alkyl, C$_{1-2}$hydroxyalkyl and C$_{1-2}$alkoxy); and
5) (CH$_2$)$_{qc}$X$^{6c}$R$^{33c}$ (wherein X$^{6c}$ is as defined in claim 1; qc is an integer from 1 to 3 if X$^{6c}$ is a direct bond and qc is 2 or 3 if X$^{6c}$ is other than a direct bond; and R$^{33c}$ is a phenyl group, a pyridone group or a 5 or 6 membered aromatic heterocyclic group with 1 to 2 heteroatoms selected from O, N and S, which phenyl group, pyridone group or aromatic heterocyclic group may be substituted as defined in claim 1);

6) $C_{4-5}$alkenyl$R^{45c}$ (wherein $R^{45c}$ represents $R^{43c}$ or $R^{44c}$ as defined above); and 7) $C_{4-5}$alkynyl$R^{45c}$ (wherein $R^{45c}$ represents $R^{43c}$ or $R^{44c}$ as defined above).

11. The compound as claimed in claim 9 wherein $R^{3c}$ represents hydrogen, hydroxy, cyano, nitro, trifluoromethyl, methyl, ethyl, methoxy, ethoxy, 3-morpholinopropoxy or 3-morpholinopropylcarbamoyl.

12. A compound of the formula Id:

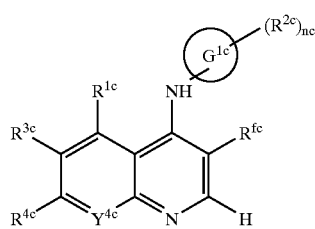

(Id)

wherein:

$G^{1c}$ represents phenyl or 1H-indazol-6-yl;

$Y^{4c}$ represents C—H;

$R^{fc}$ represents hydrogen or fluoro;

$R^{2c}$ represents hydroxy, halogeno, $C_{1-3}$alkyl, $C_{1-3}$alkoxy, $C_{1-3}$alkanoyloxy, trifluoromethyl, cyano, amino or nitro;

nc is an integer from 1 to 3;

$R^{1c}$ represents hydrogen, hydroxy, methoxy, amino, nitro or halogeno;

$R^{3c}$ represents hydrogen, hydroxy, halogeno, cyano, nitro, trifluoromethyl, $C_{1-3}$alkyl, $C_{1-3}$alkoxy, $C_{1-3}$alkylthio, or —$NR^{6c}R^{7c}$ (wherein $R^{6c}$ and $R^{7c}$, which may be the same or different, each represents hydrogen or $C_{1-3}$alkyl), and additionally $R^{3c}$ may have any of the values of $R^{5c}$—$X^{1c}$— (wherein $R^{5c}$ and $X^{1c}$ are as defined below);

$R^{4c}$ represents cyano, —$NR^{8c}R^{9c}$ (wherein $R^{8c}$ and $R^{9c}$, which may be the same or different, each represents $C_{1-3}$alkyl), or a group $R^{5c}$—$X^{1c}$— wherein $X^{1c}$ represents —OCO—, —S—, —SO—, —$SO_2$—, —$NR^{10c}CO$—, —$CONR^{11c}$—, —$SO_2NR^{12c}$— or —$NR^{14c}$— (wherein $R^{11c}$, $R^{12c}$ and $R^{14c}$ each independently represents hydrogen, $C_{1-3}$alkyl or $C_{1-3}$alkoxy$C_{2-3}$alkyl, and $R^{10c}$ represents $C_{1-3}$alkyl or $C_{1-3}$alkoxy$C_{2-3}$alkyl), and $R^{5c}$ is selected from one of the following eight groups:

1) $C_{1-5}$alkyl which may be unsubstituted or which may be substituted with one or more groups selected from hydroxy and amino;

2) $C_{1-5}$alkyl$X^{2c}COR^{15c}$ (wherein $X^{2c}$ represents —O— or —$NR^{16c}$— (wherein $R^{16c}$ represents hydrogen, $C_{1-3}$alkyl or $C_{1-3}$alkoxy$C_{2-3}$alkyl) and $R^{15c}$ represents —$NR^{17c}R^{18c}$— or —$OR^{19c}$— (wherein $R^{17c}$, $R^{18c}$ and $R^{19c}$ which may be the same or different each represents hydrogen, $C_{1-3}$alkyl or $C_{1-3}$alkoxy$C_{2-3}$alkyl));

3) $C_{1-5}$alkyl$X^{3c}R^{20c}$ (wherein $X^{3c}$ represents —O—, —S—, —SO—, —$SO_2$—, —OCO—, —$NR^{21c}CO$—, —$CONR^{22c}$—, —$SO_2NR^{23c}$—, —$NR^{24c}SO_2$— or $NR^{25c}$— (wherein $R^{21c}$, $R^{22c}$, $R^{23c}$, $R^{24c}$ and $R^{25c}$ each independently represents hydrogen, $C_{1-3}$alkyl or $C_{1-3}$alkoxy$C_{2-3}$alkyl) and $R^{20c}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);

4) $C_{1-5}$alkyl$X^{4c}C_{1-5}$alkyl$X^{5c}R^{26c}$ (wherein $X^{4c}$ and $X^{5c}$ which may be the same or different are each —O—, —S—, —SO—, —$SO_2$—, —$NR^{27c}CO$—, —$CONR^{28c}$—, —$SO_2NR^{29c}$—, —$NR^{30c}SO_2$— or —$NR^{31c}$— (wherein $R^{27c}$, $R^{28c}$, $R^{29c}$, $R^{30c}$ and $R^{31c}$ each independently represents hydrogen, $C_{1-3}$alkyl or $C_{1-3}$alkoxy$C_{2-3}$alkyl) and $R^{26c}$ represents hydrogen or $C_{1-3}$alkyl);

5) $C_{1-5}$alkyl$R^{32c}$ (wherein $R^{32c}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);

6) $(CH_2)_{qc}X^{6c}R^{33c}$ (wherein qc is an integer from 0 to 5, $X^{6c}$ represents a direct bond, —O—, —S—, —SO—, —$NR^{34c}CO$—, —$CONR^{35c}$—, —$SO_2NR^{36c}$—, —$NR^{37c}SO_2$— or —$NR^{38c}$— (wherein $R^{34c}$, $R^{35c}$, $R^{36c}$, $R^{37c}$ and $R^{38c}$ each independently represents hydrogen, $C_{1-3}$alkyl or $C_{1-3}$alkoxy$C_{2-3}$alkyl) and $R^{33c}$ is a phenyl group, a pyridone group or a 5 or 6 membered aromatic heterocyclic group with 1 to 3 heteroatoms selected from O, N and S, which phenyl, pyridone or aromatic heterocyclic group may carry up to 5 substituents selected from hydroxy, halogeno, $C_{1-4}$alkyl, $C_{1-4}$alkoxy, $C_{1-4}$hydroxyalkyl, $C_{1-4}$hydroxyalkoxy, carboxy, cyano, —$CONR^{39c}R^{40c}$ and —$NR^{41c}COR^{42c}$ (wherein $R^{39c}$, $R^{40c}$, $R^{41c}$ and $R^{42c}$, which may be the same or different, each represents hydrogen or $C_{1-4}$alkyl));

7) $C_{2-6}$alkenyl$R^{32c}$ (wherein $R^{32c}$ is as defined above); and

8) $C_{2-6}$alkynyl$R^{32c}$ (wherein $R^{32c}$ is as defined above);

or a salt thereof.

13. A compound as claimed in claim 10 wherein $R^{5c}$ is 2-methoxyethyl, 3-methoxypropyl, 2-(methylsulphinyl)ethyl, 2-(methylsulphonyl)ethyl,2-(N,N-dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazine-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino) propyl, 2-methylthiazol-4-ylmethyl, 2-acetamidothiazol-4ylmethyl, 1-methylimidazol-2-ylmethyl, 2-(imidazol-1-yl) ethyl, 2-(1,2,3-triazol-1-yl)ethyl, 2-(1,2,-3-triazol-2-yl) ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, benzyl, 2-(4-pyridyloxy)ethyl, 2-(4-pyridylamino)ethyl, 2-(4-oxo-1,4-dihydro-1-pyridyl)ethyl, 3-(3-pyridyl)propyl, 2-((N-(1-methylimidazol-4-ylsulphonyl)-N-methyl)amino) ethyl, 2-((N-methyl-N-4-pyridyl)amino)ethyl, 2-(4-oxidomorpholino)ethyl, 3-(4-oxidomorpholino)propyl, 3-(4-oxo-1,4-dihydro-1-pyridyl)propyl, 3-(1,2,4-triazol-1-yl)propyl, 3-(1,2,4-triazol-4-yl)propyl, 3-(4-pyridyloxy) propyl, 3-(4-pyridylamino)propyl, 2-(2-methylimidazol-1-yl)ethyl, 3-(2-methylimidazol-1-yl)propyl, 2-(5-methyl-1,2,4-triazol-1-yl)ethyl, 3-(5-methyl-1,2,4-triazol-1-yl)propyl, 3-(imidazol-1-yl)propyl, 3-(1,2,3-triazol-1-yl)propyl, 3-(1,2,3-triazol-2-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy) ethyl, 2-(4-methylpiperazin-1-yl)ethyl, 3-(4- methylpiperazin-1-yl)propyl, 3-(methylsulphinyl)propyl or 3-(methylsulphonyl)propyl.

14. A compound as claimed in claim 10 wherein $R^{5c}$ is 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazine-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, benzyl, 2-(4-pyridyloxy)ethyl, 2-(4-pyridylamino)ethyl or 2-(4-oxo-1,4-dihydro-1-pyridyl)ethyl.

15. The compound as claimed in claim 1 or claim 9 wherein $R^{1c}$ is hydrogen.

16. The compound as claimed in claim 1 or claim 9 wherein $R^{fc}$ is hydrogen.

17. The compound as claimed in claim 1 or claim 9 wherein $G^{1c}$ is phenyl.

18. The compound as claimed in claim 1 or claim 9 wherein the phenyl group bearing $(R^{2c})_{nc}$ is the 2-fluoro-5-hydroxy-4-methylphenyl group, the 4-chloro-2-fluoro-5-hydroxyphenyl group, the 4-chloro-2-fluorophenyl group, the 3-hydroxy-4-methylphenyl group, the 3-hydroxyphenyl group or the 4-bromo-2-fluoro-5-hydroxyphenyl group.

19. The compound as claimed in claim 1 or claim 9 wherein $R^{4c}$ represents cyano or a group $R^{5c}$—$X^{1c}$—, wherein $R^{5c}$ and $X^{1c}$ are as defined in claim 1 or claim 9.

20. A compound as claimed in any one of claims 1, 3 to 8, 9, 10, and 2–13 in the form of a pharmaceutically acceptable salt.

21. A pharmaceutical composition which comprises as active ingredient a compound of formula I or a pharmaceutically acceptable salt thereof as claimed in any one of claims 1, 3 to 8, 9, 10 and 2–14 in association with a pharmaceutically acceptable excipient or carrier.

22. A method for producing an antiangiogenic and/or vascular permeability reducing effect in a warm-blooded animal in need of such treatment which comprises administering to said animal an effective amount of a compound of formula I or a pharmaceutically acceptable salt thereof as claimed in any one of claims 1, 3 to 8, 9, 10 and 2–14.

23. A process for the preparation of a compound of formula Id or salt thereof

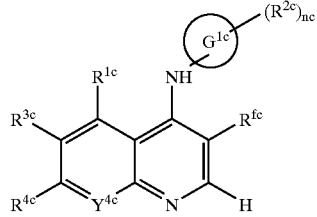

(Id)

wherein:
G$^{1c}$ represents phenyl or 1H-indazol-6-yl;
Y$^{4c}$ represents C—H;
R$^{fc}$ represents hydrogen or fluoro;
R$^{2c}$ represents hydroxy, halogeno, C$_{1-3}$alkyl, C$_{1-3}$alkoxy, C$_{1-3}$alkanoyloxy, trifluoromethyl, cyano, amino or nitro;

nc is an integer from 1 to 3;
R$^{1c}$ represents hydrogen, hydroxy, methoxy, amino, nitro or halogeno;
R$^{3c}$ represents hydrogen, hydroxy, halogeno, cyano, nitro, trifluoromethyl, C$_{1-3}$alkyl, C$_{-3}$alkoxy, C$_{1-3}$alkylthio, or —NR$^{6c}$R$^{7c}$ (wherein R$^{6c}$ and R$^{7c}$, which may be the same or different, each represents hydrogen or C$_{1-3}$alkyl), and additionally R$^{3c}$ may have any of the values of R$^{5c}$—X$^{1c}$— (wherein R$^{5c}$ and X$^{1c}$ are as defined below);
R$^{4c}$ represents cyano, —NR$^{8c}$R$^{9c}$ (wherein R$^{8c}$ and R$^{9c}$, which may be the same or different, each represents C$_{1-3}$alkyl), or a group R$^{5c}$—X$^{1c}$— wherein X$^{1c}$ represents —OCO—, —S—, —SO—, —SO$_2$—, —CONR$^{11c}$—, —SO$_2$NR$^{12c}$— or —NR$^{14c}$— (wherein R$^{11c}$, R$^{12c}$ and R$^{14c}$ each independently represents hydrogen, C$_{1-3}$alkyl or C$_{1-3}$alkoxyC$_{2-3}$alkyl), and R$^{5c}$ is selected from one of the following eight groups:
1) C$_{1-5}$alkyl which may be unsubstituted or which may be substituted with one or more groups selected from hydroxy and amino;
2) C$_{1-5}$alkylX$^{2c}$COR$^{15c}$ (wherein X$^{2c}$ represents —O— or —NR$^{16c}$— (wherein R$^{16c}$ represents hydrogen, C$_{1-3}$alkyl or C$_{1-3}$alkoxyC$_{2-3}$alkyl) and R$^{15c}$ represents —NR$^{17c}$R$^{18c}$— or —OR$^{19c}$— (wherein R$^{17c}$, R$^{18c}$ and R$^{19c}$ which may be the same or different each represents hydrogen, C$_{1-3}$alkyl or C$_{1-3}$alkoxyC$_{2-3}$alkyl));
3) C$_{1-5}$alkylX$^{3c}$R$^{20c}$ (wherein X$^{3c}$ represents —O—, —S—, —SO—, —SO$_2$—, —OCO—, —NR$^{21c}$CO—, —CONR$^{22c}$—, —SO$_2$NR$^{23c}$—, —NR$^{24c}$SO$_2$— or —NR$^{25c}$— (wherein R$^{21c}$, R$^{22c}$, R$^{23c}$, R$^{24c}$ and R$^{25c}$ each independently represents hydrogen, C$_{1-3}$alkyl or C$_{1-3}$alkoxyC$_{2-3}$alkyl) and R$^{20c}$ represents hydrogen, C$_{1-3}$alkyl, cyclopentyl, cyclohexyl or a 5 or 6 membered saturated heterocyclic group with one or two heteroatoms, selected independently from O, S and N, which C$_{1-3}$alkyl group may bear one or two substituents selected from oxo, hydroxy, halogeno and C$_{1-4}$alkoxy and which cyclic group may bear one or two substituents selected from oxo, hydroxy, halogeno, C$_{1-4}$alkyl, C$_{1-4}$hydroxyalkyl and C$_{1-4}$alkoxy);
4) C$_{1-5}$alkylX$^{4c}$C$_{1-5}$alkylX$^{5c}$R$^{26c}$ (wherein X$^{4c}$ and X$^{5c}$ which may be the same or different are each —O—, —S—, —SO—, —SO$_2$—, —NR$^{27c}$CO—, —CONR$^{28c}$—, —SO$_2$NR$^{29c}$—, —NR$^{30c}$SO$_2$— or —NR$^{31c}$— (wherein R$^{27c}$, R$^{28c}$, R$^{29c}$, R$^{30c}$ and R$^{31c}$ each independently represents hydrogen, C$_{1-3}$alkyl or C$_{1-3}$alkoxyC$_{2-3}$alkyl) and R$^{26c}$ represents hydrogen or C$_{1-3}$alkyl);
5) C$_{1-5}$alkylR$^{32c}$ (wherein R$^{32c}$ is a 5 or 6 membered saturated heterocyclic group with one or two heteroatoms, selected independently from O, S and N, which heterocyclic group may bear one or two substituents selected from oxo, hydroxy, halogeno, C$_{1-4}$alkyl, C$_{1-4}$hydroxyalkyl and C$_{1-4}$alkoxy);
6) (CH$_2$)$_{qc}$X$^{6c}$R$^{33c}$ (wherein qc is an integer from 0 to 5, X$^{6c}$ represents a direct bond, —O—, —S—, —SO—, —NR$^{34c}$CO—, —CONR$^{35c}$—, —SO$_2$NR$^{36c}$—, —NR$^{37c}$SO$_2$— or —NR$^{38c}$— (wherein R$^{34c}$, R$^{35c}$, R$^{36c}$, R$^{37c}$ and R$^{38c}$ each independently represents hydrogen, C$_{1-3}$alkyl or C$_{1-3}$alkoxyC$_{2-3}$alkyl) and R$^{33c}$ is a phenyl group, a pyridone group or a 5 or 6 membered aromatic heterocyclic group with 1 to 3 heteroatoms selected from O, N and S, which phenyl, pyridone or aromatic heterocyclic group may carry up to 5 substituents selected from hydroxy, halogeno, $C_{1-4}$alkyl, $C_{1-4}$alkoxy, $C_{1-4}$hydroxyalkyl, $C_{1-4}$hydroxyalkoxy, carboxy, cyano, —$CONR^{39c}R^{40c}$ and —$NR^{41c}COR^{42c}$ (wherein $R^{39c}$, $R^{40c}$, $R^{41c}$ and $R^{42c}$, which may be the same or different, each represents hydrogen or $C_{1-4}$alkyl));

7) $C_{2-6}$alkenyl$R^{32c}$ (wherein $R^{32c}$ is as defined herein); and

8) $C_{2-6}$alkynyl$R^{32c}$ (wherein $R^{32c}$ is as defined herein); which process comprises:

(a) the reaction of a compound of the formula III:

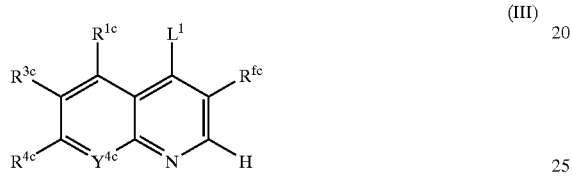

(III)

(wherein $R^{1c}$, $R^{3c}$, $R^{4c}$, $Y^{4c}$, and $R^{fc}$ are as defined above and $L^1$ is a displaceable moiety), with a compound of the formula IV:

(IV)

(wherein $G^{1c}$, $R^{2c}$ and nc are as defined above) whereby to obtain compounds of the formula Id and salts thereof;

(b) where the group $G^{1c}$, as defined above, represents a phenyl group carrying one or more hydroxy groups, a compound of the formula Id and salts thereof can be prepared by the deprotection of a compound of formula V:

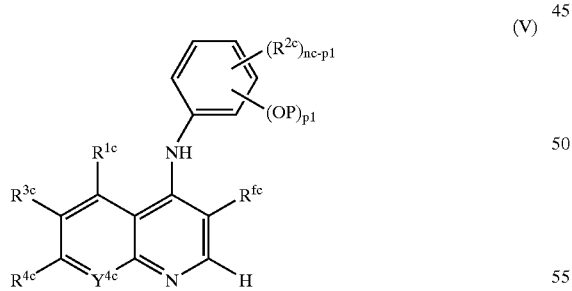

(V)

(wherein nc, $R^{1c}$, $R^{2c}$, $R^{3c}$, $R^{4c}$, $Y^4$, and $R^{fc}$ are as defined above, P represents a phenolic hydroxy protecting group and p1 is an integer from 1 to 5 equal to the number of protected hydroxy groups and such that nc-p1 is equal to the number of $R^{2c}$ substituents which are not protected hydroxy);

(c) compounds of formula Id and salts thereof wherein a substituent $R^{4c}$ is $R^{5c}$ $X^{1c}$— and wherein $X^{1c}$ is —S— or —$NR^{14c}$ can be prepared by the reaction of a compound of the formula VI:

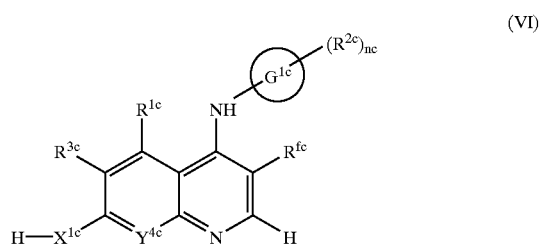

(VI)

(wherein nc, $X^{1c}$, $Y^{4c}$, $G^{1c}$, $R^{1c}$, $R^{2c}$, $R^{3c}$, and $R^{fc}$ are as defined above) with a compound of formula VII:

(VII)

(wherein $R^{5c}$ and $L^1$ are as defined above);

(d) compounds of the formula Id and salts thereof wherein a substituent $R^{3c}$ is $R^{5c}$—$X^1$— and wherein $R^{5c}$ is $C_{1-5}$alkyl$R^{61c}$ wherein $R^{61c}$ is selected from one of the following two groups:

1) $X^{11c}R^{17c}$ (wherein $X^{11c}$ represents —O—, —S—, —$SO_2$—, —$NR^{62c}CO$—, —$NR^{63c}SO_2$— or —$NR^{64c}$— (wherein $R^{62c}$, $R^{63c}$ and $R^{64c}$, each independently represents hydrogen, $C_{1-3}$alkyl or $C_{1-3}$alkoxy$C_{2-3}$alkyl) and $R^{17c}$ is as defined above); and 2) $X^{12c}C_{1-5}$alkyl$X^{5c}R^{23c}$ (wherein $X^{12c}$ represents —O—, —S—, —$SO_2$—, —$NR^{65c}CO$—, —$NR^{66c}SO_2$— or —$NR^{67c}$— (wherein $R^{65c}$, $R^{66c}$ and $R^{67c}$, each independently represents hydrogen, $C_{1-3}$alkyl or $C_{1-3}$alkoxy$C_{2-3}$alkyl) and $X^{5c}$ and $R^{23c}$ are as defined above); may be prepared by reacting a compound of the formula VIII:

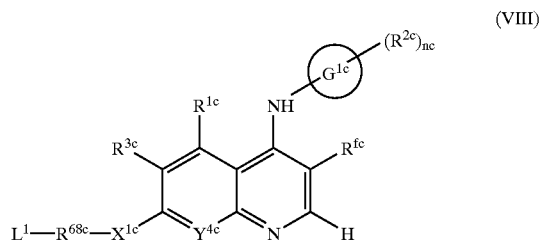

(VIII)

(wherein $L^1$, $X^{1c}$, $G^{1c}$, $Y^{4c}$, $R^{1c}$, $R^{2c}$, $R^{3c}$, and nc are as defined above and $R^{68c}$ is $C_{1-5}$alkyl) with a compound of the formula IX:

(IX)

(wherein $R^{61c}$ is as defined herein) to give a compound of the formula Id; compounds of the formula Id wherein a substituent $R^{3c}$ is $R^{5c}$—$X^{1c}$— and wherein $R^{5c}$ is $C_{2-5}$alkyl$R^{59c}$, (wherein $R^{59c}$ is 5 or 6 membered saturated heterocyclic group with one or two heteroatoms of which one is N and the other is selected independently from O, S and N, which heterocyclic group is linked to $C_{2-5}$alkyl through a nitrogen atom and which heterocyclic group may bear one or two substituents selected from oxo, hydroxy, halogeno, $C_{1-3}$alkyl, $C_{1-3}$hydroxyalkyl and $C_{1-3}$alkoxy), may be prepared by reacting a compound of formula VIII (wherein $R^{61c}$ is $C_{2-5}$alkyl) with a compound of the formula IXa:

$R^{59c}$—H  (IXa)

(wherein $R^{59}$ is as defined herein) to give a compound of the formula Id;

(e) compounds of the formula Id and salts thereof wherein a substituent $R^{3c}$ is represented by —$NR^{6c}R^{7c}$, where one or both of $R^{6c}$ and $R^{7c}$ are $C_{1-3}$alkyl, may be effected by the reaction of compounds of formula Id wherein the substituent $R^{3c}$ is an amino group and an alkylating agent;

(f) compounds of formula Id and salts thereof wherein one or more of the substituents $R^{2c}$ and $R^{3c}$ is an amino group may be effected by the reduction of a corresponding compound of formula Id wherein the substituent(s) at the corresponding position(s) of the heterocyclic/quinoline and/or heterocyclic/phenyl ring is/are a nitro group(s); and when a salt of a compound of formula Id is required, reaction of the compound obtained with an acid or base whereby to obtain the desired salt.

24. A process for the preparation of a compound of formula Id or salt thereof

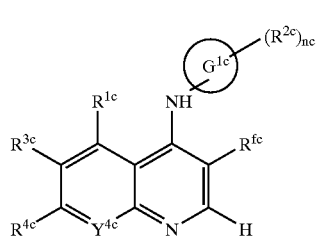

(Id)

wherein:

$G^{1c}$ represents phenyl or 1H-indazol-6-yl;

$Y^{4c}$ represents C—H;

$R^{fc}$ represents hydrogen or fluoro;

$R^{2c}$ represents hydroxy, halogeno, $C_{1-3}$alkyl, $C_{1-3}$alkoxy, $C_{1-3}$alkanoyloxy, trifluoromethyl, cyano, amino or nitro;

nc is an integer from 0 to 5;

$R^{1c}$ represents hydrogen, hydroxy, methoxy, amino, nitro or halogeno;

$R^{3c}$ represents hydrogen, hydroxy, halogeno, cyano, nitro, trifluoromethyl, $C_{1-3}$alkyl, $C_{1-3}$alkoxy, $C_{1-3}$alkylthio, or —$NR^{6c}R^{7c}$ (wherein $R^{6c}$ and $R^{7c}$, which may be the same or different, each represents hydrogen or $C_{1-3}$alkyl), and additionally $R^{3c}$ may have any of the values of $R^{5c}$—$X^{1c}$— (wherein $R^{5c}$ and $X^{1c}$ are as defined below);

$R^{4c}$ represents cyano, —$NR^{8c}R^{9c}$ (wherein $R^{8c}$ and $R^{9c}$, which may be the same or different, each represents $C_{1-3}$alkyl), or a group $R^{5c}$—$X^{1c}$— wherein $X^{1c}$ represents —O—, —$CH_2$—, —OCO—, —S—, —SO—, —$SO_2$—, —$NR^{10c}CO$—, —$CONR^{12c}$—, —$SO_2NR^{12c}$—, —$NR^{13c}SO_2$— or —$NR_{4c}$— (wherein $R^{10c}$, $R^{11c}$, $R^{12c}$, $R^{13c}$, and $R^{14c}$ each independently represents hydrogen, $C_{1-3}$alkyl or $C_{1-3}$alkoxy$C_{2-3}$alkyl), and $R^{5c}$ is selected from one of the following eight groups:

1) $C_{1-5}$alkyl$X^{2c}COR^{15c}$ (wherein $X^{2c}$ represents —O— or —$NR^{16c}$— (wherein $R^{16c}$ represents hydrogen, $C_{1-3}$alkyl or $C_{1-3}$alkoxy$C_{2-3}$alkyl) and $R^{15c}$ represents —$NR^{17c}R^{18c}$— or —$OR^{19c}$— (wherein $R^{17c}$, $R^{18c}$ and $R^{19c}$ which may be the same or different each represents hydrogen, $C_{1-3}$alkyl or $C_{1-3}$alkoxy$C_{2-3}$alkyl));

2) $C_{1-5}$alkyl$X^{3c}R^{20c}$ (wherein $X^{3c}$ represents —O—, —S—, —SO—, —$SO_2$—, —OCO—, —$NR^{12c}CO$—, —$CONR^{22c}$—, —$SO_2NR^{23c}$, —$NR^{24c}SO_2$— or $NR^{25c}$— (wherein $R^{21c}$, $R^{22c}$, $R^{23c}$, $R^{24c}$ and $R^{25c}$ each independently represents hydrogen, $C_{1-3}$alkyl or $C_{1-3}$alkoxy$C_{2-3}$alkyl) and $R^{20c}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);

3) $C_{1-5}$alkyl$X^{4c}C_{1-5}$alkyl$X^{5c}R^{26c}$ (wherein $X^{4c}$ and $X^{5c}$ which may be the same or different are each —O—, —S—, —SO—, —$SO_2$—, —$NR^{27c}CO$—, —$CONR^{21c}$—, —$SO_2NR^{29c}$—, —$NR^{30c}SO_2$— or —$NR^{31c}$— (wherein $R^{27c}$, $R^{28c}$, $R^{29c}$, $R^{30c}$ and $R^{31c}$ each independently represents hydrogen, $C_{1-3}$alkyl or $C_{1-3}$alkoxy$C_{2-3}$alkyl) and $R^{26c}$ represents hydrogen or $C_{1-3}$alkyl);

4) $C_{1-5}$alkyl$R^{32c}$ (wherein $R^{32c}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);

5) $(CH_2)_{qc}X^{6c}R^{33c}$ (wherein qc is an integer from 0 to 5, $X^{6c}$ represents a direct bond, —O—, —S—, —SO—, —$SO_2$—, —$NR^{34c}CO$—, —$CONR^{35c}$—, —$SO_2NR^{36c}$—, —$NR^{37c}SO_2$— or —$NR^{38c}$— (wherein $R^{34c}$, $R^{35c}$, $R^{36c}$, $R^{37c}$ and $R^{38c}$ each independently represents hydrogen, $C_{1-3}$alkyl or $C_{1-3}$alkoxy$C_{2-3}$alkyl) and $R^{33c}$ is a pyridone group or a 5 or 6 membered aromatic heterocyclic group with 1 to 3 heteroatoms selected from O, N and S, which pyridone or aromatic heterocyclic group may carry up to 5 substituents selected from hydroxy, halogeno, $C_{1-4}$alkyl, $C_{1-4}$alkoxy, $C_{1-4}$hydroxyalkyl, $C_{1-4}$hydroxyalkoxy, carboxy, cyano, —$CONR^{39c}R^{40c}$ and —$NR^{41c}COR^{42c}$ (wherein $R^{39c}$, $R^{40c}$, $R^{41c}$ and $R^{42c}$, which may be the same or different, each represents hydrogen or $C_{1-4}$alkyl));

6) $C_{2-6}$alkenyl$R^{32c}$ (wherein $R^{32c}$ is as defined herein); and

7) $C_{2-6}$alkynyl$R^{32c}$ (wherein $R^{32c}$ is as defined herein);

which process comprises:

(a) the reaction of a compound of the formula III:

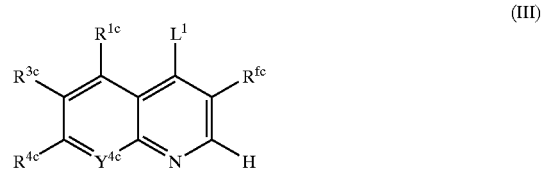

(III)

(wherein $R^{1c}$, $R^{3c}$, $R^{4c}$, $Y^{4c}$, and $R^{fc}$ are as defined above and $L^1$ is a displaceable moiety), with a compound of the formula IV:

(IV)

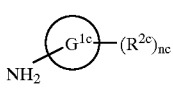

(wherein $G^{1c}$, $R^{2c}$ and nc are as defined above) whereby to obtain compounds of the formula Id and salts thereof;

(b) where the group $G^{1c}$, as defined above, represents a phenyl group carrying one or more hydroxy groups, a compound of the formula Id and salts thereof can be prepared by the deprotection of a compound of formula V:

(V)

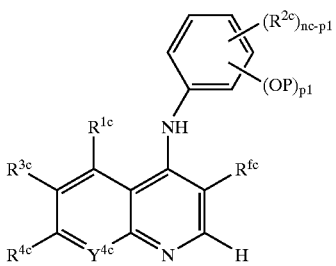

(wherein nc, $R^{1c}$, $R^{2c}$, $R^{3c}$, $R^{4c}$, $Y^4$, and $R^{fc}$ are as defined above, P represents a phenolic hydroxy protecting group and p1 is an integer from 1 to 5 equal to the number of protected hydroxy groups and such that nc-p1 is equal to the number of $R^{2c}$ substituents which are not protected hydroxy);

(c) compounds of formula Id and salts thereof wherein a substituent $R^{4c}$ is $R^{5c}$—$X^{1c}$— and wherein $X^{1c}$ is —O—, —S— or —NR$^{14c}$— can be prepared by the reaction of a compound of the formula VI:

(VI)

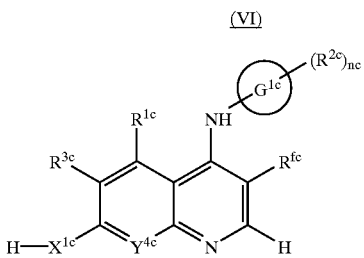

(wherein nc, $X^{1c}$, $Y^{4c}$, $G^{1c}$, $R^{1c}$, $R^{2c}$, $R^{3c}$, and $R^{fc}$ are as defined above) with a compound of formula VII:

$R^{5c}$—$L^1$ (VI)

(wherein $R^{5c}$ and $L^1$ are as defined above);

(d) compounds of the formula Id and salts thereof wherein a substituent $R^{3c}$ is $R^{5c}$—$X^{1c}$— and wherein $R^{5c}$ is $C_{1-5}$alkyl$R^{61c}$, wherein $R^{61c}$ is selected from one of the following two groups:
1) $X^{11c}R^{17c}$ (wherein $X^{11c}$ represents —O—, —S—, —SO$_2$—, —NR$^{62c}$CO—, —NR$^{63c}$SO$_2$— or —NR$^{64c}$— (wherein $R^{62c}$, $R^{63c}$ and $R^{64c}$, each independently represents hydrogen, $C_{1-3}$alkyl or $C_{1-3}$alkoxyC$_{2-3}$alkyl) and $R^{17c}$ is as defined above); and 2) $X^{12c}C_{1-5}$alkyl$X^{5c}R^{23c}$ (wherein $X^{12c}$ represents —O—, —S—, —SO$_2$—, —NR$^{65c}$CO—, —NR$^{66c}$SO$_2$— or —NR$^{67c}$— (wherein $R^{65c}$, $R^{66c}$ and $R^{67c}$, each independently represents hydrogen, $C_{1-3}$alkyl or $C_{1-3}$alkoxyC$_{2-3}$alkyl) and $X^{5c}$ and $R^{23c}$ are as defined above); may be prepared by reacting a compound of the formula VIII:

(VIII)

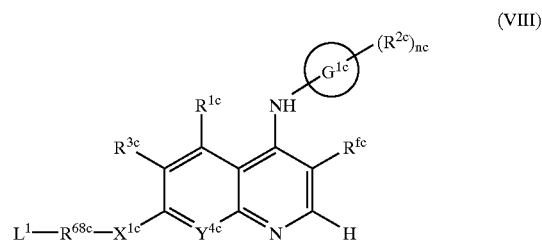

(wherein $L^1$, $X^{1c}$, $G^{1c}$, $Y^{4c}$, $R^{1c}$, $R^{2c}$, $R^{3c}$, and nc are as defined above and $R^{68c}$ is $C_{1-5}$alkyl) with a compound of the formula IX:

$R^{61c}$—H (IX)

(wherein $R^{61c}$ is as defined herein) to give a compound of the formula Id; compounds of the formula Id wherein a substituent $R^{3c}$ is $R^{5c}$—$X^{1c}$— and wherein $R^{5c}$ is $C_{2-5}$alkyl$R^{59c}$, (wherein $R^{59c}$ is 5 or 6 membered saturated heterocyclic group with one or two heteroatoms of which one is N and the other is selected independently from O, S and N, which heterocyclic group is linked to $C_{2-5}$alkyl through a nitrogen atom and which heterocyclic group may bear one or two substituents selected from oxo, hydroxy, halogeno, $C_{1-3}$alkyl, $C_{1-3}$hydroxyalkyl and $C_{1-3}$alkoxy), may be prepared by reacting a compound of formula VIII (wherein $R^{61c}$ is $C_{2-5}$alkyl) with a compound of the formula IXa:

$R^{59c}$—H (IXa)

(wherein $R^{59}$ is as defined herein) to give a compound of the formula Id;
(e) compounds of the formula Id and salts thereof wherein a substituent $R^{3c}$ is represented by —NR$^{6c}$R$^{7c}$, where one or both of $R^{6c}$ and $R^{7c}$ are $C_{1-3}$alkyl, may be effected by the reaction of compounds of formula Id wherein the substituent $R^{3c}$ is an amino group and an alkylating agent;
(f) compounds of formula Id and salts thereof wherein one or more of the substituents $R^{2c}$ and $R^{3c}$ is an amino group may be effected by the reduction of a corresponding compound of formula Id wherein the substituent(s) at the corresponding position(s) of the heterocyclic/quinoline and/or heterocyclic/phenyl ring is/are a nitro group(s);

and when a salt of a compound of formula Id is required, reaction of the compound obtained with an acid or base whereby to obtain the desired salt.

* * * * *